United States Patent
Van Den Brink et al.

(10) Patent No.: US 9,663,578 B2
(45) Date of Patent: May 30, 2017

(54) MONOCLONAL ANTIBODIES AGAINST CD32B

(71) Applicant: GENMAB A/S, Copenhagen (DK)

(72) Inventors: Edward Norbert Van Den Brink, Halfweg (NL); Paul Parren, Odijk (NL); Jan Van De Winkel, Zeist (NL); Aran Frank Labrijn, Nigtevecht (NL); Frank Everhardus Martinus Rebers, Utrecht (NL); Esther Cornelia Wilhelmina Breij, Utrecht (NL)

(73) Assignee: GENMAB A/S, Copenhagen (DK)

( * ) Notice: Subject to any disclaimer, the term of this patent is extended or adjusted under 35 U.S.C. 154(b) by 0 days.

(21) Appl. No.: 14/317,600

(22) Filed: Jun. 27, 2014

(65) Prior Publication Data

US 2015/0004177 A1 Jan. 1, 2015

Related U.S. Application Data

(62) Division of application No. 12/811,637, filed as application No. PCT/DK2008/050335 on Dec. 19, 2008, now Pat. No. 8,802,089.

(60) Provisional application No. 61/009,877, filed on Jan. 3, 2008.

(30) Foreign Application Priority Data

Jan. 3, 2008 (DK) ................... 2008 00006

(51) Int. Cl.
*A61K 39/395* (2006.01)
*C07K 16/28* (2006.01)
*A61K 39/00* (2006.01)

(52) U.S. Cl.
CPC ...... *C07K 16/283* (2013.01); *A61K 2039/505* (2013.01); *C07K 2317/21* (2013.01); *C07K 2317/30* (2013.01); *C07K 2317/33* (2013.01); *C07K 2317/55* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

2005/0191293 A1  9/2005  Deshpande et al.

FOREIGN PATENT DOCUMENTS

| WO | 2005/051999 A2 | 6/2005 |
|---|---|---|
| WO | 2006/028956 A2 | 3/2006 |
| WO | 2006/039418 A2 | 4/2006 |
| WO | 2006/066078 A2 | 6/2006 |
| WO | WO/2006/066078 | * 6/2006 |

OTHER PUBLICATIONS

Amigorena, Sebastian et al., "Cytoplasmic Domain Heterogeneity and Functions of IgG Fc Receptors in B Lymphocytes," Science, vol. 256:1808-1812 (1992).
Brooks, David G. et al., "Structure and Expression of Human IgG FcRII(CD32)," J. Exp. Med., vol. 170:1369-1385 (1989).
Daeron, Marc, "Fc Receptor Biology," Annu. Rev. Immunol., vol. 15:203-234 (1997).
Rankin, Christopher T. et al., "CD32B, the human inhibitory Fc-g receptir IIB, as a target for monoclonal antibody therapy of B-cell lymphoma," Blood, vol. 108(7):2384-2391 (2006).
Ravetch, Jeffrey V. et al., "IgG Fc Receptors," Annu. Rev. Immunol., vol. 19:275-290 (2001).
Takai, Toshiyuki, "Roles of Fc Receptors in Autoimmunity," Nature Rev. Immunol., vol. 2(8):580-592 (2002).
Van Den Herik-Oudijk, Ingrid E. et al., "Functional Analysis of Human FcgRII (CD32) Isoforms Expressed in B Lymphocytes," Journal of Immunology, vol. 152(2):574-585 (1994).
Veri, Maria-Concetta et al., "Monoclonal antibodies capable of discriminating the human inhibitory Fcg-receptor IIB (CD32B) from the activating Fcg-receptor IIA (CD32A): biochemical, biological and functional characterization," Immunology, vol. 121:392-404 (2007).

* cited by examiner

*Primary Examiner* — Laura B Goddard
*Assistant Examiner* — Meera Natarajan
(74) *Attorney, Agent, or Firm* — Nelson Mullins Riley & Scarborough LLP; Jane E. Remillard, Esq.; Christopher L. Frank

(57) ABSTRACT

Isolated monoclonal antibodies which bind to human CD32b and related antibody-based compositions and molecules, are disclosed. Also disclosed are pharmaceutical compositions comprising the antibodies, and therapeutic and diagnostic methods for using the antibodies.

16 Claims, 19 Drawing Sheets

▽ treatment at day 6
with 20 μg per mouse

▽ treatment at day 14
with 20 μg per mouse

HuMab CD32b-028

HuMab KLH

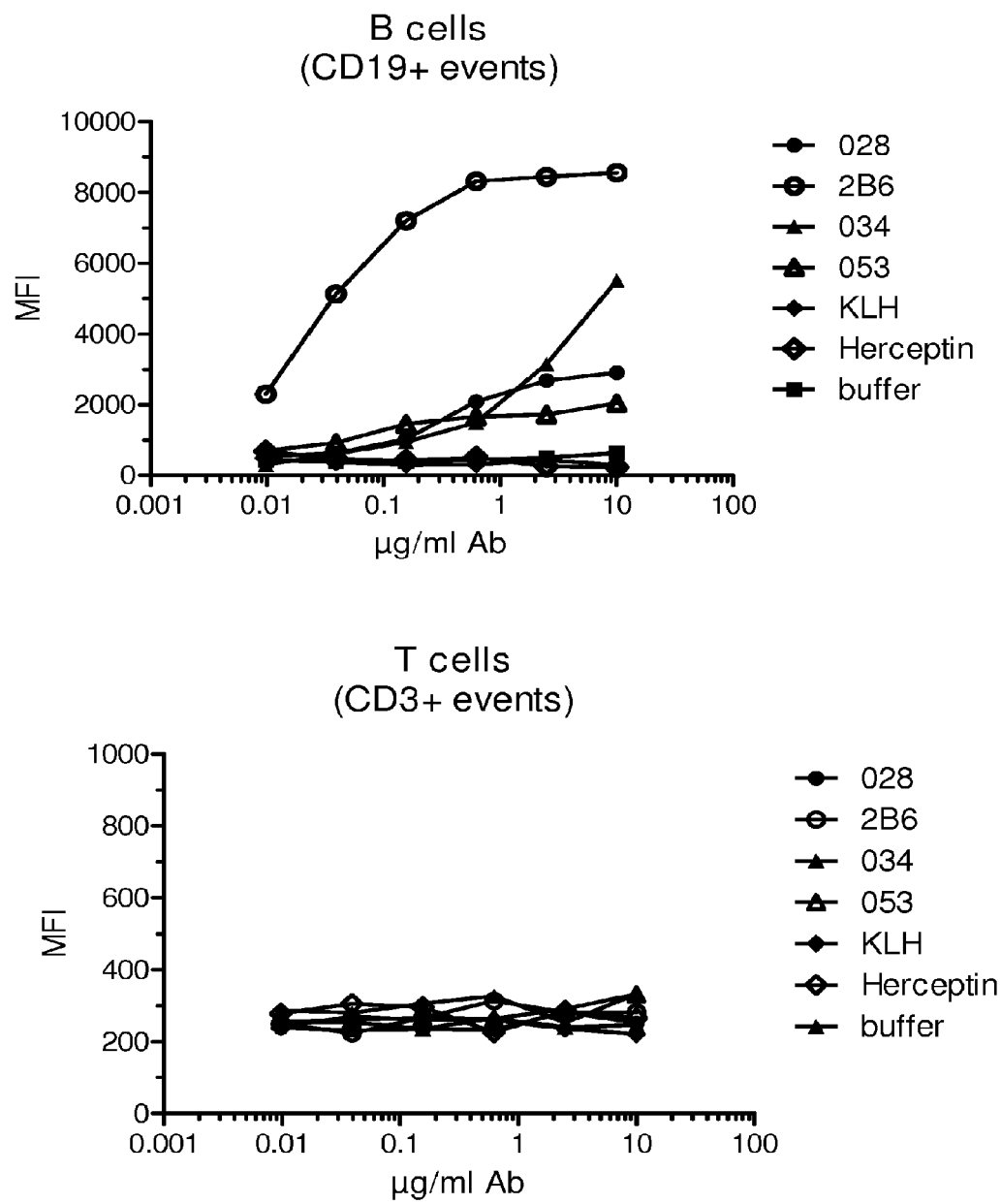

FIGURE 12

ANTIBODY 016:
SEQ ID NO:1: VH IGHV3-33*01
QVQLVESGGGVVQPGRSLRLSCAASGFTFSSYGIHWVRQAPGKGLEWVAVIGYDGSDKNYADSVKG
RFTIFRDNSKNTLYLQMNSLRAEDTAVYYCARDQLGDAFDIWGQGTMVTVSS
SEQ ID NO:2: VH CDR1 SYGIH
SEQ ID NO:3: VH CDR2 VIGYDGSDKNYADSVKG
SEQ ID NO:4: VH CDR3 DQLGDAFDI

SEQ ID NO:5: VL IGKV3-11*01
EIVLTQSPATLSLSPGERATLSCKASQSVSSSLAWYQQKPGQAPRLLIYDASNRATGIPARFSGSG
SGTDFTLTISSLEPEDFAVYYCQQRSNWPPYTFGQGTKLEIKR
SEQ ID NO:6: VL CDR1 KASQSVSSSLA
SEQ ID NO:7: VL CDR2 DASNRAT
SEQ ID NO:8: VL CDR3 QQRSNWPPYT

ANTIBODY 020:
SEQ ID NO:9: VH IGHV1-18*01
QVQLVQSGGEVKKPGASVKVSCKTSGYTFTSYGISWVRQAPGQGLEWMGWISAYNGNTKYAQKLQG
RLTMTTDTSTTAYMELRSLRSDDTAVYYCARDSAAHGMDVWGQGTTVTVSS
SEQ ID NO:10: VH CDR1 SYGIS
SEQ ID NO:11: VH CDR2 WISAYNGNTKYAQKLQG
SEQ ID NO:12: VH CDR3 DSAAHGMDV

SEQ ID NO:13: VL IGKV1D-16*01
DIQMTQSPSSLSASVGDRVTITCRASQGISSWLAWYQQKPEKAPKSLIYAASSLQSGVPSRFRGSG
SGTDFTLTISSLQPEDFATYYCQQYNSYPYTFGQGTKLEIKR
SEQ ID NO:14: VL CDR1 RASQGISSWLA
SEQ ID NO:15: VL CDR2 AASSLQS
SEQ ID NO:16: VL CDR3 QQYNSYPYT

ANTIBODY 022:
SEQ ID NO:17: VHIGHV1-18*01
QVQLVQSGAEVKKPGASVKVSCKASGYTFTSYGLSWVRQAPGQGLEWMGWISPYNGNTHYAQKLQG
RVTMTTDTSTSTADMDLRSLRSDDTAVYYCARASAAHGMDVWGQGTTVTVSS
SEQ ID NO:18: VH CDR1 SYGLS
SEQ ID NO:19: VH CDR2 WISPYNGNTHYAQKLQG
SEQ ID NO:20: VH CDR3 ASAAHGMDV

SEQ ID NO:21: VL IGKV1D-16*01
DIQMTQSPSSLSASVGDRVTITCRASQGISSWLAWYQQKPEKAPKSLIYAASSLQSGVPSRFSGSR
SGTDFTLTISSLQPEDFATYYCQQYNSYPYTFGQGTKLEIKR
SEQ ID NO:22: VL CDR1 RASQGISSWLA
SEQ ID NO:23: VL CDR2 AASSLQS
SEQ ID NO:24: VL CDR3 QQYNSYPYT

ANTIBODY 024:
SEQ ID NO:25: VH IGHV1-18*01
QVQLVQSGAEVKKPGASVKVSCKASGYTFTSYGLSWVRQAPGQGLEWMGWISPYNGNTHYAQKLQG
RVTMTTDTSTSTAYMDLRSLRSDDTAVYYCARDSAAHGMDVWGQGTTVTVSS
SEQ ID NO:26: VH CDR1 SYGLS
SEQ ID NO:27: VH CDR2 WISPYNGNTHYAQKLQG

FIGURE 12 continued...

SEQ ID NO:28: VH CDR3 DSAAHGMDV

SEQ ID NO:29: VL IGKV1D-16*01
DIQMTQSPSSLSASVGDRVTITCRASQGISSWLAWYQQKPEKAPKSLIYAASSLQSGVPSRFGSR
SGTDFTLTISSLQPEDFATYYCQQYNSYPYTFGQGTKLEIKR
SEQ ID NO:30: VL CDR1 RASQGISSWLA
SEQ ID NO:31: VL CDR2 AASSLQS
SEQ ID NO:32: VL CDR3 QQYNSYPYT

ANTIBODY 026:
SEQ ID NO:33: VH IGHV1-18*01
QVQLVQSGAEVKKPGASVKVSCKASGYTFTSYGLSWVRQAPGQGLEWMGWISAYNGNTNYAQKLQG
RVTMTTDTSTSTAYMDLRSLRSDDTAVYYCARDSAAHGMDVWGQGTTVTVSS
SEQ ID NO:34: VH CDR1 SYGLS
SEQ ID NO:35: VH CDR2 WISAYNGNTNYAQKLQG
SEQ ID NO:36: VH CDR3 DSAAHGMDV

SEQ ID NO:37: VL IGKV1D-16*01
DIQMTQSPSSLSASVGDRVTITCRASQGISSWLAWYQQKPEKAPKSLIYAASSLQSGVPSRFGSR
SGTDFTLTISSLQPEDFATYYCQQYNSYPYTFGQGTKLEIKR
SEQ ID NO:38: VL CDR1 RASQGISSWLA
SEQ ID NO:39: VL CDR2 AASSLQS
SEQ ID NO:40: VL CDR3 QQYNSYPYT

ANTIBODY 028:
SEQ ID NO:41: VH IGHV1-18*01
QVQVVQSGAEVKKPGASVKVSCKTSGYTFTSYGISWVRQAPGQGLEWMGWISAYNGNTKYAQKLQG
RLTMTTDTSTTTAYMELRSLRSDDTAVYYCARDSAAHGMDVWGQGTTVSVSS
SEQ ID NO:42: VH CDR1 SYGIS
SEQ ID NO:43: VH CDR2 WISAYNGNTKYAQKLQG
SEQ ID NO:44: VH CDR3 DSAAHGMDV

ANTIBODY 034:
SEQ ID NO:45: VH IGHV3-23*01
EVQLLESGGGLVQPGGSLRLSCAASGFTFSNFVMSWVRQAPGKGLEWVSGISGSGGNTDHADSVKG
RFTISRDNSKNTVYLQMNSLRAEDTAVYYCAKDSGGLFDYWGLGTLVTVSS
SEQ ID NO:46: VH CDR1 NFVMS
SEQ ID NO:47: VH CDR2 GISGSGGNTDHADSVKG
SEQ ID NO:48: VH CDR3 DSGGLFDY

SEQ ID NO:49: VL IGKV3-11*01
EIVLTQSPATLSLSPGERATLSCRASQSVSSYLAWYQQKPGQAPRLLIYDASNRATGIPARFSGSG
SRTDFTLTISSLEPEDFAVYYCQQRSNWPHLTFGGGTKVEIKR
SEQ ID NO:50: VL CDR1 RASQSVSSYLA
SEQ ID NO:51: VL CDR2 DASNRAT
SEQ ID NO:52: VL CDR3 QQRSNWPHLT

ANTIBODY 038:
SEQ ID NO:53: VH IGHV3-30*03
QVQLVESGGGVVQPGRSLRLSCAASGFTFSTYGMHWVRQAPGKGLEWVAVISHDGSDKYYADSVKG
RFTISRDNSKNTLYLQMNSLRAEDTAVYYCARDQSIIETFDYWGQGTLVTVSS

FIGURE 12 continued...

SEQ ID NO:54: VH CDR1 TYGMH
SEQ ID NO:55: VH CDR2 VISHDGSDKYYADSVKG
SEQ ID NO:56: VH CDR3 DQSIIETFDY

SEQ ID NO:57: VL IGKV3-11*01
EIVLTQSPATLSLSPGERATLSCRASQSVSSYLAWYQQKPGQAPRLLIYDASNRATGIPARFSGSG
SGTDFTLTISSLEPEDFAVYYCQQRSNWGFTFGPGTKVDIKR
SEQ ID NO:58: VL CDR1 RASQSVSSYLA
SEQ ID NO:59: VL CDR2 DASNRAT
SEQ ID NO:60: VL CDR3 QQRSNWGFT

ANTIBODY 053:
SEQ ID NO:61: VH IGHV3-33*01
QVQLVESGGGVVQPGRSLRLSCAVSGFTFRSYGMHWVRQAPGKGLEWVAVIWYDGSIKYYADSVKG
RFTISRDNSKNTLYLQMNSLRAEDTAVYFCAREGGRDAFDIWGQGTMVTVSS
SEQ ID NO:62: VH CDR1 SYGMH
SEQ ID NO:63: VH CDR2 VIWYDGSIKYYADSVKG
SEQ ID NO:64: VH CDR3 EGGRDAFDI

SEQ ID NO:65: VL IGKV1-13*02
AVQLTQSPSSLSASVGDRVTITCRASQGISSALAWYQQKPGKAPKLLIYDASSLESGVPSRFSGSG
SGTDFTLTISSLQPEDFATYCCQQFNSYPHTFGGGTKVEIKR
SEQ ID NO:66: VL CDR1 RASQGISSALA
SEQ ID NO:67: VL CDR2 DASSLES
SEQ ID NO:68: VL CDR3 QQFNSYPHT

ANTIBODY 063:
SEQ ID NO:69: VH IGHV3-23*01
EVQLLESGGGLVQPGGSLRLSCAASGFTFSSYAMSWVRQAPGKGLEWVSAISDSGGSTYYADSVKG
RFTISRDNSKNTLYLQMNSLRAEDTAAYYCAKEIAVALFDYWGQGTLVTVSS
SEQ ID NO:70: VH CDR1 SYAMS
SEQ ID NO:71: VH CDR2 AISDSGGSTYYADSVKG
SEQ ID NO:72: VH CDR3 EIAVALFDY

SEQ ID NO:73: VL IGKV3 11*01
EIVLTQSPATLSLSPGERATLSCRASQSVSSYLAWYQQKPGQAPRLLIYDASNRATGIPARFSGSG
SGTDFTLTISSLEPEDFAVYYCQQRSSWPPYTFGQGTKLEIKR
SEQ ID NO:74: VL CDR1 RASQSVSSYLA
SEQ ID NO:75: VL CDR2 DASNRAT
SEQ ID NO:76: VL CDR3 QQRSSWPPYT

SEQ ID NO:77:
STGXS, wherein X is L or I

SEQ ID NO:78:
WISXYNGNTXYAQKLQG, wherein X in position 4 is A or P, and X in position 10 is H,N or K

SEQ ID NO:79:
XSAAHGMDV, wherein X is A or D

```
                         SEQUENCE LISTING

<160> NUMBER OF SEQ ID NOS: 79

<210> SEQ ID NO 1
<211> LENGTH: 118
<212> TYPE: PRT
<213> ORGANISM: HOMO SAPIENS

<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Gly Tyr Asp Gly Ser Asp Lys Asn Tyr Ala Asp Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Leu Gly Asp Ala Phe Asp Ile Trp Gly Gln Gly Thr
            100                 105                 110

Met Val Thr Val Ser Ser
        115

<210> SEQ ID NO 2
<211> LENGTH: 5
<212> TYPE: PRT
<213> ORGANISM: HOMO SAPIENS

<400> SEQUENCE: 2

Ser Tyr Gly Ile His
1               5

<210> SEQ ID NO 3
<211> LENGTH: 17
<212> TYPE: PRT
<213> ORGANISM: HOMO SAPIENS

<400> SEQUENCE: 3

Val Ile Gly Tyr Asp Gly Ser Asp Lys Asn Tyr Ala Asp Ser Val Lys
1               5                   10                  15

Gly
```

-continued

```
<210> SEQ ID NO 4
<211> LENGTH: 9
<212> TYPE: PRT
<213> ORGANISM: HOMO SAPIENS

<400> SEQUENCE: 4

Asp Gln Leu Gly Asp Ala Phe Asp Ile
1               5

<210> SEQ ID NO 5
<211> LENGTH: 109
<212> TYPE: PRT
<213> ORGANISM: HOMO SAPIENS

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Ser Ser Ser
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys Arg
            100                 105

<210> SEQ ID NO 6
<211> LENGTH: 11
<212> TYPE: PRT
<213> ORGANISM: HOMO SAPIENS

<400> SEQUENCE: 6

Lys Ala Ser Gln Ser Val Ser Ser Ser Leu Ala
1               5                   10

<210> SEQ ID NO 7
<211> LENGTH: 7
<212> TYPE: PRT
<213> ORGANISM: HOMO SAPIENS

<400> SEQUENCE: 7

Asp Ala Ser Asn Arg Ala Thr
1               5

<210> SEQ ID NO 8
<211> LENGTH: 10
<212> TYPE: PRT
<213> ORGANISM: HOMO SAPIENS

<400> SEQUENCE: 8

Gln Gln Arg Ser Asn Trp Pro Pro Tyr Thr
1               5                   10

<210> SEQ ID NO 9
<211> LENGTH: 118
<212> TYPE: PRT
<213> ORGANISM: HOMO SAPIENS
```

<400> SEQUENCE: 9

Gln Val Gln Leu Val Gln Ser Gly Gly Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Lys Tyr Ala Gln Lys Leu
50                  55                  60

Gln Gly Arg Leu Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ala Ala His Gly Met Asp Val Trp Gly Gln Gly Thr
            100                 105                 110

Thr Val Thr Val Ser Ser
        115

<210> SEQ ID NO 10
<211> LENGTH: 5
<212> TYPE: PRT
<213> ORGANISM: HOMO SAPIENS

<400> SEQUENCE: 10

Ser Tyr Gly Ile Ser
1               5

<210> SEQ ID NO 11
<211> LENGTH: 17
<212> TYPE: PRT
<213> ORGANISM: HOMO SAPIENS

<400> SEQUENCE: 11

Trp Ile Ser Ala Tyr Asn Gly Asn Thr Lys Tyr Ala Gln Lys Leu Gln
1               5                   10                  15

Gly

<210> SEQ ID NO 12
<211> LENGTH: 9
<212> TYPE: PRT
<213> ORGANISM: HOMO SAPIENS

<400> SEQUENCE: 12

Asp Ser Ala Ala His Gly Met Asp Val
1               5

<210> SEQ ID NO 13
<211> LENGTH: 108
<212> TYPE: PRT
<213> ORGANISM: HOMO SAPIENS

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

```
Tyr Ala Ala Ser Ser Leu Gln Ser Gly Val Pro Ser Arg Phe Arg Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys Arg
            100                 105

<210> SEQ ID NO 14
<211> LENGTH: 11
<212> TYPE: PRT
<213> ORGANISM: HOMO SAPIENS

<400> SEQUENCE: 14

Arg Ala Ser Gln Gly Ile Ser Ser Trp Leu Ala
 1               5                  10

<210> SEQ ID NO 15
<211> LENGTH: 7
<212> TYPE: PRT
<213> ORGANISM: HOMO SAPIENS

<400> SEQUENCE: 15

Ala Ala Ser Ser Leu Gln Ser
 1               5

<210> SEQ ID NO 16
<211> LENGTH: 9
<212> TYPE: PRT
<213> ORGANISM: HOMO SAPIENS

<400> SEQUENCE: 16

Gln Gln Tyr Asn Ser Tyr Pro Tyr Thr
 1               5

<210> SEQ ID NO 17
<211> LENGTH: 118
<212> TYPE: PRT
<213> ORGANISM: HOMO SAPIENS

<400> SEQUENCE: 17

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Leu Ser Trp Val Arg Gln Ala Pro Gly Gln Gly Leu Glu Trp Met
             35                  40                  45

Gly Trp Ile Ser Pro Tyr Asn Gly Asn Thr His Tyr Ala Gln Lys Leu
         50                  55                  60

Gln Gly Arg Val Thr Met Thr Thr Asp Thr Ser Thr Ser Thr Ala Asp
 65                  70                  75                  80

Met Asp Leu Arg Ser Leu Arg Ser Asp Asp Thr Ala Val Tyr Tyr Cys
                 85                  90                  95

Ala Arg Ala Ser Ala Ala His Gly Met Asp Val Trp Gly Gln Gly Thr
                100                 105                 110

Thr Val Thr Val Ser Ser
            115
```

```
-continued

<210> SEQ ID NO 18
<211> LENGTH: 5
<212> TYPE: PRT
<213> ORGANISM: HOMO SAPIENS

<400> SEQUENCE: 18

Ser Tyr Gly Leu Ser
1               5

<210> SEQ ID NO 19
<211> LENGTH: 17
<212> TYPE: PRT
<213> ORGANISM: HOMO SAPIENS

<400> SEQUENCE: 19

Trp Ile Ser Pro Tyr Asn Gly Asn Thr His Tyr Ala Gln Lys Leu Gln
1               5                   10                  15

Gly

<210> SEQ ID NO 20
<211> LENGTH: 9
<212> TYPE: PRT
<213> ORGANISM: HOMO SAPIENS

<400> SEQUENCE: 20

Ala Ser Ala Ala His Gly Met Asp Val
1               5

<210> SEQ ID NO 21
<211> LENGTH: 108
<212> TYPE: PRT
<213> ORGANISM: HOMO SAPIENS

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg
            100                 105

<210> SEQ ID NO 22
<211> LENGTH: 11
<212> TYPE: PRT
<213> ORGANISM: HOMO SAPIENS

<400> SEQUENCE: 22

Arg Ala Ser Gln Gly Ile Ser Ser Trp Leu Ala
1               5                   10

<210> SEQ ID NO 23
<211> LENGTH: 7
<212> TYPE: PRT
<213> ORGANISM: HOMO SAPIENS
```

```
<400> SEQUENCE: 23

Ala Ala Ser Ser Leu Gln Ser
1               5

<210> SEQ ID NO 24
<211> LENGTH: 9
<212> TYPE: PRT
<213> ORGANISM: HOMO SAPIENS

<400> SEQUENCE: 24

Gln Gln Tyr Asn Ser Tyr Pro Tyr Thr
1               5

<210> SEQ ID NO 25
<211> LENGTH: 118
<212> TYPE: PRT
<213> ORGANISM: HOMO SAPIENS

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ser Pro Tyr Asn Gly Asn Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Asp Ser Ala Ala His Gly Met Asp Val Trp Gly Gln Gly Thr
            100                 105                 110

Thr Val Thr Val Ser Ser
        115

<210> SEQ ID NO 26
<211> LENGTH: 5
<212> TYPE: PRT
<213> ORGANISM: HOMO SAPIENS

<400> SEQUENCE: 26

Ser Tyr Gly Leu Ser
1               5

<210> SEQ ID NO 27
<211> LENGTH: 17
<212> TYPE: PRT
<213> ORGANISM: HOMO SAPIENS

<400> SEQUENCE: 27

Trp Ile Ser Pro Tyr Asn Gly Asn Thr His Tyr Ala Gln Lys Leu Gln
1               5                   10                  15

Gly

<210> SEQ ID NO 28
<211> LENGTH: 9
<212> TYPE: PRT
<213> ORGANISM: HOMO SAPIENS
```

```
<400> SEQUENCE: 28

Asp Ser Ala Ala His Gly Met Asp Val
1               5

<210> SEQ ID NO 29
<211> LENGTH: 108
<212> TYPE: PRT
<213> ORGANISM: HOMO SAPIENS

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg
            100                 105

<210> SEQ ID NO 30
<211> LENGTH: 11
<212> TYPE: PRT
<213> ORGANISM: HOMO SAPIENS

<400> SEQUENCE: 30

Arg Ala Ser Gln Gly Ile Ser Ser Trp Leu Ala
1               5                   10

<210> SEQ ID NO 31
<211> LENGTH: 7
<212> TYPE: PRT
<213> ORGANISM: HOMO SAPIENS

<400> SEQUENCE: 31

Ala Ala Ser Ser Leu Gln Ser
1               5

<210> SEQ ID NO 32
<211> LENGTH: 9
<212> TYPE: PRT
<213> ORGANISM: HOMO SAPIENS

<400> SEQUENCE: 32

Gln Gln Tyr Asn Ser Tyr Pro Tyr Thr
1               5

<210> SEQ ID NO 33
<211> LENGTH: 118
<212> TYPE: PRT
<213> ORGANISM: HOMO SAPIENS

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30
Gly Leu Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Asp Ser Ala Ala His Gly Met Asp Val Trp Gly Gln Gly Thr
            100                 105                 110

Thr Val Thr Val Ser Ser
        115

<210> SEQ ID NO 34
<211> LENGTH: 5
<212> TYPE: PRT
<213> ORGANISM: HOMO SAPIENS

<400> SEQUENCE: 34

Ser Tyr Gly Leu Ser
1               5

<210> SEQ ID NO 35
<211> LENGTH: 17
<212> TYPE: PRT
<213> ORGANISM: HOMO SAPIENS

<400> SEQUENCE: 35

Trp Ile Ser Ala Tyr Asn Gly Asn Thr Asn Tyr Ala Gln Lys Leu Gln
1               5                   10                  15

Gly

<210> SEQ ID NO 36
<211> LENGTH: 9
<212> TYPE: PRT
<213> ORGANISM: HOMO SAPIENS

<400> SEQUENCE: 36

Asp Ser Ala Ala His Gly Met Asp Val
1               5

<210> SEQ ID NO 37
<211> LENGTH: 108
<212> TYPE: PRT
<213> ORGANISM: HOMO SAPIENS

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
```

```
                    85                  90                  95
Thr Phe Gly Gln Gly Thr Lys Leu Glu Ile Lys Arg
                100                 105

<210> SEQ ID NO 38
<211> LENGTH: 11
<212> TYPE: PRT
<213> ORGANISM: HOMO SAPIENS

<400> SEQUENCE: 38

Arg Ala Ser Gln Gly Ile Ser Ser Trp Leu Ala
1               5                   10

<210> SEQ ID NO 39
<211> LENGTH: 7
<212> TYPE: PRT
<213> ORGANISM: HOMO SAPIENS

<400> SEQUENCE: 39

Ala Ala Ser Ser Leu Gln Ser
1               5

<210> SEQ ID NO 40
<211> LENGTH: 9
<212> TYPE: PRT
<213> ORGANISM: HOMO SAPIENS

<400> SEQUENCE: 40

Gln Gln Tyr Asn Ser Tyr Pro Tyr Thr
1               5

<210> SEQ ID NO 41
<211> LENGTH: 118
<212> TYPE: PRT
<213> ORGANISM: HOMO SAPIENS

<400> SEQUENCE: 41

Gln Val Gln Val Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Lys Tyr Ala Gln Lys Leu
        50                  55                  60

Gln Gly Arg Leu Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ala Ala His Gly Met Asp Val Trp Gly Gln Gly Thr
                100                 105                 110

Thr Val Ser Val Ser Ser
            115

<210> SEQ ID NO 42
<211> LENGTH: 5
<212> TYPE: PRT
<213> ORGANISM: HOMO SAPIENS

<400> SEQUENCE: 42

Ser Tyr Gly Ile Ser
1               5
```

```
<210> SEQ ID NO 43
<211> LENGTH: 17
<212> TYPE: PRT
<213> ORGANISM: HOMO SAPIENS

<400> SEQUENCE: 43

Trp Ile Ser Ala Tyr Asn Gly Asn Thr Lys Tyr Ala Gln Lys Leu Gln
1               5                   10                  15

Gly

<210> SEQ ID NO 44
<211> LENGTH: 9
<212> TYPE: PRT
<213> ORGANISM: HOMO SAPIENS

<400> SEQUENCE: 44

Asp Ser Ala Ala His Gly Met Asp Val
1               5

<210> SEQ ID NO 45
<211> LENGTH: 117
<212> TYPE: PRT
<213> ORGANISM: HOMO SAPIENS

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Val Met Ser Trp Val Arg Gln Ala Pro Gly Lys Gly Leu Glu Trp Val
        35                  40                  45

Ser Gly Ile Ser Gly Ser Gly Gly Asn Thr Asp His Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Ser Gly Gly Leu Phe Asp Tyr Trp Gly Leu Gly Thr Leu
            100                 105                 110

Val Thr Val Ser Ser
        115

<210> SEQ ID NO 46
<211> LENGTH: 5
<212> TYPE: PRT
<213> ORGANISM: HOMO SAPIENS

<400> SEQUENCE: 46

Asn Phe Val Met Ser
1               5

<210> SEQ ID NO 47
<211> LENGTH: 17
<212> TYPE: PRT
<213> ORGANISM: HOMO SAPIENS

<400> SEQUENCE: 47

Gly Ile Ser Gly Ser Gly Gly Asn Thr Asp His Ala Asp Ser Val Lys
1               5                   10                  15
```

Gly

<210> SEQ ID NO 48
<211> LENGTH: 8
<212> TYPE: PRT
<213> ORGANISM: HOMO SAPIENS

<400> SEQUENCE: 48

Asp Ser Gly Gly Leu Phe Asp Tyr
1               5

<210> SEQ ID NO 49
<211> LENGTH: 109
<212> TYPE: PRT
<213> ORGANISM: HOMO SAPIENS

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Arg Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro His
                85                  90                  95

Leu Thr Phe Gly Gly Gly Thr Lys Val Glu Ile Lys Arg
            100                 105

<210> SEQ ID NO 50
<211> LENGTH: 11
<212> TYPE: PRT
<213> ORGANISM: HOMO SAPIENS

<400> SEQUENCE: 50

Arg Ala Ser Gln Ser Val Ser Ser Tyr Leu Ala
1               5                   10

<210> SEQ ID NO 51
<211> LENGTH: 7
<212> TYPE: PRT
<213> ORGANISM: HOMO SAPIENS

<400> SEQUENCE: 51

Asp Ala Ser Asn Arg Ala Thr
1               5

<210> SEQ ID NO 52
<211> LENGTH: 10
<212> TYPE: PRT
<213> ORGANISM: HOMO SAPIENS

<400> SEQUENCE: 52

Gln Gln Arg Ser Asn Trp Pro His Leu Thr
1               5                   10

<210> SEQ ID NO 53
<211> LENGTH: 119

<212> TYPE: PRT
<213> ORGANISM: HOMO SAPIENS

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ser Ile Ile Glu Thr Phe Asp Tyr Trp Gly Gln Gly
            100                 105                 110

Thr Leu Val Thr Val Ser Ser
        115

<210> SEQ ID NO 54
<211> LENGTH: 5
<212> TYPE: PRT
<213> ORGANISM: HOMO SAPIENS

<400> SEQUENCE: 54

Thr Tyr Gly Met His
1               5

<210> SEQ ID NO 55
<211> LENGTH: 17
<212> TYPE: PRT
<213> ORGANISM: HOMO SAPIENS

<400> SEQUENCE: 55

Val Ile Ser His Asp Gly Ser Asp Lys Tyr Tyr Ala Asp Ser Val Lys
1               5                   10                  15

Gly

<210> SEQ ID NO 56
<211> LENGTH: 10
<212> TYPE: PRT
<213> ORGANISM: HOMO SAPIENS

<400> SEQUENCE: 56

Asp Gln Ser Ile Ile Glu Thr Phe Asp Tyr
1               5                   10

<210> SEQ ID NO 57
<211> LENGTH: 108
<212> TYPE: PRT
<213> ORGANISM: HOMO SAPIENS

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                35                  40                  45
Tyr Asp Ala Ser Asn Arg Ala Thr Gly Ile Pro Ala Arg Phe Ser Gly
     50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Gly Phe
                 85                  90                  95
Thr Phe Gly Pro Gly Thr Lys Val Asp Ile Lys Arg
            100                 105
```

<210> SEQ ID NO 58
<211> LENGTH: 11
<212> TYPE: PRT
<213> ORGANISM: HOMO SAPIENS

<400> SEQUENCE: 58

```
Arg Ala Ser Gln Ser Val Ser Ser Tyr Leu Ala
 1               5                  10
```

<210> SEQ ID NO 59
<211> LENGTH: 7
<212> TYPE: PRT
<213> ORGANISM: HOMO SAPIENS

<400> SEQUENCE: 59

```
Asp Ala Ser Asn Arg Ala Thr
 1               5
```

<210> SEQ ID NO 60
<211> LENGTH: 9
<212> TYPE: PRT
<213> ORGANISM: HOMO SAPIENS

<400> SEQUENCE: 60

```
Gln Gln Arg Ser Asn Trp Gly Phe Thr
 1               5
```

<210> SEQ ID NO 61
<211> LENGTH: 118
<212> TYPE: PRT
<213> ORGANISM: HOMO SAPIENS

<400> SEQUENCE: 61

```
Gln Val Gln Leu Val Glu Ser Gly Gly Val Val Gln Pro Gly Arg
 1               5                  10                  15
Ser Leu Arg Leu Ser Cys Ala Val Ser Gly Phe Thr Phe Arg Ser Tyr
             20                  25                  30
Gly Met His Trp Val Arg Gln Ala Pro Gly Lys Gly Leu Glu Trp Val
         35                  40                  45
Ala Val Ile Trp Tyr Asp Gly Ser Ile Lys Tyr Tyr Ala Asp Ser Val
     50                  55                  60
Lys Gly Arg Phe Thr Ile Ser Arg Asp Asn Lys Asn Thr Leu Tyr
 65                  70                  75                  80
Leu Gln Met Asn Ser Leu Arg Ala Glu Asp Thr Ala Val Tyr Phe Cys
                 85                  90                  95
Ala Arg Glu Gly Gly Arg Asp Ala Phe Asp Ile Trp Gly Gln Gly Thr
            100                 105                 110
Met Val Thr Val Ser Ser
            115
```

```
<210> SEQ ID NO 62
<211> LENGTH: 5
<212> TYPE: PRT
<213> ORGANISM: HOMO SAPIENS

<400> SEQUENCE: 62

Ser Tyr Gly Met His
1               5

<210> SEQ ID NO 63
<211> LENGTH: 17
<212> TYPE: PRT
<213> ORGANISM: HOMO SAPIENS

<400> SEQUENCE: 63

Val Ile Trp Tyr Asp Gly Ser Ile Lys Tyr Tyr Ala Asp Ser Val Lys
1               5                   10                  15

Gly

<210> SEQ ID NO 64
<211> LENGTH: 9
<212> TYPE: PRT
<213> ORGANISM: HOMO SAPIENS

<400> SEQUENCE: 64

Glu Gly Gly Arg Asp Ala Phe Asp Ile
1               5

<210> SEQ ID NO 65
<211> LENGTH: 108
<212> TYPE: PRT
<213> ORGANISM: HOMO SAPIENS

<400> SEQUENCE: 65

Ala Val Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Cys Cys Gln Gln Phe Asn Ser Tyr Pro His
                85                  90                  95

Thr Phe Gly Gly Gly Thr Lys Val Glu Ile Lys Arg
            100                 105

<210> SEQ ID NO 66
<211> LENGTH: 11
<212> TYPE: PRT
<213> ORGANISM: HOMO SAPIENS

<400> SEQUENCE: 66

Arg Ala Ser Gln Gly Ile Ser Ser Ala Leu Ala
1               5                   10

<210> SEQ ID NO 67
<211> LENGTH: 7
<212> TYPE: PRT
```

<213> ORGANISM: HOMO SAPIENS

<400> SEQUENCE: 67

Asp Ala Ser Ser Leu Glu Ser
1               5

<210> SEQ ID NO 68
<211> LENGTH: 9
<212> TYPE: PRT
<213> ORGANISM: HOMO SAPIENS

<400> SEQUENCE: 68

Gln Gln Phe Asn Ser Tyr Pro His Thr
1               5

<210> SEQ ID NO 69
<211> LENGTH: 118
<212> TYPE: PRT
<213> ORGANISM: HOMO SAPIENS

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ile Ala Val Ala Leu Phe Asp Tyr Trp Gly Gln Gly Thr
            100                 105                 110

Leu Val Thr Val Ser Ser
        115

<210> SEQ ID NO 70
<211> LENGTH: 5
<212> TYPE: PRT
<213> ORGANISM: HOMO SAPIENS

<400> SEQUENCE: 70

Ser Tyr Ala Met Ser
1               5

<210> SEQ ID NO 71
<211> LENGTH: 17
<212> TYPE: PRT
<213> ORGANISM: HOMO SAPIENS

<400> SEQUENCE: 71

Ala Ile Ser Asp Ser Gly Gly Ser Thr Tyr Tyr Ala Asp Ser Val Lys
1               5                   10                  15

Gly

<210> SEQ ID NO 72
<211> LENGTH: 9
<212> TYPE: PRT
<213> ORGANISM: HOMO SAPIENS

```
<400> SEQUENCE: 72

Glu Ile Ala Val Ala Leu Phe Asp Tyr
1               5

<210> SEQ ID NO 73
<211> LENGTH: 109
<212> TYPE: PRT
<213> ORGANISM: HOMO SAPIENS

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Pro
                85                  90                  95

Tyr Thr Phe Gly Gln Gly Thr Lys Leu Glu Ile Lys Arg
            100                 105

<210> SEQ ID NO 74
<211> LENGTH: 11
<212> TYPE: PRT
<213> ORGANISM: HOMO SAPIENS

<400> SEQUENCE: 74

Arg Ala Ser Gln Ser Val Ser Ser Tyr Leu Ala
1               5                   10

<210> SEQ ID NO 75
<211> LENGTH: 7
<212> TYPE: PRT
<213> ORGANISM: HOMO SAPIENS

<400> SEQUENCE: 75

Asp Ala Ser Asn Arg Ala Thr
1               5

<210> SEQ ID NO 76
<211> LENGTH: 10
<212> TYPE: PRT
<213> ORGANISM: HOMO SAPIENS

<400> SEQUENCE: 76

Gln Gln Arg Ser Ser Trp Pro Pro Tyr Thr
1               5                   10

<210> SEQ ID NO 77
<211> LENGTH: 5
<212> TYPE: PRT
<213> ORGANISM: Homo sapiens
<220> FEATURE:
<221> NAME/KEY: PEPTIDE
<222> LOCATION: (1)..(5)
<223> OTHER INFORMATION: Xaa is Leu or Ile
```

```
<220> FEATURE:
<221> NAME/KEY: misc_feature
<222> LOCATION: (4)..(4)
<223> OTHER INFORMATION: Xaa is Leu or Ile

<400> SEQUENCE: 77

Ser Tyr Gly Xaa Ser
1               5

<210> SEQ ID NO 78
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Xaa in position 4 is Ala or Pro, Xaa in
      position 10 is His, Asn or Lys
<220> FEATURE:
<221> NAME/KEY: misc_feature
<222> LOCATION: (4)..(4)
<223> OTHER INFORMATION: Xaa is Ala or Pro
<220> FEATURE:
<221> NAME/KEY: misc_feature
<222> LOCATION: (10)..(10)
<223> OTHER INFORMATION: Xaa is His, Asn or Lys

<400> SEQUENCE: 78

Trp Ile Ser Xaa Tyr Asn Gly Asn Thr Xaa Tyr Ala Gln Lys Leu Gln
1               5                   10                  15

Gly

<210> SEQ ID NO 79
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Xaa is Ala or Asp
<220> FEATURE:
<221> NAME/KEY: misc_feature
<222> LOCATION: (1)..(1)
<223> OTHER INFORMATION: Xaa is Ala or Asp

<400> SEQUENCE: 79

Xaa Ser Ala Ala His Gly Met Asp Val
1               5
```

MONOCLONAL ANTIBODIES AGAINST CD32B

CROSS-REFERENCE TO RELATED APPLICATIONS

This application is a divisional of U.S. patent application Ser. No. 12/811,637, filed Nov. 4, 2010, which is a 35 U.S.C. §371 national stage filing of PCT Application No. PCT/DK2008/050335, filed on Dec. 19, 2008, which claims priority to, and the benefit of, Denmark Patent Application No. PA 2008 0006 filed on Jan. 3, 2008 and U.S. Patent Application No. 61/009,877 filed on Jan. 3, 2008. The contents of the aforementioned applications are hereby incorporated by reference.

FIELD OF THE INVENTION

The present invention relates to antibodies directed to CD32b (also known as FcγRIIB), in particular to human CD32b, and uses of such antibodies, in particular their use in the treatment of cancer.

BACKGROUND OF THE INVENTION

B cell malignancies or neoplasms may arise in all lymphoid tissues where B cells are normally being produced. Most patients with B cell neoplasms are initially diagnosed with disease involving bone marrow or lymph nodes. In the case of bone marrow involvement, the transformed B cells frequently circulate through the blood and become widely disseminated throughout peripheral lymphoid tissues. However, B cell malignancies may also arise in some nonlymphoid tissues such as the thyroid, gastrointestinal tract, salivary glands and conjunctiva.

Well known B-cell-derived malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related NHL. B-cell malignancies comprise more than 85% of diagnosed lymphomas.

CD32b is an example of an antigen expressed on such malignant cells, and recent studies have identified CD32b as a potential immunotherapeutic target for B-cell malignancies (Rankin et al. (2006) Blood 108: 2384-2391). CD32b is an integral membrane glycoprotein and is the predominant Fc receptor (FcR) (Amigorena et al. (1992) Science 256: 1808-1812; Takai (2002) Nat. Rev. Immunol 2:580-592. The CD32b gene is expressed on B lymphocytes and its extracellular domain is 96% identical to CD32a (also known as FcγRIIA). CD32a is highly expressed by myeloid cells and is absent in B cells (Takai (2002) Nat. Rev. Immunol 2:580-592; Ravetch et al. (2001) Annu. Rev. Immunol. 19:275-290), and they bind IgG complexes in an indistinguishable manner but create two functionally heterogeneous responses to receptor ligation. The fundamental difference is that the A isoform initiates intracellular signaling leading to cell activation such as phagocytosis and respiratory burst, whereas the B isoform initiates inhibitory signals, e.g. inhibiting B-cell activation. CD32b is expressed in two isoforms (CD32b1 and CD32b2) that share the same extracellular and transmembrane domains but differ slightly in the intracellular domain. CD32b1 has an insertion in the intracellular part that prevents internalization of the receptor. The CD32b1 isoform is expressed preferentially on B cells whereas myeloid cells preferentially express the CD32b2 isoform (Daeron (1997), Ann Rev Imm: 203-234).

Accordingly, the identification and generation of monoclonal antibodies specific for human CD32b is essential for novel treatments based on therapeutic antibodies, including monoclonal antibody treatment of B-cell lymphoproliferative disorders. Such identification and generation has been hindered by the homology of CD32A to CD32b within the extracellular region (Brooks et al. (1989) J. Exp. Med. 170:1369-1385).

Anti-CD32b monoclonal antibodies with apparently no or very little interaction with CD32a have been reported (WO2006/066078), but need remains for new, effective anti-CD32b monoclonal antibodies for use in therapy, in particular for use in cancer therapy. In this context at least the following four areas of therapeutic application of monoclonal antibodies are anticipated: (1) the use of monoclonal antibodies as single agents in cancer therapy; (2) the use of monoclonal antibodies in combination with other therapy, such as chemotherapy to enhance antitumor responses; (3) the use of agents coupled to monoclonal antibodies as radioimmunoconjugates and immunotoxins; (4) the use of monoclonal anti-CD32b antibodies as an adjuvants, i.e. by boosting an immune response through blocking of the inhibitory effects of CD32b.

SUMMARY OF THE INVENTION

It is an object of the present invention to provide novel highly specific and effective anti-CD32b antibodies for medical use. The antibodies of the invention exhibit CD32b binding characteristics that differ from the antibodies described in the art.

Accordingly, in a first aspect, the invention relates to a monoclonal anti-CD32b antibody which does not compete with immobilised antibody 2B6 for binding to the extracellular domain of CD32b in the assay described in Example 14.

In another main aspect, the invention relates to a monoclonal anti-CD32b antibody comprising a VH CDR3 region having:
a) the sequence as set forth in
 SEQ ID No: 64,
 SEQ ID No: 79,
 SEQ ID No: 4,
 SEQ ID No: 48,
 SEQ ID No: 56, or
 SEQ ID No: 72
or
b) a variant of any of said sequences, such as a variant having at most 1, 2 or 3 amino-acid modifications, preferably substitutions, such as conservative substitutions.

In a further main aspect, the invention relates to a monoclonal anti-CD32b antibody which binds to CD32b1 with a lower apparent affinity compared to CD32b2, wherein the apparent affinity ratio ($EC_{50}$ (CD32b1)/$EC_{50}$ (CD32b2)) is below 0.75.

In a further main aspect, the invention relates to a monoclonal anti-CD32b antibody comprising a variable region which allows the antibody to compete with ligand binding to the extracellular domain of CD32b, but wherein a Fab fragment of said antibody does not completely inhibit ligand binding even in the presence of large excess of Fab fragment relative to the amount of ligand.

The anti-CD32b antibodies of the invention may be used for a number of purposes. In particular, the antibodies of the invention may be used for the treatment of various forms of cancer. Furthermore, in some embodiments, anti-CD32b antibodies of the invention can boost an immune response through blocking of the inhibitory effects of CD32b. Thus, the anti-CD32b antibodies of the invention, in particular effector-function-deficient anti-CD32b antibodies, such as monovalent anti-CD32b antibodies, may be used a stimulator of the immune system, e.g. in combination with a therapeutic antibody which acts via activation of Fc receptors, or in combination with vaccination.

BRIEF DESCRIPTION OF THE DRAWINGS

FIG. 12 shows variable region sequences.

DETAILED DESCRIPTION OF THE INVENTION

Figure 1A:
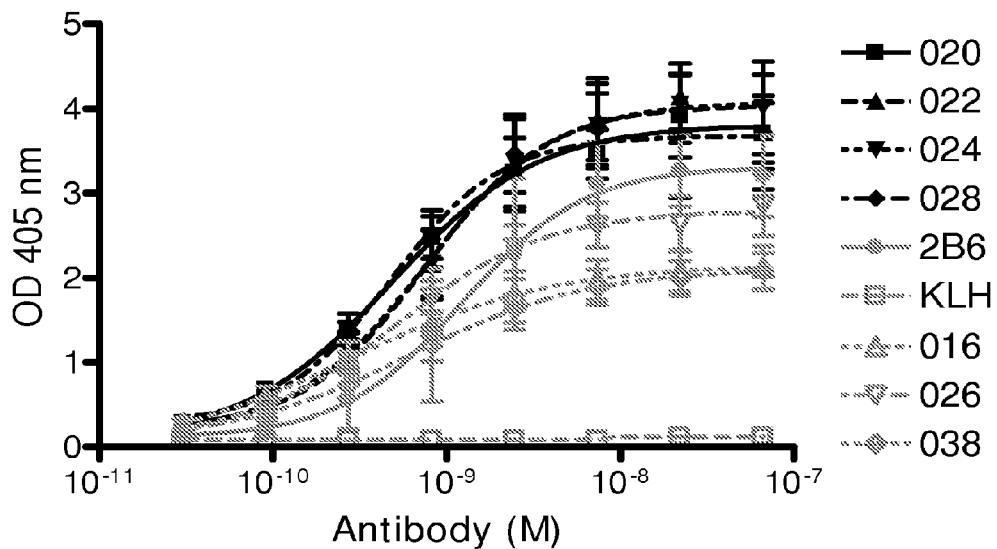
FIGS. 1A and 1B show the binding of anti-CD32b antibodies to (FIG. 1A) CD32bECDHis and (FIG. 1B) CD32aECDHis as measured by ELISA.

The terms "CD32b" and "CD32b antigen" are used interchangeably herein, and, unless specified otherwise, include any variants, isoforms and species homologs of human CD32b which are naturally expressed by cells or are expressed on cells transfected with the CD32b gene. However, these terms do not include CD32A.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as Clq, the first component in the classical pathway of complement activation. An anti-CD32b antibody may also be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of CD32b. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

An "anti-CD32b antibody" is an antibody as described above, which binds specifically to the antigen CD32b.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

In a preferred embodiment, the antibody of the invention is isolated. An "isolated antibody," as used herein, is intended to refer to an antibody which is substantially free of other antibodies having different antigenic specificities (for instance an isolated antibody that specifically binds to CD32b is substantially free of antibodies that specifically bind antigens other than CD32b). An isolated antibody that specifically binds to an epitope, isoform or variant of human CD32b may, however, have cross-reactivity to other related antigens, for instance from other species (such as CD32b species homologs). Moreover, an isolated antibody may be substantially free of other cellular material and/or chemicals. In one embodiment of the present invention, a combination of "isolated" monoclonal antibodies having different specificities are combined in a well-defined composition.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" (sec$^{-1}$), as used herein, refers to the dissociation rate constant of a particular antibody-antigen interaction. Said value is also referred to as the $k_{off}$ value.

The term "$k_a$" (M$^{-1}$×sec$^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" (M$^{-1}$), as used herein, refers to the association equilibrium constant of a particular antibody-antigen interaction and is obtained by dividing the $k_a$ by the $k_d$.

The present invention also provides antibodies comprising functional variants of the $V_L$ region, $V_H$ region, or one or more CDRs of the antibodies of the examples. A functional variant of a $V_L$, $V_H$, or CDR used in the context of an anti-CD32b antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-CD32b antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

| Amino acid residue classes for conservative substitutions | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 65-99%) retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

Examples of other functional properties of antibodies, which may be altered or retained in variant anti-CD32b antibodies of the present invention as compared to the antibodies of the examples, are:
(1) high affinity binding to CD32b;
(2) binding to transfected cells, e.g. CHO or HEK293 cells expressing CD32b;
(3) induction of CDC;
(4) induction of ADCC.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 5, for instance no more than 4, 3, 2, or 1 amino acid difference from the amino acid sequence encoded by the germline immunoglobulin gene.

As used herein, the term "inhibits growth" (e.g. referring to cells, such as tumor cells) is intended to include any measurable decrease in the cell growth when contacted with an anti-CD32b antibody as compared to the growth of the same cells not in contact with an anti-CD32b antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. effector cell phagocytosis, ADCC, CDC, and/or apoptosis.

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell. The term "bispecific antibody" is intended to include any anti-CD32b antibody, which is a bispecific molecule. The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see for instance Holliger, P. et al., PNAS USA 90, 6444-6448 (1993), Poljak, R. J. et al., Structure 2, 1121-1123 (1994)).

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4.

The term "monovalent antibody" means in the context of the present invention that an antibody molecule is capable of binding a single molecule of the antigen, and thus is not able of antigen crosslinking.

The term "stabilized IgG4 antibody" refers to an IgG4 antibody which has been modified to reduce half-molecule exchange (see van der Neut Kolfschoten M et al. (2007) Science 14; 317(5844) and references therein.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK293 cells, NS/0 cells, and lymphocytic cells.

The term "transfectoma", as used herein, includes recombinant eukaryotic host cells expressing the antibody, such as CHO cells, NS/0 cells, HEK293 cells, plant cells, or fungi, including yeast cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD32b antibodies when immunized with CD32b antigen and/or cells expressing CD32b. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The terms "B-cell neoplasms" or "mature B-cell neoplasms" in the context of the present invention include small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an anti-CD32b antibody may vary according to factors such as the disease state, age, sex, and weight of the individual, and the ability of the anti-CD32b antibody to elicit a desired response in the individual. A therapeutically effective amount is also one in which any toxic or detrimental effects of the antibody or antibody portion are outweighed by the therapeutically beneficial effects.

An "anti-idiotypic" (Id) antibody is an antibody which recognizes unique determinants generally associated with the antigen-binding site of an antibody.

In a first main aspect, the invention relates to a monoclonal anti-CD32b antibody which does not compete with immobilised antibody 2B6 for binding to the extracellular domain of CD32b in the assay described in Example 14.

In one embodiment hereof, said antibody furthermore does not compete with 2B6 in the assay described in Example 14 when said antibody is immobilised instead and competition is performed with 2B6 in fluid phase.

In a further main aspect, the invention relates to a monoclonal anti-CD32b antibody comprising a variable region which allows the antibody to compete with ligand binding to the extracellular domain of CD32b, but wherein a Fab fragment of said antibody does not completely inhibit ligand binding even in the presence of large excess of Fab fragment relative to the amount of ligand.

Figure 4:
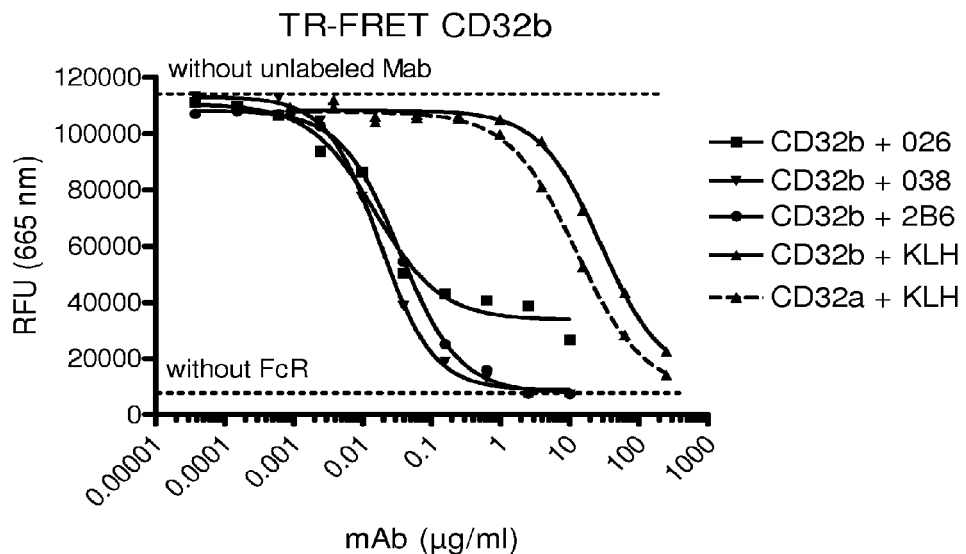
FIG. 4 shows CD32b TR-FRET based binding competition data. Maximum TR-FRET fluorescence was determined in a sample without unlabeled mAb (no competition with labeled mAb). Background fluorescence was determined in a sample without CD32bECDHis and CD32aECDHis. Inhibition of a-KLH-AlexaFluor 647 binding to CD32bECDHis and CD32aECDHis is expressed by the $IC_{50}$ value (Table 6). Data for antibody 026 is illustrative for antibodies 020, 022, 024, 028, 053, and 063.

This property is illustrated in Example 16 and FIG. 4 herein below. Example 16 describes a competition experiment in which the anti-CD32b antibodies compete with ligand for CD32b binding. As can be seen for antibody 026 in FIG. 4, upon increasing concentrations of antibody 026, initially, a plateau value of inhibition of ligand binding is reached (this is not seen for 2B6). Without being bound by any specific theory, it is believed that this plateau represents the maximal inhibition that can be obtained via the variable region, i.e. via the antigen binding site contained within the antibody. Upon further increase of antibody concentration, the ligand binding is further inhibited below the initial plateau. It is believed that this further inhibition represents inhibition of ligand binding to CD32b via the Fc fragment of the antibody, i.e. an inhibition which is independent of the variable region of the antibody.

Thus, a Fab fragment of, e.g., antibody 026 would not completely inhibit ligand binding even in the presence of large excess of Fab fragment relative to the amount of ligand.

In one embodiment, the antibody induces between 20 and 90%, such as between 25 and 80%, e.g. between 40 and 80% inhibition of ligand binding at antibody concentrations in the range of 0.1-1 µg/ml in the assay described in Example 16.

In an even further main aspect, the present invention relates to an isolated monoclonal anti-CD32b antibody which comprises a VH CDR3 sequence as set forth in a sequence selected from the group consisting of SEQ ID NO:4, 48, 56, 64, 72 and 79 or a variant of any of said sequences, such as a variant having at most 1, 2 or 3 amino-acid modifications, preferably substitutions, such as conservative substitutions.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against CD32b may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, 1 et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques.

Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In one embodiment, the antibody of the invention is an antibody which binds to the extracellular domain (ECD) of CD32b preferably with an apparent affinity ($EC_{50}$) of 10 nM or less, e.g. 5 nM or less, such as 2 nM or less, e.g. 1 nM or less, as determined by the ELISA method described in Example 10 of the description.

In a further embodiment, the antibody of the invention is an antibody which binds to mammalian cells expressing CD32b, such as IIA1.6 cells transfected with a construct encoding CD32b, preferably with an apparent affinity ($EC_{50}$) of 10 nM or less, e.g. 5 nM or less, such as 2 nM or less, e.g. 1 nM or less as determined by the method described in Example 12 of the description.

In a further embodiment, the antibody of the invention is an antibody which binds to mammalian cells expressing CD32b, such as Daudi cells, preferably with an apparent affinity ($EC_{50}$) of 10 nM or less, e.g. 5 nM or less, such as 2 nM or less, e.g. 1 nM or less as determined by the method described in Example 12 of the description.

In a further embodiment, the antibody of the invention does not bind to CD32a or displays a binding to CD32a which gives MFIs which are at least 3-4 fold lower than for binding to CD32b as determined by the method described in Example 12 of the description.

In a further embodiment, the antibody of the invention binds to CD32b1 with a lower apparent affinity compared to CD32b2, wherein the apparent affinity ratio ($EC_{50}$ (CD32b1)/$EC_{50}$ (CD32b2)) is below 0.75. In a further embodiment, the apparent affinity ratio ($EC_{50}$ (CD32b1)/$EC_{50}$ (CD32b2)) is below 0.5. In a further embodiment, the apparent affinity ratio ($EC_{50}$ (CD32b1)/$EC_{50}$ (CD32b2)) is below 0.3. In a further embodiment, the apparent affinity ratio ($EC_{50}$ (CD32b1)/$EC_{50}$ (CD32b2)) is below 0.2. In a further embodiment, the apparent affinity ratio ($EC_{50}$ (CD32b1)/$EC_{50}$ (CD32b2)) is determined by the method described in Example 21.

In a further embodiment, the antibody of the invention specifically recognizes a conformational epitope of CD32b.

In a further embodiment, the antibody of the invention is capable of inducing antibody-dependent cellular cytotoxicity (ADCC). In one embodiment, said antibody induces ADCC in Daudi cells preferably with an $EC_{50}$ value of 5 nM or less, e.g. 1 nM or less, such as 0.2 nM or less, as determined by the method described in Example 13 herein.

In another embodiment, the antibody of the invention is not capable of including ADCC.

In a further embodiment, the antibody of the invention is not capable of inducing complement-dependent cytotoxicity (CDC).

In a further embodiment, the antibody of the invention binds to human CD32b with a $K_D$ of about $10^{-8}$ M or less, preferably with a $K_D$ of about $10^{-9}$ M or less.

In a further embodiment, the antibody of the invention comprises:
a heavy chain variable region derived from a human germline $V_H$ sequence selected from the group consisting of: IGHV1-18*01, IGHV3-23*01, IGHV3-30*03 and IGHV3-33*01,
and/or
a light chain variable region derived from a human germline VK sequence selected from the group consisting of: IGKV1-13*02, IGKV3-11*01 and IGKV1D-16*01.

In a further embodiment, the antibody of the invention comprises a human heavy chain variable region (VH) CDR3 sequence comprising:
an amino acid sequence selected from the group consisting of: SEQ ID NOs:4, 12, 20, 28, 36, 44, 48, 56, 64, 72, or 79, wherein X is A or D, or
a variant of any of said sequences, wherein said variant preferably only has conservative amino-acid modifications.

In one embodiment, said variant consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 12, 20, 28, 36, 44, 48, 56, 64 and 72.

In a further embodiment, said variant has at most 1, 2 or 3 amino-acid modifications, e.g. amino-acid substitutions, preferably conservative substitutions as compared to said sequence.

In a preferred embodiment, said antibody comprises a human heavy chain variable region CDR3 sequence comprising an amino acid sequence selected from the group consisting of: SEQ ID No: 4, 12, 20, 28, 36, 44, 48, 56, 64 and 72.

In an even further embodiment, the antibody of the invention comprises:
a VH region comprising the CDR1, 2 and 3 sequences of SEQ ID NO: 2, 3 and 4; or
a VH region comprising the CDR1, 2 and 3 sequences of SEQ ID NO:10, 11 and 12; or
a VH region comprising the CDR1, 2 and 3 sequences of SEQ ID NO:18, 19 and 20; or
a VH region comprising the CDR1, 2 and 3 sequences of SEQ ID NO:26, 27, and 28; or
a VH region comprising the CDR1, 2 and 3 sequences of SEQ ID NO:34, 35 and 36; or
a VH region comprising the CDR1, 2 and 3 sequences of SEQ ID NO:42, 43 and 44; or
a VH region comprising the CDR1, 2 and 3 sequences of SEQ ID NO:46, 47 and 48; or
a VH region comprising the CDR1, 2 and 3 sequences of SEQ ID NO: 54, 55 and 56; or
a VH region comprising the CDR1, 2 and 3 sequences of SEQ ID NO: 62, 63 and 64; or
a VH region comprising the CDR1, 2 and 3 sequences of SEQ ID NO:70, 71 and 72; or
a variant of any said VH regions, wherein said variant preferably only has conservative amino-acid substitutions.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:2, 10, 18, 26, 34, 42, 46, 54, 62 and 70.

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 3, 11, 19, 27, 35, 43, 47, 55, 63 and 71.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 12, 20, 28, 36, 44, 48, 56, 64 and 72.

In another embodiment, the antibody the antibody comprises
 a) a VL CDR3 region having the sequence as set forth in SEQ ID No: 16 and a VH CDR3 region having a sequence selected from the group consisting of SEQ ID No: 12, or SEQ ID No: 20, or SEQ ID No: 28, or SEQ ID No: 36, and SEQ ID No:44
 b) a VL CDR3 region having the sequence as set forth in SEQ ID No: 8 and a VH CDR3 region having the sequence as set forth in SEQ ID No: 4
 c) a VL CDR3 region having the sequence as set forth in SEQ ID No: 52 and a VH CDR3 region having the sequence as set forth in SEQ ID No: 48
 d) a VL CDR3 region having the sequence as set forth in SEQ ID No: 60 and a VH CDR3 region having the sequence as set forth in SEQ ID No: 56
 e) a VL CDR3 region having the sequence as set forth in SEQ ID No: 68 and a VH CDR3 region having the sequence as set forth in SEQ ID No: 64,
 f) a VL CDR3 region having the sequence as set forth in SEQ ID No: 76 and a VH CDR3 region having the sequence as set forth in SEQ ID No: 72, or
 g) a variant of any of the above, wherein said variant preferably only has conservative substitutions in said sequences In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 12, 20, 28, 36, 44, 48, 56, 64 and 72.

In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 8, 16, 24, 32, 40, 52, 60, 68 and 76.

In a further embodiment, the antibody of the invention comprises:

a VH region comprising the CDR1, 2 and 3 sequences of SEQ ID NO: 2, 3 and 4 and a VL region comprising the CDR 3 sequence of SEQ ID NO: 8; or a VH region comprising the CDR1 and 2 sequences of SEQ ID NO:77 and 78 and a CDR3 of SEQ ID NO: 12 and a VL region comprising the CDR3 sequence of SEQ ID NO: 16; or a VH region comprising the CDR1 and 2 sequences of SEQ ID NO:77 and 78 and a CDR3 of SEQ ID NO:20 and a VL region comprising the CDR3 sequence of SEQ ID NO: 16; or a VH region comprising the CDR1 and 2 sequences of SEQ ID NO:77 and 78 and a CDR3 of SEQ ID NO: 28 and a VL region comprising the CDR3 sequence of SEQ ID NO: 16; or a VH region comprising the CDR1 and 2 sequences of SEQ ID NO:77 and 78 and a CDR3 of SEQ ID NO: 36 and a VL region comprising the CDR3 sequence of SEQ ID NO: 16; or a VH region comprising the CDR1, 2 and 3 sequences of SEQ ID NO: 46, 47 and 48 and a VL region comprising the CDR3 sequences of SEQ ID NO: 52; or a VH region comprising the CDR1, 2 and 3 sequences of SEQ ID NO: 54, 55 and 56 and a VL region comprising the CDR3 sequence of SEQ ID NO: 60; or a VH region comprising the CDR1, 2 and 3 sequences of SEQ ID NO: 62, 63 and 64 and a VL region comprising the CDR3 sequence of SEQ ID NO: 68; or a VH region comprising the CDR1, 2 and 3 sequences of SEQ ID NO: 70, 71 and 72 and a VL region comprising the CDR3 sequences of SEQ ID NO: 76; or a variant of any of said antibodies, wherein said variant preferably only has conservative amino-acid substitutions in said sequences.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 2, 10, 18, 26, 34, 46, 54, 62 and 70.

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:3, 11, 19, 27, 35, 47, 55, 63 and 71.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 12, 20, 28, 36, 44, 48, 56, 64 and 72.

In one embodiment, said variant comprises a VL CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:6, 14, 22, 30, 38, 50, 58, 66 and 74.

In one embodiment, said variant comprises a VL CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:7, 15, 23, 31, 39, 51, 59, 67 and 75.

In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:8, 16, 24, 32, 40, 52, 60, 68 and 76.

In a particular embodiment if X in SEQ ID No: 77 is I (Ile), then X position 4 and 10 of SEQ ID No: 78 is A (Ala) and K (Lys) respectively.

In another particular embodiment if X in SEQ ID No:77 is L (Leu) then X position 4 and 10 of SEQ ID No: 78 is either A (Ala) and N (Asn) respectively, or P (Pro) and H (His) respectively.

In a further embodiment, the antibody of the invention comprises:

a VH region comprising the CDR1, 2 and 3 sequences of SEQ ID NO: 2, 3 and 4 and a VL region comprising the CDR1, 2 and 3 sequences of SEQ ID NO:6, 7 and 8; or a VH region comprising the CDR1, 2 and 3 sequences of SEQ ID NO:10, 11 and 12 and a VL region comprising the CDR1, 2 and 3 sequences of SEQ ID NO: 14, 15 and 16; or a VH region comprising the CDR1, 2 and 3 sequences of SEQ ID NO:18, 19 and 20 and a VL region comprising the CDR1, 2 and 3 sequences of SEQ ID NO:22, 23 and 24; or a VH region comprising the CDR1, 2 and 3 sequences of SEQ ID NO:26, 27 and 28 and a VL region comprising the CDR1, 2 and 3 sequences of SEQ ID NO:30, 31 and 32; or a VH region comprising the CDR1, 2 and 3 sequences of SEQ ID NO:34, 35 and 36 and a VL region comprising the CDR1, 2 and 3 sequences of SEQ ID NO:38, 39 and 40; or a VH region comprising the CDR1, 2 and 3 sequences of SEQ ID NO:42, 43 and 44 and a light chain having a molecular mass of 23,493 Dalton, such as a light chain having a VL region comprising the CDR1, 2 and 3 sequences of SEQ ID NO:14, 15 and 16; or a VH region comprising the CDR1, 2 and 3 sequences of SEQ ID NO: 46, 47 and 48 and a VL region comprising the CDR1, 2 and 3 sequences of SEQ ID NO: 50, 51 and 52; or a VH region comprising the CDR1, 2 and 3 sequences of SEQ ID NO: 54, 55 and 56 and a VL region comprising the CDR1, 2 and 3 sequences of SEQ ID NO: 58, 59 and 60; or a VH region comprising the CDR1, 2 and 3 sequences of SEQ ID NO: 62, 63 and 64 and a VL region comprising the CDR1, 2 and 3 sequences of SEQ ID NO: 66, 67 and 68; or a VH region comprising the CDR1, 2 and 3 sequences of SEQ ID NO: 70, 71 and 72 and a VL region comprising the CDR1, 2 and 3 sequences of SEQ ID NO: 74, 75 and 76; or a variant of any of said antibodies, wherein said variant preferably only has conservative amino-acid modifications in said sequences.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 2, 10, 18, 26, 34, 46, 54, 62 and 70

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:3, 11, 19, 27, 35, 47, 55, 63 and 71.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 12, 20, 28, 36, 44, 48, 56, 64 and 72.

In one embodiment, said variant comprises a VL CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:6, 14, 22, 30, 38, 50, 58, 66 and 74.

In one embodiment, said variant comprises a VL CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:7, 15, 23, 31, 39, 51, 59, 67 and 75.

In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:8, 16, 24, 32, 40, 52, 60, 68 and 76.

In an even further embodiment, the antibody of the invention comprises:

a VH region comprising the sequence of SEQ ID NO:4 and a VL region comprising the sequence of SEQ ID NO: 8; or a VH region comprising the sequence of SEQ ID NO:12 and a VL region comprising the sequence of SEQ ID NO:16; or a VH region comprising the sequence of SEQ ID NO:20 and a VL region comprising the sequence of SEQ ID NO:16; or a VH region comprising the sequence of SEQ ID NO:28 and a VL region comprising the sequence of SEQ ID NO:16; or a VH region comprising the sequence of SEQ ID NO:36 and a VL region comprising the sequence of SEQ ID NO:16; or a VH region comprising the sequence of SEQ ID NO:48 and a VL region comprising the sequence of SEQ ID NO:52; or a VH region comprising the sequence of SEQ ID NO:56 and a VL region comprising the sequence of SEQ ID NO:60; or a VH region comprising the sequence of SEQ ID NO:64 and a VL region comprising the sequence of SEQ ID NO:68; or a VH region comprising the sequence of SEQ ID NO:72 and a VL region comprising the sequence of SEQ ID NO:76; or a variant of any of the above, wherein said variant preferably only has conservative modifications.

In one embodiment, said variant comprises a VH region which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:4, 12, 20, 28, 36, 44, 48, 56, 64 or 72.

In one embodiment, said variant comprises a VL region which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:8, 16, 52, 60, 68 or 76.

In a further embodiment the antibody of the present invention comprises a VH having at least 80% identity, such as 90%, or 95%, or 97%, or 98%, or 99% identity to a VH region sequence selected from the group consisting of: SEQ ID NO:1, 9, 17, 25, 33, 41, 45, 53, 61 and 69.

In a further embodiment the antibody of the present invention comprises a VL having at least 80% identity, such as 90%, or 95%, or 97%, or 98%, or 99% identity to a VL region sequence selected from the group consisting of: SEQ ID NO:5, 13, 21, 29, 37, 49, 57, 65 and 73.

In an even further embodiment, the antibody of the invention comprises a VH region selected from the group consisting of: SEQ ID NO:1, 9, 17, 25, 33, 41, 45, 53, 61 and 69.

In an even further embodiment, the antibody of the invention comprises a VL region selected from the group consisting of: SEQ ID NO:5, 13, 21, 29, 37, 49, 57, 65 and 73.

In an even further embodiment, the antibody of the invention comprises a VL region sequence comprising the sequence of SEQ ID NO:65, but wherein SEQ ID NO:65 the amino acid at position 87 is not cysteine. In a special embodiment, the amino acid at position 87 is selected from the group of Ala, Arg, Asn, Asp, Glu, Gln, Gly, His, Ile, Leu, Lys, Met, Phe, Pro, Ser, Thr, Trp, Tyr and Val.

In an even further embodiment, the antibody of the invention comprises:

a VH region comprising the sequence of SEQ ID NO:1 and a VL region comprising the sequence of SEQ ID NO: 5; or a VH region comprising the sequence of SEQ ID NO:9 and a VL region comprising the sequence of SEQ ID NO:13; or a VH region comprising the sequence of SEQ ID NO:17 and a VL region comprising the sequence of SEQ ID NO:21; or a VH region comprising the sequence of SEQ ID NO:25 and a VL region comprising the sequence of SEQ ID NO:29; or a VH region comprising the sequence of SEQ ID NO:33 and a VL region comprising the sequence of SEQ ID NO:37; or a VH region comprising the sequence of SEQ ID NO:41 and a VL region comprising the sequence of SEQ ID NO:21; or a VH region comprising the sequence of SEQ ID NO:45 and a VL region comprising the sequence of SEQ ID NO:49; or a VH region comprising the sequence of SEQ ID NO:53 and a VL region comprising the sequence of SEQ ID NO:57; or a VH region comprising the sequence of SEQ ID NO:61 and a VL region comprising the sequence of SEQ ID NO:65; or a VH region comprising the sequence of SEQ ID NO:73 and a VL region comprising the sequence of SEQ ID NO:73.

In an even further embodiment, the antibody of the invention comprises a VH region comprising the sequence of SEQ ID NO:61 and a VL region comprising the sequence of SEQ ID NO:65, but wherein SEQ ID NO:65 the amino acid at position 87 is not cysteine. In a special embodiment, the amino acid at position 87 is selected from the group of Ala, Arg, Asn, Asp, Glu, Gln, Gly, His, Ile, Leu, Lys, Met, Phe, Pro, Ser, Thr, Trp, Tyr and Val.

The present invention also, in one aspect, provides anti-CD32b antibodies which are characterized with respect to their ability to compete with an antibody having:

a VH region comprising the sequence of SEQ ID NO:1 and a VL region comprising the sequence of SEQ ID NO: 5; or a VH region comprising the sequence of SEQ ID NO:9 and a VL region comprising the sequence of SEQ ID NO:13; or a VH region comprising the sequence of SEQ ID NO:17 and a VL region comprising the sequence of SEQ ID NO:21; or a VH region comprising the sequence of SEQ ID NO:25 and a VL region comprising the sequence of SEQ ID NO:29; or a VH region comprising the sequence of SEQ ID NO:33 and a VL region comprising the sequence of SEQ ID NO:37; or a VH region comprising the sequence of SEQ ID NO:41 and a VL region comprising the sequence of SEQ ID NO:21; or a VH region comprising the sequence of SEQ ID NO:45 and a VL region comprising the sequence of SEQ ID NO:49; or a VH region comprising the sequence of SEQ ID NO:53 and a VL region comprising the sequence of SEQ ID NO:57; or a VH region comprising the sequence of SEQ ID NO:61 and a VL region comprising the sequence of SEQ ID NO:65; or a VH region comprising the sequence of SEQ ID NO:73 and a VL region comprising the sequence of SEQ ID NO:73.

Competition for binding to CD32b or a portion of CD32b by two or more anti-CD32b antibodies may be determined by any suitable technique. In one embodiment, competition is determined by an ELISA assay, e.g. as described in Example 14 herein.

Competition in the context of the present invention refers to any detectably significant reduction in the propensity for a particular molecule to bind a particular binding partner in the presence of another molecule that binds the binding partner. Typically, competition means an at least about 10% reduction, such as an at least about 15%, e.g. an at least about 20%, such as an at least 40% reduction in binding between an anti-CD32b antibody and a fragment of CD32b or full-length CD32b, caused by the presence of another anti-CD32b antibody as determined by, e.g., ELISA analysis using sufficient amounts of the two or more competing anti-CD32b antibodies and CD32b molecule.

Additional methods for determining binding specificity by competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993), and Muller, Meth. Enzymol. 92, 589-601 (1983)).

The present invention also relates to provides anti-CD32b antibodies which bind to the same epitope as an antibody having:

a VH region comprising the sequence of SEQ ID NO:1 and a VL region comprising the sequence of SEQ ID NO: 5; or a VH region comprising the sequence of SEQ ID NO:9 and a VL region comprising the sequence of SEQ ID NO:13; or a VH region comprising the sequence of SEQ ID NO:17 and a VL region comprising the sequence of SEQ ID NO:21; or a VH region comprising the sequence of SEQ ID NO:25 and a VL region comprising the sequence of SEQ ID NO:29; or a VH region comprising the sequence of SEQ ID NO:33 and a VL region comprising the sequence of SEQ ID NO:37; or a VH region comprising the sequence of SEQ ID NO:41 and a VL region comprising the sequence of SEQ ID NO:21; or a VH region comprising the sequence of SEQ ID NO:45 and a VL region comprising the sequence of SEQ ID NO:49; or a VH region comprising the sequence of SEQ ID NO:53 and a VL region comprising the sequence of SEQ ID NO:57; or a VH region comprising the sequence of SEQ ID NO:61 and a VL region comprising the sequence of SEQ ID NO:65; or a VH region comprising the sequence of SEQ ID NO:73 and a VL region comprising the sequence of SEQ ID NO:73.

The antibodies described in the Examples section herein are characterized in that they bind CD32b, but do not bind CD32a. or bind CD32a with very low affinity. This means that amino-acid residues that differ between CD32b and CD32a are involved in the binding of these antibodies. Since CD32b and CD32a are very similar in sequence and only display a very limited number of amino-acid differences, it is possible to identify amino-acid residues involved in binding by constructing CD32b variants in which differences between CD32b and CD32a have been eliminated and testing whether the antibodies bind such variants. Alternatively or in addition epitopes can be characterized by alanine-scanning mutagenesis, e.g. as described in Lang et al. Biochemistry 39:15674-15685 (2000) or Dall'aqua et al. Biochemistry 37:7981-7991 (1998).

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-CD32b antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In one embodiment, the antibody of the invention is a full-length antibody. In another embodiment, the antibody of the invention is an antibody fragment or a single-chain antibody.

Antibodies fragments may e.g. be obtained by fragmentation using conventional techniques, and the fragments screened for utility in the same manner as described herein for whole antibodies. For example, F(ab')$_2$ fragments may be generated by treating antibody with pepsin. The resulting F(ab')$_2$ fragment may be treated to reduce disulfide bridges to produce Fab' fragments. Fab fragments may be obtained by treating an IgG antibody with papain; Fab' fragments may be obtained with pepsin digestion of IgG antibody. A F(ab') fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating a F(ab')$_2$ fragment with a reducing agent, such as dithiothreitol. Antibody fragment may also be generated by expression of nucleic acids encoding such fragments in recombinant cells (see for instance Evans et al., J. Immunol. Meth. 184, 123-38 (1995)). For example, a chimeric gene encoding a portion of a F(abT)$_2$ fragment could include DNA sequences encoding the C$_H$1 domain and hinge region of the H chain, followed by a translational stop codon to yield such a truncated antibody fragment molecule.

In one embodiment, the anti-CD32b antibody is a monovalent antibody, preferably a monovalent antibody as described in WO2007059782 (Genmab) (incorporated herein by reference). Accordingly, in one embodiment, the antibody is a monovalent antibody, wherein said anti-CD32b antibody is constructed by a method comprising:
i) providing a nucleic acid construct encoding the light chain of said monovalent antibody, said construct comprising a nucleotide sequence encoding the VL region of a selected antigen specific anti-CD32b antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;
ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;
iii) providing a cell expression system for producing said monovalent antibody;
iv) producing said monovalent antibody by co-expressing the nucleic acid constructs of (i) and (ii) in cells of the cell expression system of (iii).

Similarly, in one embodiment, the anti-CD32b antibody is a monovalent antibody, which comprises
(i) a variable region of an antibody of the invention as described herein or an antigen binding part of the said region, and
(ii) a C$_H$ region of an immunoglobulin or a fragment thereof comprising the C$_H$2 and C$_H$3 regions, wherein the C$_H$ region or fragment thereof has been modified such that the region corresponding to the hinge region and, if the immunoglobulin is not an IgG4 subtype, other regions of the C$_H$ region, such as the C$_H$3 region, do not comprise any amino acid residues, which are capable of forming disulfide bonds with an identical C$_H$ region or other covalent or stable non-covalent inter-heavy chain bonds with an identical C$_H$ region in the presence of polyclonal human IgG.

In a further embodiment, the heavy chain of the monovalent anti-CD32b antibody has been modified such that the entire hinge has been deleted.

In a further embodiment, said monovalent antibody is of the IgG4 subtype, but the C$_H$3 region has been modified so that one or more of the following amino acid substitutions have been made: Thr (T) in position 366 has been replaced by Ala (A); Leu (L) in position 368 has been replaced by Ala (A); Leu (L) in position 368 has been replaced by Val (V); Phe (F) in position 405 has been replaced by Ala (A); Phe (F) in position 405 has been replaced by Leu (L); Tyr (Y) in position 407 has been replaced by Ala (A); Arg (R) in position 409 has been replaced by Ala (A).

In another further embodiment, the sequence of said monovalent antibody has been modified so that it does not comprise any acceptor sites for N-linked glycosylation.

Anti-CD32b antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-CD32b antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single V$_H$ and V$_L$ are used, bivalent, if two V$_H$ and V$_L$ are used, or polyvalent, if more than two V$_H$ and V$_L$ are used.

In one embodiment, the anti-CD32b antibody of the invention is an effector-function-deficient antibody. Such antibodies are particularly useful when the antibody is for use in stimulation of the immune system through blocking of the inhibitory effects of CD32b. For such applications, it may be advantages that the antibody has no effector functions, such as ADCC, as they may lead to undesired cytotoxicity.

In one embodiment, the effector-function-deficient anti-CD32b antibody is a stabilized IgG4 antibody. Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)). Preferably, said antibody comprises a Lys or Ala residue at the position corresponding to 409 or the CH3 region of the antibody has been replaced by the CH3 region of human IgG1, of human IgG2 or of human IgG3.

In a further embodiment. the stabilized IgG4 anti-CD32b antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In an even further embodiment. the stabilized IgG4 anti-CD32b antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient anti-CD32b antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24): 12161-12168 (2001).

In a further embodiment, the antibody of the invention is alpha-2,6-sialylated. Sialylation of the Fc-linked glycans may be performed in vivo by a recombinant host cell also expressing alpha-2,6-sialyltranferase (such as described by Jassal et al., Biochem Biophys Ras Commun. 286(2):243-9 (2001)). Alternatively, the alpha-2-6-sialylation may be performed in vitro such as described by Anthony et al., Science 320:373 (2008) (under In vitro glycosylation in the Supporting Online Material).

In a further embodiment. the antibody of the invention is conjugated to another moiety, such as a cytotoxic moiety, a radioisotope or a drug. Such antibodies may be produced by chemically conjugating the other moiety to the N-terminal side or C-terminal side of the anti-CD32b antibody or fragment thereof (e.g., an anti-CD32b antibody H chain, L chain, or anti-CD32b specific/selective fragment thereof) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

In general, anti-CD32b antibodies described herein may be modified by inclusion of any suitable number of such modified amino acids and/or associations with such conjugated substituents. Suitability in this context is generally determined by the ability to at least substantially retain CD32b selectivity and/or specificity associated with the non-derivatized parent anti-CD32b antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e. g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On Cd-Rom, Humana Press, Towata, N.J. The modified amino acid may for instance be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Anti-CD32b antibodies may also be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000).

In one embodiment, the present invention provides an anti-CD32b antibody that is conjugated to a second molecule that is selected from a radionuclide, an enzyme, an enzyme substrate, a cofactor, a fluorescent marker, a chemiluminescent marker, a peptide tag, or a magnetic particle. In one embodiment, an anti-CD32b antibody may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to an anti-CD32b antibody of the present invention. One example of indirect coupling of a second agent is coupling by a spacer moiety. These spacers, in turn, may be either insoluble or soluble (see for instance Diener et al., Science 231, 148 (1986)) and may be selected to enable drug release from the anti-CD32b antibody at a target site and/or under particular conditions. Additional examples of agents that may be coupled to an anti-CD32b antibody include lectins and fluorescent peptides.

In one embodiment, anti-CD32b antibodies comprising one or more radiolabeled amino acids are provided. A radiolabeled anti-CD32b antibody may be used for both diagnostic and therapeutic purposes (conjugation to radiolabeled molecules is another possible feature). Nonlimiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. RE35,500), U.S. Pat. No. 5,648,471 and U.S. Pat. No. 5,697,902. For example, a radioisotope may be conjugated by a chloramine T method.

The radiometals $^{111}$In and $^{90}$Y are, respectively, a pure γ-emitter and a pure β-emitter. Iodine-125, the most commonly used emitter of Auger electrons, has a half-life of about 60 days and frequently is released by immunoconjugates in vivo (due to dehalogenation). The most commonly considered alpha emitters for clinical use, astatine-211 and bismuth-212, have relatively short half-lives (7.2 h and 1.0 h, respectively) and decay into radioactive isotopes that may not be retained by the immunoconjugate after the first alpha emission (Wilbur, Antibiot. Immunoconjug. Radiopharm. 4, 5-97 (1991)).

Radioisotopes may be attached directly or indirectly to an anti-CD32b antibody. The radioisotopes $^{125}$I, $^{131}$I, $^{99}$Tc, $^{186}$Re and $^{188}$Re may be, for example, covalently bound to proteins (including antibodies) through amino acid functional groups. For radioactive iodine it is usually through the phenolic group found on tyrosine. There are numerous methods to accomplish this: chloramine-T (see for instance Greenwood et al., Biochem J. 89, 114-123 (1963) and Iodogen (Salacinski et al., Anal. Biochem. 117, 136-146 (1981)). Tc and Re isotopes may be covalently bound through the sulfhydryl group of cysteine (see for instance Griffiths et al., Cancer Res. 51, 4594-4602 (1991)). However, such compositions may be relatively better suited for diagnostic purposes as the body often can break these covalent bonds, releasing the radioisotopes to the circulatory system.

In one embodiment, an anti-CD32b antibody of the invention comprises a conjugated nucleic acid or nucleic acid-associated molecule. In one such facet of the present invention, the conjugated nucleic acid is a cytotoxic ribonuclease. In one embodiment, the conjugated nucleic acid is an antisense nucleic acid (for instance a S100A10 targeted antisense molecule, which may also be an independent component in a combination composition or combination administration method of the present invention—see for instance Zhang et al., J Biol Chem. 279(3), 2053-62 (2004)). In one embodiment, the conjugated nucleic acid is an inhibitory RNA molecule (e.g., a siRNA molecule). In one embodiment, the conjugated nucleic acid is an immunostimulatory nucleic acid (e.g., an immunostimulatory CpG motif-containing DNA molecule). In one embodiment, the conjugated nucleic acid is an expression cassette coding for expression of a tumor suppressor gene, anti-cancer vaccine, anti-cancer cytokine, or apoptotic agent. Such derivatives also may comprise conjugation of a nucleic acid coding for expression of one or more cytotoxic proteins, such as plant and bacterial toxins.

In one embodiment, an anti-CD32b antibody is conjugated to a functional nucleic acid molecule. Functional nucleic acids include antisense molecules, interfering nucleic acid molecules (e.g., siRNA molecules), aptamers, ribozymes, triplex forming molecules, and external guide sequences. The functional nucleic acid molecules may act as effectors, inhibitors, modulators, and stimulators of a specific activity possessed by a target molecule, or the functional nucleic acid molecules may possess a de novo activity independent of any other molecules. A representative sample of methods and techniques which aid in the design and use of antisense molecules may be found in the following non-limiting list of US patents: U.S. Pat. No. 5,135,917, U.S. Pat. No. 5,294,533, U.S. Pat. No. 5,627,158, U.S. Pat. No. 5,641,754, U.S. Pat. No. 5,691,317, U.S. Pat. No. 5,780,607, U.S. Pat. No. 5,786,138, U.S. Pat. No. 5,849,903, U.S. Pat. No. 5,856,103, U.S. Pat. No. 5,919,772, U.S. Pat. No. 5,955,590, U.S. Pat. No. 5,990,088, U.S. Pat. No. 5,994,320, U.S. Pat. No. 5,998,602, U.S. Pat. No. 6,005,095, U.S. Pat. No. 6,007,995, U.S. Pat. No. 6,013,522, U.S. Pat. No. 6,017,898, U.S. Pat. No. 6,018,042, U.S. Pat. No. 6,025,198, U.S. Pat. No. 6,033,910, U.S. Pat. No. 6,040,296, U.S. Pat. No. 6,046,004, U.S. Pat. No. 6,046,319 and U.S. Pat. No. 6,057,437.

In another embodiment, an anti-CD32b antibody of the invention is conjugated to an aptamer. Aptamers are molecules that interact with a target molecule, for instance in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Representative examples of how to make and use aptamers to bind a variety of different target molecules may be found in the following non-limiting list of US patents: U.S. Pat. No. 5,476,766, U.S. Pat. No. 5,503,978, U.S. Pat. No. 5,631,146, U.S. Pat. No. 5,731,424, U.S. Pat. No. 5,780,228, U.S. Pat. No. 5,792,613, U.S. Pat. No. 5,795,721, U.S. Pat. No. 5,846,713, U.S. Pat. No. 5,858,660, U.S. Pat. No. 5,861,254, U.S. Pat. No. 5,864,026, U.S. Pat. No. 5,869,641, U.S. Pat. No. 5,958,691, U.S. Pat. No. 6,001,988, U.S. Pat. No. 6,011,020, U.S. Pat. No. 6,013,443, U.S. Pat. No. 6,020,130, U.S. Pat. No. 6,028,186, U.S. Pat. No. 6,030,776 and U.S. Pat. No. 6,051,698.

In another embodiment, the present invention provides an anti-CD32b antibody which is conjugated to a ribozyme. Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions may be found in the following non-limiting list of US patents: U.S. Pat. No. 5,646,042, U.S. Pat. No. 5,693,535, U.S. Pat. No. 5,731,295, U.S. Pat. No. 5,811,300, U.S. Pat. No. 5,837,855, U.S. Pat. No. 5,869,253, U.S. Pat. No. 5,877,021, U.S. Pat. No. 5,877,022, U.S. Pat. No. 5,972,699, U.S. Pat. No. 5,972,704, U.S. Pat. No. 5,989,906 and U.S. Pat. No. 6,017,756.

In one embodiment, the present invention provides an anti-CD32b antibody that is conjugated to a triplex forming function nucleic acid. Such nucleic acid molecules can interact with either double-stranded or single-stranded nucleic acid. When triplex molecules interact with a target region, a structure called a triplex is formed, in which three strands of DNA form a complex dependant on both Watson-Crick and Hoogsteen base-pairing. Triplex molecules can bind target regions with high affinity and specificity. Representative examples of how to make and use triplex forming molecules to bind a variety of different target molecules may be found in the following non-limiting list of US patents: U.S. Pat. No. 5,176,996, U.S. Pat. No. 5,645,985, U.S. Pat. No. 5,650,316, U.S. Pat. No. 5,683,874, U.S. Pat. No. 5,693,773, U.S. Pat. No. 5,834,185, U.S. Pat. No. 5,869,246, U.S. Pat. No. 5,874,566 and U.S. Pat. No. 5,962,426.

In one embodiment, an anti-CD32b antibody is conjugated to an external guide sequence. External guide sequences (EGSs) are molecules that bind a target nucleic acid molecule forming a complex that is recognized by RNase P, which cleaves the target molecule. EGSs may be designed to specifically target a RNA molecule of choice. RNase P aids in processing transfer RNA (tRNA) within a cell. Bacterial RNase P may be recruited to cleave virtually any RNA sequence by using an EGS that causes the target RNA:EGS complex to mimic the natural tRNA substrate. (see for instance WO 92/03566 and Forster and Altman, Science 238, 407-409 (1990) for discussion). Representative examples of how to make and use EGS molecules to facilitate cleavage of a variety of different target molecules are provided in the following non-limiting list of US patents: U.S. Pat. No. 5,168,053, U.S. Pat. No. 5,624,824, U.S. Pat. No. 5,683,873, U.S. Pat. No. 5,728,521, U.S. Pat. No. 5,869,248 and U.S. Pat. No. 5,877,162.

In one embodiment, an anti-CD32b antibody is conjugated to an interfering nucleic acid molecule, such as a siRNA or other RNAi molecule (e.g., an inhibitory double stranded (ds) RNA molecule of about 20-25 nucleotides), which is targeted to interfere with the action of a target gene expression product, such as a gene expression product involved in a CD32b-mediated disease or condition. Methods for the production and use of interfering nucleic acid molecules are provided in for instance Nishikura, Cell. 107(4), 415-8 (2001), Fjose et al., Biotechnol Annu Rev. 7, 31-57 (2001), Hanon, Nature 418, 244-51 (2002), Brantl, Biochim Biophys Acta. 1575(1-3), 15-25 (2002), Tuschl, Chembiochem. 2(4), 239-45 (2001), Caplen, Expert Opin Biol Ther. 3(4), 575-86 (2003), Lu et al., Curr Opin Mol Ther. 5(3), 225-34 (2003), Shuey et al., Drug Discov Today. 7(20), 1040-6 (2002), Shi, Trends Genet. 19(1), 9-12 (2003), Kovar et al., Semin Cancer Biol. 13(4), 275-81 (2003), Lavrey et al., Curr Opin Drug Discov Devel. 6(4), 561-9 (2003), Clewey, Commun Dis Public Health. 6(2), 162-3 (2003), Duxbury et al., J Surg Res. 117(2), 339-44 (2004), Caplen et al., Ann N Y Acad Sci. 1002, 56-62 (2003), WO 01/75164, U.S. Pat. No. 6,506,559, US 20040086884, US 20040077574, US 20040063654, US 20040033602, US 20030167490, US 20030157030, US 20030114409, US 20030108923, US 20040014113 and US 20020132788.

Any method known in the art for conjugating the anti-CD32b antibody to the conjugated molecule(s), such as those described above, may be employed, including those methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Linkage/conjugation may be accomplished in any suitable way. For example, a covalent linkage may take the form of a disulfide bond (if necessary and suitable, an anti-CD32b antibody could be engineered to contain an extra cysteine codon, which desirably does not interfere with the CD32b binding activity of the molecule. A toxin molecule, derivatized with a sulfhydryl group reactive with the cysteine of the modified anti-CD32b antibody, may form an immunoconjugate with the anti-CD32b antibody. Alternatively, a sulfhydryl group may be introduced directly to an anti-CD32b antibody using solid phase polypeptide techniques. For example, the introduction of sulfhydryl groups into peptides is described by Hiskey, Peptides 3, 137 (1981). The introduction of sulfhydryl groups into proteins is described in Maasen et al., Eur. J. Biochem. 134, 32 (1983). Once the correct sulfhydryl groups are present, the cytotoxin and anti-CD32b antibody may be purified, both sulfur groups reduced; cytotoxin and ligand mixed (for instance in a ratio of about 1:5 to 1:20); and disulfide bond formation allowed to proceed to completion (generally about 20 to 30 minutes) at room temperature. The mixture may then be dialyzed against phosphate buffered saline or chromatographed in a resin such as Sephadex to remove unreacted ligand and toxin molecules.

Numerous types of cytotoxic compounds may be joined to proteins through the use of a reactive group on the cytotoxic compound or through the use of a cross-linking agent. A common reactive group that will form a stable covalent bond in vivo with an amine is isothiocyanate (Means et al., Chemical modifications of proteins (Holden-Day, San Francisco 1971) pp. 105-110). This group preferentially reacts with the ϵ-amine group of lysine. Maleimide is a commonly used reactive group to form a stable in vivo covalent bond with the sulfhydryl group on cysteine (Ji., Methods Enzymol 91, 580-609 (1983)). Monoclonal antibodies typically are incapable of forming covalent bonds with radiometal ions, but they may be attached to the antibody indirectly through the use of chelating agents that are covalently linked to the antibodies. Chelating agents may be attached through amines (Meares et al., Anal. Biochem. 142, 68-78 (1984)) and sulfhydral groups (Koyama, Chem. Abstr. 120, 217262t (1994)) of amino acid residues and also through carbohydrate groups (Rodwell et al., PNAS USA 83, 2632-2636 (1986), Quadri et al., Nucl. Med. Biol. 20, 559-570 (1993)). Since these chelating agents contain two types of functional groups, one to bind metal ions and the other to joining the chelate to the antibody, they are commonly referred as bifunctional chelating agents (Sundberg et al., Nature 250, 587-588 (1974)).

A therapeutic or diagnostic agent may also or alternatively be attached at the hinge region of a reduced antibody component via disulfide bond formation. As an alternative, such peptides may be attached to the antibody component using a heterobifunctional cross-linker, such as N-succinyl 3-(2-pyridyldithio)proprionate (SPDP). Yu et al., Int. J. Cancer 56, 244 (1994). General techniques for such conjugation are well known in the art. See, for example, Wong, Chemistry Of Protein Conjugation And Cross-Linking (CRC Press 1991), Upeslacis et al., "Modification of Antibodies by Chemical Methods," In Monoclonal Antibodies: Principles And Applications, Birch et al., (eds.) (Wiley-Liss, Inc. 1995), Price, "Production and Characterization of Synthetic Peptide-Derived Antibodies," in Monoclonal Antibodies: Production, Engineering And Clinical Application, Ritter et al., (eds.) (Cambridge University Press 1995).

In some embodiments, labels or other conjugated substituents are attached to the anti-CD32b antibody amino acid sequence by spacer arms of various lengths to reduce potential steric hindrance.

In one embodiment, the present invention provides an anti-CD32b antibody, such as a human anti-CD32b antibody, conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins. Therapeutic agents, which may be administered in combination with a an anti-CD32b antibody of the present invention as described elsewhere herein, may also be candidates for therapeutic moieties useful for conjugation to an anti-CD32b antibody of the present invention.

Other examples of therapeutic cytotoxins that may be conjugated to an anti-CD32b antibody of the present invention include calicheamicins and duocarmycins. As indicated above, the drug moiety need not be construed as limited to classical chemical therapeutic agents. For example, the drug moiety may be a protein or polypeptide possessing a desired biological activity. Such proteins may include, for example, an agent active at the cell surface, such as phospholipase enzymes, e.g. phospholipase C. The lysing portion of a toxin typically may be readily joined to the Fab fragment of an antibody or antibody fragment of the present invention. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Additional toxins suitable for use in the present invention are known to those of skill in the art (see for instance U.S. Pat. No. 6,077,499).

Techniques for conjugating such therapeutic moieties to an anti-CD32b antibody are well known, see for instance Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985), Hellstrom et al., "Antibodies For Drug Delivery", in Controlled Drug Delivery (2nd Ed.), Robinson et al., (eds.), pp. 623-53 (Marcel Dekker, Inc. 1987), Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985), "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985) and Thorpe et al., "The Preparation And Cytotoxic Properties Of Antibody-Toxin Conjugates", Immunol. Rev. 62, 119-58 (1982).

In another embodiment, the present invention provides an anti-CD32b antibody that is conjugated to a mixed toxin. A mixed toxin molecule is a molecule derived from two different (typically polypeptide) toxins. Generally, peptide toxins comprise one or more domains responsible for generalized eukaryotic cell binding, at least one enzymatically active domain, and at least one translocation domain. The binding and translocation domains are required for cell recognition and toxin entry respectively. Naturally-occurring proteins which are known to have a translocation domain include diphtheria toxin, *Pseudomonas* exotoxin A, and possibly other peptide toxins. The translocation domains of diphtheria toxin and *Pseudomonas* exotoxin A are well characterized (see for instance Hoch et al., PNAS USA 82, 1692 (1985), Colombatti et al., J. Biol. Chem. 261, 3030 (1986) and Deleers et al., FEBS Lett. 160, 82 (1983)), and the existence and location of such a domain in other molecules may be determined by methods such as those employed by Hwang et al., Cell 48, 129 (1987) and Gray et al., PNAS USA 81 2645 (1984). In view of these techniques, a useful mixed toxin hybrid molecule may be formed, for example, by fusing the enzymatically active A subunit of *E. coli* Shiga-like toxin (Calderwood et al., PNAS USA 84, 4364 (1987)) to the translocation domain (amino acid residues 202 through 460) of diphtheria toxin, and to a molecule targeting a particular cell type, as described in U.S. Pat. No. 5,906,820. The targeting portion of the three-part hybrid can cause the molecule to attach specifically to the targeted cells, and the diphtheria toxin translocation portion can act to insert the enzymatically active A subunit of the Shiga-like toxin into a targeted cell. The enzymatically active portion of Shiga-like toxin, like diphtheria toxin, acts on the protein synthesis machinery of the cell to prevent protein synthesis, thus killing the targeted cell.

In one embodiment, the anti-CD32b antibody of the present invention is attached to a chelator linker, e.g. tiuxetan, which allows for the antibody to be conjugated to a radioisotope.

Additionally useful conjugate substituents include anti-cancer retinoids. Taxane conjugates (see for instance Jaime et al., Anticancer Res. 21(2A), 1119-28 (2001), cisplatin conjugates, thapsigargin conjugates, linoleic acid conjugates, calicheamicin conjugates (see for instance Damle et al., Curr Opin Pharmacol. 3(4), 386-90 (2003), doxorubicin conjugates, geldanamycin conjugates, and the like, also may be useful in promoting the treatment of cancer (see, generally, Trail et al., Cancer Immunol Immunother. 52(5), 328-37 (2003)).

In a further aspect, the invention relates to a bispecific molecule comprising an anti-CD32b antibody of the invention as described herein above and a second binding specificity such as a binding specificity for a human effector cell, a human Fc receptor or a T cell receptor. Or a binding specificity for another epitope of CD32b In one embodiment, said T cell receptor is CD3. In another embodiment, said human Fc receptor is human FcγRI (CD64) or a human Fcα receptor (CD89).

Bispecific molecules of the present invention may further include a third binding specificity, in addition to an anti-CD32b binding specificity and a binding specificity for a human effector cell, a human Fc receptor or a T cell receptor.

Exemplary bispecific antibody molecules of the invention comprise (i) two antibodies one with a specificity to CD32b and another to a second target that are conjugated together, (ii) a single antibody that has one chain specific to CD32b and a second chain specific to a second molecule, and (iii) a single chain antibody that has specificity to CD32b and a second molecule. Typically, the second target/second molecule is a molecule other than CD32b. In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Mart1, MelanA, MUM-1, MUM-2, MUM-3, HLA-B7, and Ep-CAM. In one embodiment, the second molecule is a cancer-associated integrin, such as α5β3 integrin. In one embodiment, the second molecule is an angiogenic factor or other cancer-associated growth factor, such as a vascular endothelial growth factor (VEGF), a fibroblast growth factor (FGF), epidermal growth factor (EGF), epidermal growth factor receptor (EGFR), angiogenin, and receptors thereof, particularly receptors associated with cancer progression (for instance one of the HER1-HER4 receptors). Other cancer progression-associated proteins discussed herein may also be suitable second molecules.

In one embodiment, a bispecific antibody of the present invention is a diabody. Bispecific antibodies also include cross-linked or "heteroconjugate" antibodies. For example, one of the antibodies in a heteroconjugate may be coupled to avidin and the other to biotin. Such antibodies have, for example, been proposed to target immune system cells to unwanted cells (see for instance U.S. Pat. No. 4,676,980). Heteroconjugate antibodies may be made using any convenient cross-linking methods. Suitable peptide cross-linking agents and techniques are well known in the art, and examples of such agents and techniques are disclosed in for instance U.S. Pat. No. 4,676,980.

In a further aspect, the invention relates to an expression vector encoding an antibody of the invention.

In one embodiment, the expression vector of the invention comprises a nucleotide sequence encoding one or more of the amino acid sequences selected from the group consisting of: SEQ ID NO:4, 12, 20, 48, 56, 64 and 72.

In another embodiment, the expression vector of the invention comprises a nucleotide sequence encoding one or more of the amino acid sequences selected from the group consisting of: SEQ ID NO:1, 9, 17, 25, 33, 41, 45, 53, 61 and 69.

In a further embodiment, the expression vector of the invention comprises a nucleotide sequence encoding one or more of the amino acid sequences selected from the group consisting of: SEQ ID NO:5, 13, 21, 29, 37, 49, 57, 65 and 73.

In a further embodiment, the expression vector further comprises a nucleotide sequence encoding the constant region of a light chain, a heavy chain or both light and heavy chains of an antibody, e.g. a human antibody.

Such expression vectors may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-CD32b antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the anti-CD32b antibody in a bacterial cell. Examples of such vectors include, for example, vectors which direct high level expression of fusion proteins that are readily purified (for instance multifunctional E. coli cloning and expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors for use in for instance Saccharomyces cerevisiae include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprises a nucleic acid sequence encoding a secretion/localization sequence, which can target a polypeptide, such as a nascent polypeptide chain, to a desired cellular compartment, membrane, or organelle, or which directs polypeptide secretion to periplasmic space or into cell culture media. Such sequences are known in the art, and include secretion leader or signal peptides, organelle targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like.

In an expression vector of the invention, anti-CD32b antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-CD32b-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacterial, and mammalian cells (e.g., immortalized mammalian cells). For example, in one embodiment, the present invention provides a cell comprising a nucleic acid stably integrated into the cellular genome that comprises a sequence coding for expression of an anti-CD32b antibody of the present invention. In another embodiment, the present invention provides a cell comprising a non-integrated nucleic acid, such as a plasmid, cosmid, phagemid, or linear expression element, which comprises a sequence coding for expression of an anti-CD32b antibody of the invention.

In a further aspect, the invention relates to a hybridoma which produces an antibody of the invention as defined herein. In an even further aspect, the invention relates to a transgenic non-human animal comprising nucleic acids encoding a human heavy chain and a human light chain, wherein the animal or plant produces an antibody of the invention of the invention. Generation of such hybridomas and transgenic animals has been described above.

In a further aspect, the invention relates to a method for producing an anti-CD32b antibody of the invention, said method comprising the steps of
a) culturing a hybridoma or a host cell of the invention as described herein above, and
b) purifying the antibody of the invention from the culture media.

In a further main aspect, the invention relates to an anti-CD32b antibody as defined herein or a bispecific molecule as defined herein for use as a medicament.

In an even further aspect, the invention relates to a pharmaceutical composition comprising:
an anti-CD32b antibody as defined herein or a bispecific molecule as defined herein, and
a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical corn position.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

In one embodiment the compounds of the present invention are administered in crystalline form by subcutaneous injection, cf. Yang et al., PNAS USA 100(12), 6934-6939 (2003).

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the corn positions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The pharmaceutical composition of the present invention may contain one compound of the present invention or a combination of compounds of the present invention.

In another aspect, the invention relates to the antibody of the invention as defined herein or a bispecific molecule of the invention as defined herein for use as a medicament.

In one embodiment, said use is for the treatment of cancer, such as a hematological cancer.

In a further embodiment, said use is for the treatment of B-cell neoplasms, such as a B-cell neoplasm selected from the group consisting of: small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma. In a preferred embodiment, the B-cell neoplasm is Burkitt's lymphoma.

In another embodiment, said use is for the treatment of leukaemia, such as acute myelogenous leukemia (AML); chronic lymphocytic leukemia (CLL) or chronic myelogenous leukemia (CML).

In yet another embodiment, said use is for the treatment of peripheral T-cell lymphoma or cutaneous T-cell lymphoma.

In an even further embodiment said use is for the treatment of melanoma.

Similarly, the invention relates to a method for inhibiting growth and/or proliferation of a tumor cell expressing CD32B, comprising administration, to an individual in need thereof, of an antibody or a bispecific molecule of the invention. In one embodiment, said tumor cell is involved in B-cell neoplasms, such as a B-cell neoplasm selected from the group consisting of: small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma. In another embodiment, said tumor cell is involved in leukaemia, such as Acute myelogenous leukemia (AML); Chronic lymphocytic leukemia (CLL) or Chronic myelogenous leukemia (CML).

In yet another embodiment, said tumor cell is involved in peripheral T-Cell lymphomas or cutaneous T-Cell lymphoma.

In an even further embodiment said tumor cell is involved in melanoma.

Also, the invention relates to the use of a monoclonal antibody that binds to human CD32b for the preparation of a medicament for the treatment of cancer, such as one of the specific cancer indications mentioned above.

In a further aspect, the invention relates to an antibody of the invention for the treatment of CD32c-expressing tumor cells. In one embodiment thereof, such tumor cells do not express CD32b. In an even further aspect, the invention relates to use of anti-CD32b antibodies of the invention for the treatment of autoimmune diseases in which CD32c is involved, such as idiopathic thrombocytopenic purpura.

In a further main aspect, the invention relates to the use of monoclonal anti-CD32b antibodies as an adjuvants, i.e. the antibody can be used for boosting an immune response through blocking of the inhibitory effects of CD32b. Studies have shown that the potency of a cytotoxic anti-tumor antibody can de dramatically increased by removing the inhibitory CD32b pathway in vivo (Clynes et al. 2000 Nat Med. 6:443-446)

Accordingly, in a main aspect, the invention relates to the anti-CD32b antibody of the invention for use as a stimulator of the immune system.

Similarly, the invention relates to method for stimulating the immune system, comprising administration, to an individual in need thereof, of an antibody of the invention and to the use of a anti-CD32B antibody of the invention for the preparation of a medicament for the stimulation of immune system.

In one embodiment, the anti-CD32b antibody of the invention is for use in combination with a therapeutic antibody, such as a therapeutic antibody which acts via activation of Fc receptors, e.g. an anti-tumor therapeutic antibody, such as an anti-CD20 therapeutic antibody (e.g. selected from: ofatumumab, 2C6 (WO2005103081), AME-133, TRU-015, IMMU-106, ocrelizumab (2H7.v16, PRO-70769, R-1594), Bexxar®/tositumomab and Rituxan®/rituximab), an anti-CD38 therapeutic antibody (e.g. those described in WO2006099875), an anti-EGFR therapeutic antibody (e.g. cetuximab, panitumumab or zalutumumab), an anti-CD4 therapeutic antibody (such as zanolimumab), an anti-CD52 therapeutic antibody (e.g. alemtuzumab), an anti-HER2/neu therapeutic antibody (e.g. trastuzumab), an anti-CD25 antibody (e.g. basiliximab) or an anti-GPR49 antibody. Table 1 of Carter (2006) Nature Reviews Immunology 6:343 lists further examples of antibodies the activity of which may be boosted with the anti-CD32b antibody of the invention.

An anti-CD32b antibody of the invention can also be used to boost an antibody response following vaccination. Thus, the invention also relates to an anti-CD32b antibody of the invention for use in combination with vaccination. For example, an anti-CD32b antibody could be used to boost vaccination, e.g. in metastatic melanoma, and could be used in combination with e.g. peptides or protein-based vaccines or dendritic-cell based vaccines.

CD32b is also expressed on mast cells. Thus, the anti-CD32b antibody of the invention may also be used for the treatment of hypersensitivities, such as asthma.

Furthermore, the anti-CD32b antibody of the invention may be used in the treatment of inflammatory and/or autoimmune diseases. For the use in the treatment of inflammatory the antibody may be alpha-2,6-sialylated.

In a preferred embodiment of the above described methods and uses of the antibody for stimulation of the immune system, an anti-CD32b antibody of the invention which does not mediate effector function is used to avoid undesired cytotoxic activity towards the CD32b-expressing cells. In a further preferred embodiment hereof, the anti-CD32b antibody is a stabilized IgG4 anti-CD32b antibody or a monovalent anti-CD32b antibody.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-CD32b antibodies depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg.

A physician or veterinarian having ordinary skill in the art may readily determine and prescribe the effective amount of the pharmaceutical composition required. For example, the physician or veterinarian could start doses of the anti-CD32b antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

In one embodiment, the anti-CD32b antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-CD32b antibodies may be administered by slow continuous infusion over a long period, such as more than 24 hours, in order to reduce toxic side effects.

In one embodiment the anti-CD32b antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-CD32b antibodies of the present invention.

In one embodiment, the anti-CD32b antibodies may be administered by maintenance therapy, such as, e.g., once a week for a period of 6 months or more.

In one embodiment, the anti-CD32b antibodies may be administered by a regimen including one infusion of an anti-CD32b antibody of the present invention followed by an infusion of an anti-CD32b antibody of the present invention conjugated to a radioisotope. The regimen may be repeated, e.g., 7 to 9 days later.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

An "effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An anti-CD32b antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Anti-CD32b antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing CD32b as described above, which methods comprise administration of an anti-CD32b antibody of the present invention combined with one or more additional therapeutic agents as described below.

In one embodiment, the present invention provides a method for treating a disorder involving cells expressing CD32b in a subject, which method comprises administration of a therapeutically effective amount of an anti-CD32b antibody of the present invention and at least one chemotherapeutic agent to a subject in need thereof.

In one embodiment, the present invention provides a method for treating or preventing cancer, which method comprises administration of a therapeutically effective amount of an anti-CD32b antibody of the present invention and at least one chemotherapeutic agent to a subject in need thereof.

In one embodiment, the present invention provides the use of an anti-CD32b antibody of the present invention for the preparation of a pharmaceutical composition to be administered with at least one chemotherapeutic agent for treating cancer.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents.

In one embodiment, such a chemotherapeutic agent may be selected from an anti-mitotic agent, such as taxanes, for instance docetaxel, and paclitaxel, and vinca alkaloids, for instance vindesine, vincristine, vinblastine, and vinorelbine.

In one embodiment, such a chemotherapeutic agent may be selected from a topoisomerase inhibitor, such as topotecan.

In one embodiment, such a chemotherapeutic agent may be selected from a growth factor inhibitor, such as an inhibitor of ErbB1 (EGFR) (such as Iressa, erbitux (cetuximab), tarceva and similar agents), an inhibitor of ErbB2 (Her2/neu) (such as herceptin and similar agents) and similar agents.

In one embodiment, such a chemotherapeutic agent may be selected from a tyrosine kinase inhibitor, such as imatinib (Glivec, Gleevec STI571), lapatinib, PTK787/ZK222584 and similar agents.

In one embodiment, the present invention provides a method for treating a disorder involving cells expressing CD32b in a subject, which method comprises administration of a therapeutically effective amount of an anti-CD32b antibody of the present invention and at least one inhibitor of angiogenesis, neovascularization, and/or other vascularization to a subject in need thereof Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one embodiment, a therapeutic agent for use in combination with an anti-CD32b antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J Immunol. 137(5), 1743-9 (1986), Pohl et al., Int J Cancer. 50(6), 958-67 (1992), Bohlen et al., Cytokines Mol Ther. 2(4), 231-8 (1996) and Maruyama, J Immunol Methods. 264(1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J Immunol. 17(11), 1645-8 (1987)), or a cell (for instance a red blood cell—see for instance Wi et al., J Immunol Methods. 122(2), 227-34 (1989)).

In one embodiment, a therapeutic agent for use in combination with an anti-CD32b antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins. These and other methods or uses involving naturally occurring peptide-encoding nucleic acids herein may alternatively or additionally be performed by "gene activation" and homologous recombination gene upregulation techniques, such as are described in U.S. Pat. No. 5,968,502, U.S. Pat. No. 6,063,630 and U.S. Pat. No. 6,187,305 and EP 0505500.

In one embodiment, a therapeutic agent for use in combination with an anti-CD32b antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxy-staurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and antisense Bcl-2.

In one embodiment, a therapeutic agent for use in combination with an anti-CD32b antibody for treating the disorders as described above may be a hormonal regulating agent, such as agents useful for anti-androgen and anti-estrogen therapy.

Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxy-progesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/-sandostatin) and similar agents.

In one embodiment, a therapeutic agent for use in combination with an anti-CD32b antibody for treating the disorders as described above may be an anti-anergic agents (for instance small molecule compounds, proteins, glycoproteins, or antibodies that break tolerance to tumor and cancer antigens). Examples of such compounds are molecules that block the activity of CTLA-4, such as MDX-010 (ipilimumab) (Phan et al., PNAS USA 100, 8372 (2003)).

In one embodiment, a therapeutic agent for use in combination with an anti-CD32b antibody for treating the disorders as described above may be a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with an anti-CD32b antibody for treating the disorders as described above may be an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h.

In one embodiment, a therapeutic agent for use in combination with an anti-CD32b antibody for treating the disorders as described above may be an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J Oncol. 4(1), 97-105 (2004), Collis et al., Int J Radiat Oncol Biol Phys. 57(2 Suppl), S144 (2003), Yang et al., Oncogene. 22(36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. No. 5,589,466, U.S. Pat. No. 5,593,972, U.S. Pat. No. 5,703,057, U.S. Pat. No. 5,879,687, U.S. Pat. No. 6,235,523, and U.S. Pat. No. 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50(3), 613-24 (2003), Reilly et al., Methods Mol Med. 69, 233-57 (2002) and Tirapu et al., Curr Gene Ther. 2(1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, the present invention provides combination compositions and combination administration methods wherein an anti-CD32b antibody is combined or co-administered with a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions. Accordingly, in one embodiment, the present invention provides combination compositions and combination administration methods wherein an anti-CD32b antibody is combined or co-administered with an oncolytic virus. Examples of such viruses include oncolytic adenoviruses and herpes viruses, which may or may not be modified viruses (see for instance Shah et al., J Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J Oncol. 24(4), 919-23 (2004) and Zwiebel et al., Semin Oncol. 28(4), 336-43 (2001).

Combination compositions and combination administration methods of the present invention may also involve "whole cell and "adoptive" immunotherapy methods. For instance, such methods may comprise infusion or re-infusion of immune system cells (for instance tumor-infiltrating lymphocytes (TILs), such as $CD4^+$ and/or $CD8^+$ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, an anti-CD32b antibody may be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell-death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with an anti-CD32b antibody for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with an anti-CD32b antibody for treating the disorders as described above are cathepsin B, modulators of cathepsin D dehydrogenase activity, glutathione-S-transferase (such as glutacyl-cysteine synthetase and lactate dehydrogenase), and similar agents.

Examples of other anti-cancer agents, which may be relevant as therapeutic agents for use in combination with an anti-CD32b antibody for treating the disorders as described above are estramustine and epirubicin.

Examples of other anti-cancer agents, which may be relevant as therapeutic agents for use in combination with an anti-CD32b antibody for treating the disorders as described above are a HSP90 inhibitor like 17-allyl amino geldanamycin, antibodies directed against a tumor antigen such as PSA, CA125, KSA, etc., integrins like integrin β1, inhibitors of VCAM and similar agents.

Examples of other anti-cancer agents, which may be relevant as therapeutic agents for use in combination with an anti-CD32b antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA, etc.).

In one embodiment, the present invention provides a method for treating a disorder involving cells expressing CD32b in a subject, which method comprises administration of a therapeutically effective amount of an anti-CD32b antibody, such as an anti-CD32b antibody of the present invention, and radiotherapy to a subject in need thereof.

In one embodiment, the present invention provides a method for treating or preventing cancer, which method comprises administration of a therapeutically effective amount of an anti-CD32b antibody, such as an anti-CD32b antibody of the present invention, and radiotherapy to a subject in need thereof.

In one embodiment, the present invention provides the use of an anti-CD32b antibody, such as an anti-CD32b antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In one embodiment, an anti-CD32b antibody may be administered in connection with the delivery of one or more agents that promote access of the anti-CD32b antibody or combination composition to the interior of a tumor. Such methods may for example be performed in association with the delivery of a relaxin, which is capable of relaxing a tumor (see for instance U.S. Pat. No. 6,719,977). In one embodiment, an anti-CD32b antibody of the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129(12), 669-75 (2003), Pooga et al., FASEB J. 12(1), 67-77 (1998) and Tseng et al., Mol Pharmacol. 62(4), 864-72 (2002).

In one embodiment, the present invention provides a method for treating a disorder involving cells expressing CD32b in a subject, which method comprises administration of a therapeutically effective amount of an anti-CD32b antibody and at least one anti-inflammatory agent to a subject in need thereof In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. antibodes described in WO2004058797, e.g. 10F8), anti-IL15 antibodies (e.g. antibodies described in WO03017935 and WO2004076620), anti-IL15R antibodies, anti-CD4 antibodies (e.g. zanolimumab), anti-CD11a antibodies (e.g., efalizumab), anti-alpha-4/beta-1 integrin (VLA4) antibodies (e.g. natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, antibodies against CD25 (e.g. those described in WO2004045512, such as AB1, AB7, AB11, and AB12), or antibodies binding to for instance MHC, CD2, CD3, CD4, CD7, CD28, B7, CD40, CD45, IFNγ, TNF-α, IL-4, IL-5, IL-6R, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In one embodiment, the present invention provides a method for treating a disorder involving cells expressing CD32b in a subject, which method comprises administration of a therapeutically effective amount of an anti-CD32b antibody and an anti-C3b(i) antibody to a subject in need thereof In one embodiment, a therapeutic agent for use in combination with anti-CD32b antibodies for treating the disorders as described above may be selected from histone deacetylase inhibitors (for instance phenylbutyrate) and/or DNA repair agents (for instance DNA repair enzymes and related compositions such as dimericine).

Methods of the present invention for treating a disorder as described above comprising administration of a therapeutically effective amount of an anti-CD32b antibody may also comprise anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004). Likewise, an anti-CD32b antibody may be used for the preparation of a pharmaceutical composition for treating a disorder as described above to be administered with anti-cancer directed photodynamic therapy (for instance anti-cancer laser therapy—which optionally may be practiced with the use of photosensitizing agent, anti-cancer sound-wave and shock-wave therapies, and/or anti-cancer nutraceutical therapy.

As described above, a pharmaceutical composition of the present invention may be administered in combination therapy, i.e., combined with one or more agents relevant for the disease or condition to be treated either as separate pharmaceutical compositions or with a compound of the present invention coformulated with one or more additional therapeutic agents as described above. Such combination therapies may require lower dosages of the compound of the present invention and/or the co-administered agents, thus avoiding possible toxicities or complications associated with the various monotherapies.

Particularly preferred embodiments of the above-described combination therapies include the following:

For the treatment of follicular B-Cell lymphoma: an anti-CD32b antibody in combination with anti-CD20 antibodies e.g. rituximab or ofatumumab, optionally further in combination with chemotherapy e.g. CHOP or CVP or bendamustine and/or irradiation.

For the treatment of diffuse large B-Cell lymphoma: an anti-CD32b antibody in combination with anti CD20 antibodies e.g. rituximab or ofatumumab, optionally in further combination with chemotherapy e.g. ACVBP or CHOP or/and irradiation.

For the treatment of chronic lymphocytic leukemia: an anti-CD32b antibody in combination with anti CD20 antibodies e.g. rituximab or ofatumumab, optionally in combination with chemotherapy e.g. Fludarabine or bendamustine.

For the treatment of CML: an anti-CD32b antibody in combination with kinase inhibitors (KIs) (tyrosine KIs e.g. Imatinib or aurora KIs e.g. MK-0457) and/or chemotherapy.

For the treatment of AML: an anti-CD32b antibody in combination with chemotherapy e.g. cytarabine and anthracycline and/or with myelotag (an anti-CD33 antibody linked to the cytotoxic agent calicheamicin).

For the treatment of peripheral T-cell lymphomas: an anti-CD32b antibody in combination with other antibody therapy, e.g anti-CD4 antibody (such as zanolimumab) monotherapy or in combination with chemotherapy and/or radiotherapy.

For the treatment of cutaneous T-cell lymphoma: an anti-CD32b antibody in combination with antibody therapy e.g. anti-CD4 antibody (such as zanolimumab) optionally in further combination with local or total body electron beam irradiation or phototherapy (PUVA, narrow- or broad band UVB) or Histone deacetylase inhibitors, or retinoid X-receptor antagonists.

The anti-CD32b antibodies of the invention may also be used for diagnostic purposes. Thus, in a further aspect, the invention relates to a diagnostic composition comprising an anti-CD32b antibody as defined herein.

In one embodiment, the anti-CD32b antibodies of the present invention may be used in vivo or in vitro for diagnosing diseases wherein activated cells expressing CD32b play an active role in the pathogenesis, by detecting levels of CD32b, or levels of cells which contain CD32b on their membrane surface. This may be achieved, for example, by contacting a sample to be tested, optionally along with a control sample, with the anti-CD32b antibody under conditions that allow for formation of a complex between the antibody and CD32b. Complex formation is then detected (e.g., using an ELISA). When using a control sample along with the test sample, complex is detected in both samples and any statistically significant difference in the formation of complexes between the samples is indicative of the presence of CD32b in the test sample.

Thus, in a further aspect, the invention relates to a method for detecting the presence of CD32b antigen, or a cell expressing CD32b, in a sample comprising:

contacting the sample with an anti-CD32b antibody of the invention or a bispecific molecule of the invention, under conditions that allow for formation of a complex between the antibody and CD32b; and analyzing whether a complex has been formed.

In one embodiment, the method is performed in vitro.

More specifically, the present invention provides methods for the identification of, and diagnosis of invasive cells and tissues, and other cells targeted by anti-CD32b antibodies of the present invention, and for the monitoring of the progress of therapeutic treatments, status after treatment, risk of developing cancer, cancer progression, and the like.

In one example of such a diagnostic assay, the present invention provides a method of diagnosing the level of invasive cells in a tissue comprising forming an immunocomplex between an anti-CD32b antibody and potential CD32b-containing tissues, and detecting formation of the immunocomplex, wherein the formation of the immunocomplex correlates with the presence of invasive cells in the tissue. The contacting may be performed in vivo, using labeled isolated antibodies and standard imaging techniques, or may be performed in vitro on tissue samples.

Anti-CD32b antibodies may be used to detect CD32b-containing peptides and peptide fragments in any suitable biological sample by any suitable technique. Examples of conventional immunoassays provided by the present invention include, without limitation, an ELISA, an RIA, FACS assays, plasmon resonance assays, chromatographic assays, tissue immunohistochemistry, Western blot, and/or immunoprecipitation using an anti-CD32b antibody. Anti-CD32b antibodies of the present invention may be used to detect CD32b and CD32b-fragments from humans. Suitable labels for the anti-CD32b antibody and/or secondary antibodies used in such techniques include, without limitation, various enzymes, prosthetic groups, fluorescent materials, luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^{3}$H.

Anti-CD32b antibodies may also be assayed in a biological sample by a competition immunoassay utilizing CD32b peptide standards labeled with a detectable substance and an unlabeled anti-CD32b antibody. In such an assay, the biological sample, the labeled CD32b peptide standard(s) and the anti-CD32b antibodies are combined and the amount of labeled CD32b standard bound to the unlabeled anti-CD32b antibody is determined. The amount of CD32b peptide in the biological sample is inversely proportional to the amount of labeled CD32b standard bound to the anti-CD32b antibody.

The anti-CD32b antibodies are particularly useful in the in vivo imaging of tumors. In vivo imaging of tumors associated with CD32b may be performed by any suitable technique. For example, $^{99}$Tc-labeling or labeling with another gamma-ray emitting isotope may be used to label anti-CD32b antibodies in tumors or secondary labeled (e.g., FITC labeled) anti-CD32b antibody:CD32b complexes from tumors and imaged with a gamma scintillation camera (e.g., an Elscint Apex 409ECT device), typically using low-energy, high resolution collimator or a low-energy all-purpose collimator. Stained tissues may then be assessed for radioactivity counting as an indicator of the amount of CD32b-associated peptides in the tumor. The images obtained by the use of such techniques may be used to assess biodistribution of CD32b in a patient, mammal, or tissue, for example in the context of using CD32b or CD32b-fragments as a biomarker for the presence of invasive cancer cells. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Such images may also be used for targeted delivery of other anti-cancer agents, examples of which are described herein (e.g., apoptotic agents, toxins, or CHOP chemotherapy compositions). Moreover, such images may also or alternatively serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer). Carcinoma cancer cells, which may make up to 90% of all cancer cells, for example, have been demonstrated to stain very well with anti-CD32b antibody conjugate compositions. Detection with monoclonal anti-CD32b antibodies described herein may be indicative of the presence of carcinomas that are aggressive/invasive and also or alternatively provide an indication of the feasibility of using related monoclonal anti-CD32b antibody against such micrometastases.

In one embodiment, the present invention provides an in vivo imaging method wherein an anti-CD32b antibody of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient.

For diagnostic imaging, radioisotopes may be bound to a anti-CD32b antibody either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313).

In addition to radioisotopes and radio-opaque agents, diagnostic methods may be performed using anti-CD32b antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds. In order to load an anti-CD32b antibody with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to anti-CD32b antibodies using standard chemistries.

Thus, the present invention provides diagnostic anti-CD32b antibody conjugates, wherein the anti-CD32b antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of CD32b antigen, or a cell expressing CD32b, in a sample comprising an anti-CD32b antibody of the invention or a bispecific molecule of the invention; and instructions for use of the kit.

In one embodiment, the present invention provides a kit for diagnosis of cancer comprising a container comprising an anti-CD32b antibody, and one or more reagents for detecting binding of the anti-CD32b antibody to a CD32b peptide. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more anti-CD32b antibodies, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with an anti-CD32b antibody, such as a conjugated/labeled anti-CD32b antibody, for the detection of a cellular activity or for detecting the presence of CD32b peptides in a tissue sample or host. In such diagnostic kits, as well as in kits for therapeutic uses described elsewhere herein, an anti-CD32b antibody typically may be provided in a lyophilized form in a container, either alone or in conjunction with additional antibodies specific for a target cell or peptide. Typically, a pharmaceutical acceptable carrier (e.g., an inert diluent) and/or components thereof, such as a Tris, phosphate, or carbonate buffer, stabilizers, preservatives, biocides, biocides, inert proteins, e.g., serum albumin, or the like, also are included (typically in a separate container for mixing) and additional reagents (also typically in separate container(s)). In certain kits, a secondary antibody capable of binding to the anti-CD32b antibody, which typically is present in a separate container, is also included. The second antibody is typically conjugated to a label and formulated in manner similar to the anti-CD32b antibody the present invention. Using the methods described above and elsewhere herein anti-CD32b antibodies may be used to define subsets of cancer/tumor cells and characterize such cells and related tissues/growths.

In situ detection may be accomplished by removing a histological specimen from a patient, and providing the combination of labeled anti-CD32b antibodies, of the present invention to such a specimen. The anti-CD32b antibody of the present invention may be provided by applying or by overlaying the labeled anti-CD32b antibody of the present invention to a biological sample. Through the use of such a procedure, it is possible to determine not only the presence of CD32b or CD32b-fragments but also the distribution of such peptides in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In a further aspect, the invention relates to an anti-idiotypic antibody which binds to an anti-CD32b antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of an anti-CD32b mAb with the mAb to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to anti-CD32b antibodies of the present invention. For example, anti-Id mAbs may be coupled to a carrier such as keyhole limpet hemocyanin (KLH) and used to immunize BALB/c mice. Sera from these mice typically will contain anti-anti-Id antibodies that have the binding properties similar if not identical to an original/parent CD32b antibody.

The present invention is further illustrated by the following examples which should not be construed as further limiting.

EXAMPLES

Example 1

Expression Constructs for Producing Recombinant CD32a, CD32b and their Soluble Extracellular Domains For CD32a and CD32b, fully codon optimized constructs for expression in HEK cells, were generated at GeneArt (Regensburg, Germany). The proteins encoded by these constructs are identical to Genbank accession number AAA35932 for CD32a and P31994 for CD32b. The constructs did contain suitable restriction sites for cloning and an optimal Kozak sequence (Kozak, 1987). The constructs were cloned in the mammalian expression vector pEE13.4 (Lonza Biologics)(Bebbington, Renner et al. 1992). PCR was used to amplify the part, encoding the extracellular domain (amino acid 1-223) of CD32b, from the synthetic construct, adding a C-terminal His tag (CD32aECDHis). The construct was cloned in pEE13.4 and fully sequenced to confirm the correctness of the construct.

PCR was used to amplify the part, encoding the extracellular domain (amino acid 1-215) of CD32a, from the RZPD clone IRAKp961D2442Q2 (Deutsche Ressourcenzentrum für Genomforschung, RZPD, Berlin, Germany), adding a C-terminal His-tag, suitable restriction sites and an ideal Kozak sequence (CD32bECDHis). The construct was cloned in pEE13.4 and fully sequenced to confirm the correctness of the construct.

Example 2

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain vectors were coexpressed.

Example 3

Immunization Procedure of Transgenic Mice

Antibodies 020, 022, 024, 026, 028, 034, 038 and 053 were derived from the following immunizations: Four KM mice (4 males), strain GG2489, strain GG2713, nine HCo17 mice (described in US20050191293) (4 males and 5 females), four HCo20 mice (constructed essentially as described in US20050191293) (2 males and 2 females), strain GG2714, four HCo12-Balb/C mice (4 females), strain GG2811 and four HCo7 (3 males and 1 female), strain GG2201 (Medarex, San Jose, Calif., USA) were immunized every fortnight alternating with $5\times10^6$ transiently transfected HEK-CD32b cells, or with 20 µg of CD32bECDHis protein coupled to KLH. Eight immunizations were performed in total, four intraperitoneal (IP) and four subcutaneous (SC) immunizations at the tail base. The first immunization with cells was done in complete Freunds' adjuvant (CFA; Difco Laboratories, Detroit, Mich., USA). For all other immunizations, cells were injected IP in PBS and CD32bECDHis protein coupled to KLH was injected SC using incomplete Freunds' adjuvant (CFA; Difco Laboratories, Detroit, Mich., USA). When serum titers were found to be sufficient, mice were additionally boosted twice intravenously (IV) with 10 µg CD32bECDHis protein coupled to KLH in 100 µl PBS, 4 and 3 days before fusion. Antibody 016 was obtained using the following immunization strategy: Three HCo12 mice (3 males), GG2198 and two HCo7 mice (2 females), GG2201 were tolerized twice with $5\times10^6$ transiently transfected HEK-CD32a cells in RIBI adjuvant (Sigma Aldrich, St. Louis, Mo., USA) on day 0 and 14 and 100 µl cyclophosphamide (25 mg/kg) (Sigma, Zwijndrecht, The Netherlands) on day 1, 2, 15 and 16. Six immunizations with $5\times10^6$ transiently transfected HEK-CD32b cells followed the tolerization period on day 21, 28, 35, 56, 70, and 84. The first two immunizations were performed in RIBI adjvuvant, the other in incomplete Freunds' adjuvant. When serum titers were found to be sufficient, mice were additionally boosted twice IV with $1\times10^6$ transiently transfected HEK-CD32b cells in 100 µl PBS, 4 and 3 days before fusion.

Antibody 063 was obtained using the following immunization strategy: Three HCo7 mice (3 females), strain GG2201 and two HCo17 mice (2 females), strain GG2713 (Medarex, San Jose, Calif., USA) were tolerized twice with 15 µg CD32aECDHis protein in RIBI adjuvant (Sigma Aldrich, St. Louis, Mo., USA) on day 0 and 14 and 100 µl cyclophosphamide (50 mg/kg) (Sigma, Zwijndrecht, The Netherlands) on day 1, 2, 15 and, 16. Three immunizations with 15 µg CD32bECDHis protein coupled to KLH in RIBI adjuvant followed the tolerization period on day 21, 28, and 35. When serum titers were found to be sufficient, mice were additionally boosted twice IV with 10 µg CD32bECDHis protein in RIBI adjuvant in 100 µl PBS, 4 and 3 days before fusion.

Example 4

Homogeneous Antigen Specific Screening Assay

The presence of anti-CD32b antibodies in sera of immunized mice or HuMab (human monoclonal antibody) hybridoma culture supernatant was determined by homogeneous antigen specific screening assays using Fluorometric Micro volume Assay Technology (FMAT; Applied Biosystems, Foster City, Calif., USA). In short, F(ab')$_2$ goat-anti-human IgG Fc (Jackson ImmunoResearch Europe) was biotinylated, using the EZ-link NHS-PEO$_4$-biotinylation kit (Pierce) according to the manufacturer's instructions, and coated onto streptavidin beads (Applied Biosystems) in FMAT buffer (PBS supplemented with 0.1% (w/v) BSA and 0.01% (w/v) NaN$_3$). CD32bECDHis and CD32aECDHis recombinant proteins (Example 1) were labeled with Alexa Fluor 647 (Molecular Probes, Invitrogen, Breda, The Netherlands) and CY5.5 (Amersham Biosciences, Roosendaal, The Netherlands), respectively, according to the manufacturer's instructions. F(ab')$_2$ goat-anti-human IgG Fc-coated beads (5000 beads/well), diluted in FMAT buffer, were mixed with a serial dilution of HuMab mouse sera or HuMab hybridoma supernatant and Alexa647-labeled CD32bECDHis (60 ng/ml) in 384-wells black flat-bottomed microtiterplates (Greiner Bio-One, Alphen a/d Rijn, The Netherlands). Alternatively, CY5.5-labeled CD32aECDHis (60 ng/ml) was used as detecting reagent to test for cross-reactivity with CD32a. The plates were incubated for 6 hrs at RT in the dark and scanned by the Applied Biosystems 8200 Cellular Detection System (8200 CDS) and counts× fluorescence was used as read-out.

Example 5

HuMab Hybridoma Generation

HuMab mice with sufficient antigen-specific titerdevelopment were sacrificed and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Selection and culturing of the resulting HuMab hybridomas was done, based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Example 6

Lead Clone Generation by Limiting Dilution

To obtain a homogenic monoclonal cell population producing one monoclonal antibody a limiting dilution (LD) was performed for antibodies 020, 022, 024, and 028. In short, cells were seeded at a density of 0.1 cells per well to assure outgrowing cells originated from a single founder cell. With this density the chance of retrieving a monoclonal cell line in one LD round is 95.1 percent. After 14 days supernatant was screened for specific antibody production. The best IgG producing clone was expanded for production and frozen down. (e.g. as described by Underwood et al., J. Immunol. Methods 107: 119-128 (1988) and Coller et al. Methods in Enzymology 121: 412-413 (1986)

Example 7

Construction of Expression Vectors for the Expression of the Chimeric Anti-CD32b Antibody 2B6

The VH and VL encoding sequences of the mouse anti-CD32b antibody 2B6 were copied from patent WO04016750. Suitable signal peptides from the same germline families were added and fully codon optimized constructs for expression in HEK cells, were generated. The constructs did contain suitable restriction sites for cloning and an optimal kozak sequence. The VL construct was cloned in the mammalian expression vector pKappa, encoding the fully codon optimized human kappa constant light chain region in the mammalian expression vector pEE12.4 (Lonza Biologics). The VH construct was cloned in pG1f, encoding the fully codon optimized human IgG1 constant heavy chain region (allotype f) in the mammalian expression vector pEE6.4 (Lonza Biologics)

Example 8

Sequence Analysis of the Anti-CD32b HuMab Variable Domains and Cloning in Expression Vectors Total RNA of the anti-CD32b HuMabs was prepared from $5 \times 10^6$ hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned into the pCR-Blunt II-TOPO vector (Invitrogen) using the Zero Blunt PCR cloning kit (Invitrogen). For each HuMab, 16 VL clones and 8 VH clones were sequenced. The sequences are given in the Sequence Listing and FIG. 12 herein. List 1 (below) gives an overview of the sequence information. The VL and VH encoding regions of antibodies 016, 026, 034, 038, 053 and 063 were cloned into the pKappa and pG1f vectors to obtain the antibody light chain and heavy chain expression vectors for transient expression in HEK-293F cells.

| List 1 | |
|---|---|
| SEQ ID NO | Antibody name, part (germline origin) |
| 1 | Antibody 016, VH (IGHV3-33*01) |
| 2 | Antibody 016, VH CDR1 |
| 3 | Antibody 016, VH CDR2 |
| 4 | Antibody 016, VH CDR3 |
| 5 | Antibody 016, VL (IGKV3-11*01) |
| 6 | Antibody 016, VL CDR1 |
| 7 | Antibody 016, VL CDR2 |
| 8 | Antibody 016, VL CDR3 |
| 9 | Antibody 020, VH (IGHV1-18*01) |
| 10 | Antibody 020, VH CDR1 |
| 11 | Antibody 020, VH CDR2 |
| 12 | Antibody 020, VH CDR3 |
| 13 | Antibody 020, VL (IGKV1D-16*01) |
| 14 | Antibody 020, VL CDR1 |
| 15 | Antibody 020, VL CDR2 |
| 16 | Antibody 020, VL CDR3 |
| 17 | Antibody 022, VH (IGHV1-18*01) |
| 18 | Antibody 022, VH CDR1 |
| 19 | Antibody 022, VH CDR2 |
| 20 | Antibody 022, VH CDR3 |
| 21 | Antibody 022, VL (IGKV1D-16*01) |
| 22 | Antibody 022, VL CDR1 |
| 23 | Antibody 022, VL CDR2 |
| 24 | Antibody 022, VL CDR3 |
| 25 | Antibody 024, VH (IGHV1-18*01) |
| 26 | Antibody 024, VH CDR1 |
| 27 | Antibody 024, VH CDR2 |
| 28 | Antibody 024, VH CDR3 |
| 29 | Antibody 024, VL (IGKV1D-16*01) |
| 30 | Antibody 024, VL CDR1 |
| 31 | Antibody 024, VL CDR2 |
| 32 | Antibody 024, VL CDR3 |
| 33 | Antibody 026, VH (IGHV1-18*01) |
| 34 | Antibody 026, VH CDR1 |
| 35 | Antibody 026, VH CDR2 |
| 36 | Antibody 026, VH CDR3 |
| 37 | Antibody 026, VL (IGKV1D-16*01) |
| 38 | Antibody 026, VL CDR1 |
| 39 | Antibody 026, VL CDR2 |
| 40 | Antibody 026, VL CDR3 |
| 41 | Antibody 028, VH (IGHV1-18*01) |
| 42 | Antibody 028, VH CDR1 |
| 43 | Antibody 028, VH CDR2 |
| 44 | Antibody 028, VH CDR3 |
| 45 | Antibody 034, VH (IGHV3-23*01) |
| 46 | Antibody 034, VH CDR1 |
| 47 | Antibody 034, VH CDR2 |
| 48 | Antibody 034, VH CDR3 |
| 49 | Antibody 034, VL (IGKV3-11*01) |
| 50 | Antibody 034, VL CDR1 |
| 51 | Antibody 034, VL CDR2 |
| 52 | Antibody 034, VL CDR3 |
| 53 | Antibody 038, VH (IGHV3-30*03) |
| 54 | Antibody 038, VH CDR1 |
| 55 | Antibody 038, VH CDR2 |
| 56 | Antibody 038, VH CDR3 |
| 57 | Antibody 038, VL (IGKV3-11*01) |
| 58 | Antibody 038, VL CDR1 |
| 59 | Antibody 038, VL CDR2 |
| 60 | Antibody 038, VL CDR3 |
| 61 | Antibody 053, VH (IGHV3-33*01) |
| 62 | Antibody 053, VH CDR1 |
| 63 | Antibody 053, VH CDR2 |
| 64 | Antibody 053, VH CDR3 |
| 65 | Antibody 053, VL (IGKV1-13*02) |
| 66 | Antibody 053, VL CDR1 |
| 67 | Antibody 053, VL CDR2 |
| 68 | Antibody 053, VL CDR3 |
| 69 | Antibody 063, VH (IGHV3-23*01) |
| 70 | Antibody 063, VH CDR1 |
| 71 | Antibody 063, VH CDR2 |
| 72 | Antibody 063, VH CDR3 |
| 73 | Antibody 063, VL (IGKV3-11*01) |
| 74 | Antibody 063, VL CDR1 |
| 75 | Antibody 063, VL CDR2 |
| 76 | Antibody 063, VL CDR3 |
| 77 | VH CDR1 sub-generic sequence |
| 78 | VH CDR2 sub-generic sequence |
| 79 | VH CDR3 sub-generic sequence |

Example 9

Purification of Antibodies

Culture supernatant was filtered over 0.2 μm dead-end filters and loaded on 5 ml Protein A columns (rProtein A FF, Amersham Bioscience) and eluted with 0.1 M citric acid-NaOH, pH 3. The eluate was immediately neutralized with 2M Tris-HCl, pH 9 and dialyzed overnight to 12.6 mM $NaH_2PO_4$, 140 mM NaCl, pH 7.4 (B.Braun). After dialysis samples were sterile filtered over 0.2 µm dead-end filters. Purity was determined by SDS-PAGE and concentration was measured by nephelometry and absorbance at 280 nm. Purified antibodies were aliquoted and stored at −80° C. Once thawed, purified antibody aliquots were kept at 4° C.

Mass spectrometry was performed to identify the molecular mass of the antibody heavy and light chains expressed by the hybridomas. MS analysis of antibodies 020 and 028 under reducing conditions demonstrated the presence of a light chain with a common mass of 23,493 Dalton which is consistent with the predicted light chain mass of antibody 020 (23,495 Dalton). Furthermore, heavy chains were observed with masses of 48,771 and 48,757 Dalton for antibody 020 and 028, respectively, which correlates well with the predicted masses (antibody 020, 48,773 Dalton; antibody 028, 48,759 Dalton).

Example 10

Binding of Anti-CD32b HuMabs to the Extracellular Domains of CD32a and CD32b in ELISA The specificity of the obtained anti-CD32b HuMabs was evaluated by ELISA. ELISA plates (Microlon; Greiner Bio-One) were coated overnight at 4° C. with 2 µg/ml of CD32aECDHis and CD32bECDHis in PBS, pH 7.4. Coated ELISA plates were washed with PBS, blocked for one hour at room temperature with 2% (v/v) chicken serum (Gibco, Paisley, Scotland) in PBS and washed again with PBS. Subsequently, HuMabs, serially diluted in PBSTC (PBS supplemented with 2% (v/v) chicken serum and 0.05% (v/v) Tween-20), were incubated for 1 hr at RT under shaking conditions (300 rpm). Bound HuMabs were detected using HRP-conjugated goat-anti-human IgG antibodies (Jackson ImmunoResearch Europe) diluted 1:10,000 in PBSTC, which were incubated for 1 hr at RT under shaking conditions (300 rpm). The reaction was further developed with ABTS (Roche Diagnostics) at RT in the dark, stopped after 20-30 minutes by adding 2% (w/v) oxalic acid and then the absorbance at 405 nm was measured. HuMab-KLH (a human monoclonal antibody against KLH (keyhole limpet haemocyanin)), was used as a negative control. Binding curves were analyzed using non-linear regression (sigmoidal dose-response with variable slope) using GraphPad Prism V4.03 software.

Figure 1B:
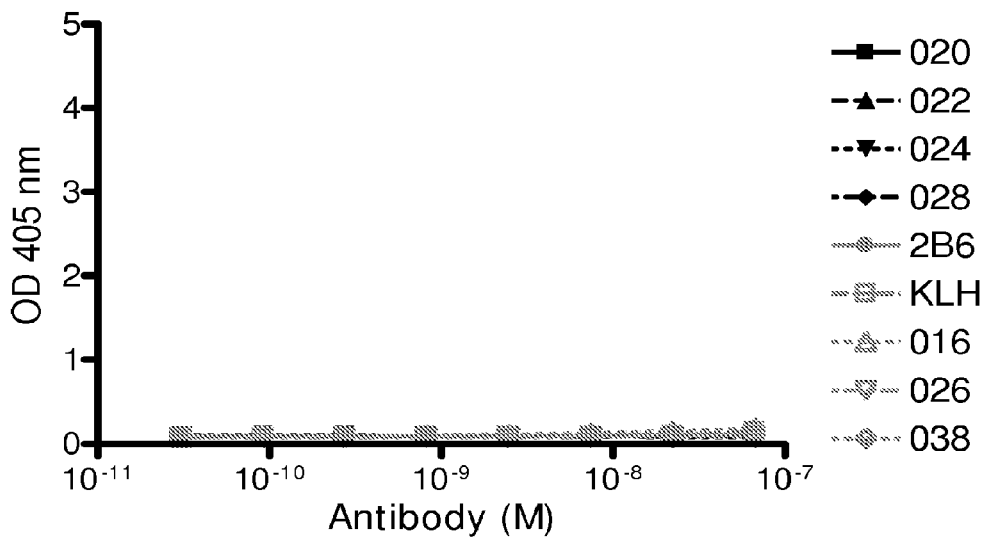

As can been seen in FIG. 1A, all of the anti-CD32b antibodies bound CD32bECDHis. The $EC_{50}$ values for the HuMabs varied between 0.28 and 0.75 nM (Table 1). No reactivity with CD32aECDHis was observed (FIG. 1B).

TABLE 1

$EC_{50}$ values of binding of anti-CD32b HuMabs to CD32bECDHis

| HuMab | $EC_{50}$ (nM) |
|---|---|
| 016 | 0.28 |
| 020 | 0.49 |
| 022 | 0.75 |
| 024 | 0.75 |
| 026 | 0.51 |
| 028 | 0.48 |
| 038 | 0.62 |
| 2B6 | 1.24 |
| KLH | N.A. |

$EC_{50}$ values are the mean of at least 3 experiments
N.A. not applicable, no binding observed Example 11

Manufacturing Luciferase-Transfected (Daudi-Luc) Cells, Clone 1E3

Culture of Daudi cells (originating from Burkitt's lymphoma) was cultured in RPMI 1640 culture medium supplemented with 10% FCS (Optimum C241, Wisent Inc., St. Bruno, QC, Canada), 2 mM L-glutamine, 100 IU/ml penicillin, 100 mg/ml streptomycin, 1 mM sodium pyruvate (all derived from Gibco BRL, Life Technologies, Paisley, Scotland). Medium was refreshed twice a week. Before transfection, cells were split and seeded out at 1-1.5×10$^6$ cells/ml to ensure viability and optimal growth.

Luciferase Transfection $8.2 \times 10^6$ CD32b$^+$ Daudi cells were taken up in 350 µl RPMI (supplemented with 10% dFCS, Gibco BRL) and transferred to an electroporation cuvet (Biorad, Hemel Hempstead, Herts, UK). Then, 40 µg gWIZ luciferase from GTS (Aldevron, Fargo, N. Dak., USA) and 10 µg pPur vector (BD Biosciences, Alphen a/d Rijn, The Netherlands), which confers puromycin resistance, were added. After resting cells on ice for 10 minutes, cells were electroporated (250 V, 950 µF; Gene Pulser II, Biorad Laboratories GmbH, Munchen, Germany). Cells were again rested on ice, and taken up in 40 ml RPMI (supplemented with 10% FCS). Then, cells were plated out in 96-well tissue culture plates (100 µl per well). After 48 hours, puromycin (final concentration: 1 µg/ml; Sigma-Aldrich Chemie BV, Zwijndrecht, The Netherlands) was added. Puromycin-resistant clones were further grown in 24-well tissue culture plates.

Determination of Luciferase Activity

Luciferase activity of cells was determined using the Luciferase Assay System (Promega, Madison, Wis., USA). $1 \times 10^5$ cells were centrifuged (13,500 rpm, 1 min) in an eppendorf centrifuge, and the pellet was washed in 100 µl PBS. After centrifugation (13,500 rpm, 1 min), pellet was lysed with 20 µl Reporter Lysis Buffer (Promega), frozen and thawed. After centrifugation (13,500 rpm, 1 min), 20 µl supernatant was discarded, and 100 µl luciferase assay reagent was added (in special luminometer tubes, Promega). Luminescence was measured (10 sec) in a luminometer (LB9507, Berthold, Vilvoorde, Belgium).

Example 12

Binding of Anti-CD32b HuMabs to Membrane-Bound CD32a and CD32b, Expressed on IIA1.6 Cells and Daudi-Luc Cells After harvesting and counting, IIA1.6 cells stably transfected with full length CD32a and CD32b (van den Herik-Oudijk et al., 1994), control IIA1.6 cells and Daudi-luc cells were resuspended in PBS ($1 \times 10^6$ cells/ml). Cells were put in 96-well V-bottom plates (100 µl/well) and washed twice with FACS buffer (PBS supplemented with 0.1% BSA and 0.02% Na-azide). Thereafter, 50 µl of serially diluted HuMab in FACS buffer was added to the cells and incubated for 30 minutes at 4° C. After washing three times with FACS buffer, 50 µl of phycoerythrin (PE)-conjugated rabbit anti-human IgG (Jackson ImmunoResearch Europe), diluted 1:200 in FACS buffer, was added. After 30 minutes at 4° C. (in the dark), cells were washed three times, and specific binding of the HuMabs was detected by flow cytometry on a FACSCalibur (BD Biosciences). HuMab-KLH was used as a negative control. Binding curves were analyzed using non-linear regression (sigmoidal dose-response with variable slope) using GraphPad Prism V4.03 software (GraphPad Software, San Diego, Calif., USA).

Figure 2A:
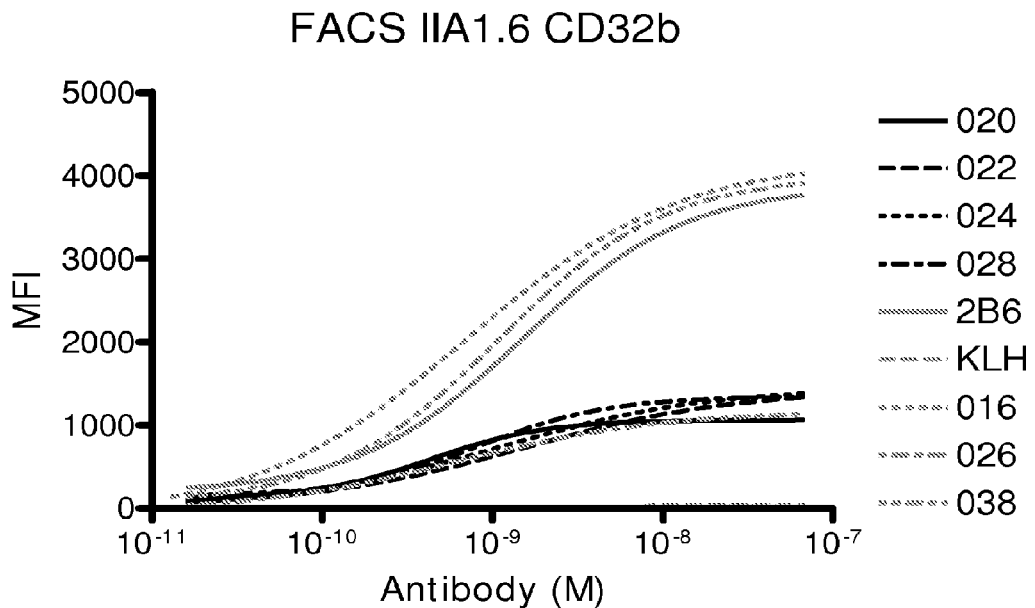
FIGS. 2A-2C show binding of anti-CD32b antibodies to stably transfected IIA1.6 cells expressing full length CD32b (FIG. 2A), CD32a (FIG. 2B) or Daudi-luc cells (FIG. 2C) as measured by flow cytometry.

FIG. 2A shows that all tested HuMabs bound CD32b-expressing IIA1.6 cells in a dose-dependent manner with $EC_{50}$ values in the range of 0.44-1.51 nM (Table 2). No binding to control IIA1.6 cells was observed (data not shown). As indicated by the lower maximal mean fluorescence intensities (MFI), CD32b-expressing IIA1.6 cells did not bind as much HuMab 020, 022, 024, 026, or 028 compared to HuMab 016 or 038, or antibody 2B6. In contrast, ELISA experiments revealed that CD32bECDHis was capable of binding relatively more HuMab 020, 022, 024, 026, or 028 than HuMab 016 or 038. This observation may suggest that CD32b, when expressed on the cell surface, harbors fewer binding sites for HuMabs 020, 022, 024, 026 and 028 compared to HuMabs 016 and 038, and antibody 2B6.

Figure 2B:
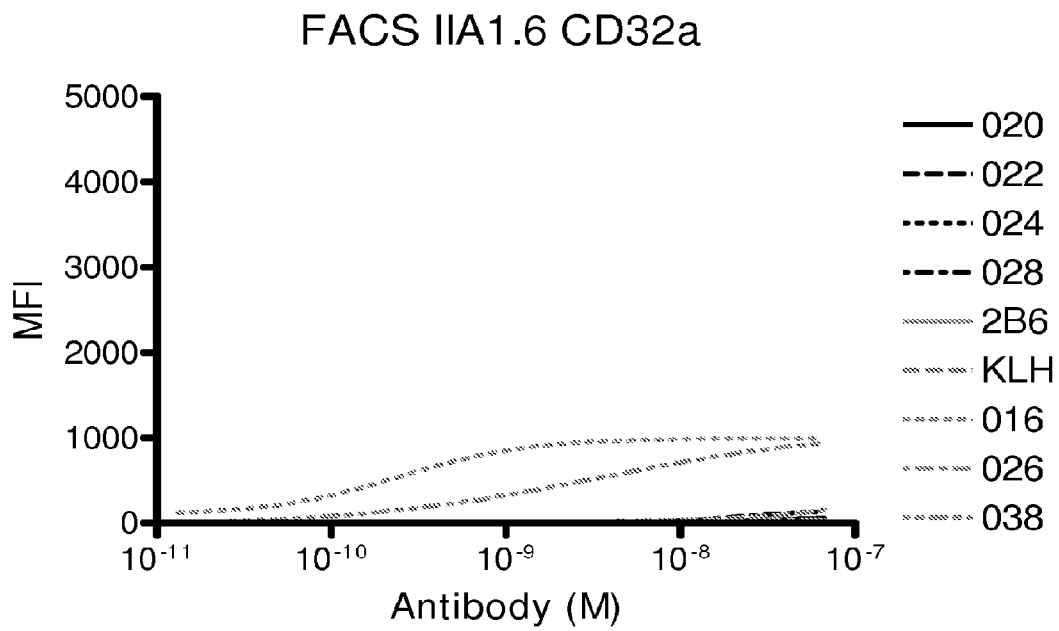
Figure 2C:
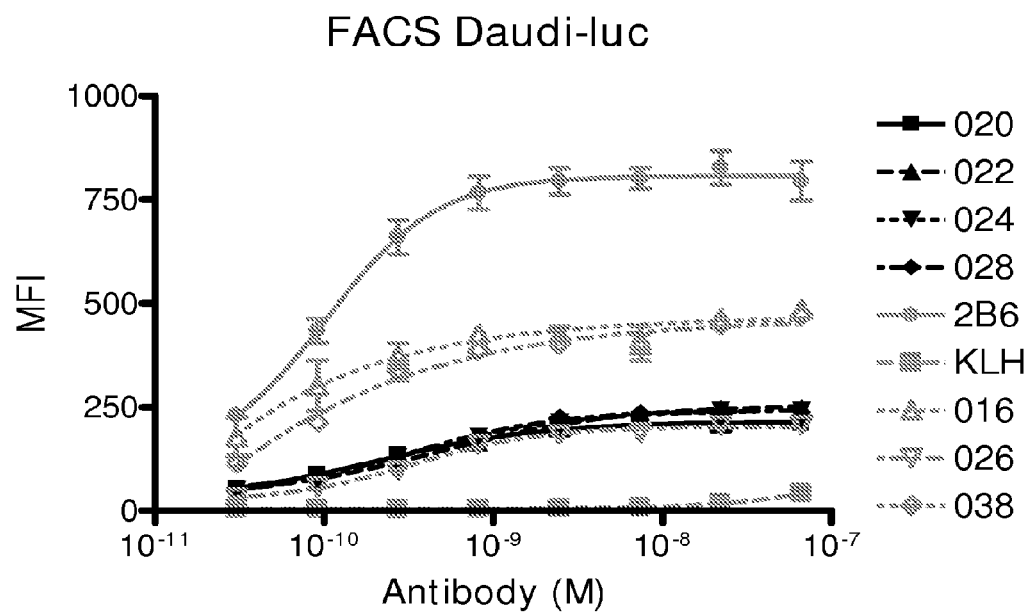

HuMabs 016 and 038 also bound CD32a-expressing IIA.16 cells (FIG. 2B), although with 3-4 fold lower maximal MFIs than observed for binding to CD32b-expressing IIA1.6 cells. FACS staining with pan-CD32 monoclonal antibodies revealed that both IIA1.6 variants expressed equal amounts of CD32 (data not shown). All anti-CD32b HuMabs also bound Daudi-luc cells (FIG. 2C), albeit with different $EC_{50}$ values (Table 2). Although similar binding curves were obtained for binding of antibody 016, 038, and 2B6 to CD32b-expressing IIA1.6 cells (FIG. 2A), the binding curves obtained for binding to Daudi-luc cells were different (FIG. 2C). For 016 and 038, the maximum MFIs were approximately 2-fold lower compared to that of 2B6. Together, the ELISA and flow cytometry experiments described supra suggest that the antibodies can be divided into three groups on the basis of their binding characteristics. The first group, consisting of antibodies 020, 022, 024, 026 and 028, reacts highly with CD32bECDHis and showed relatively low MFIs when tested on CD32b-expressing IIA1.6 cells. The second group, consisting of antibodies 016 and 038 also reacts heavily with CD32bECDHis, showed crossreactivity to CD32a when expressed on IIA1.6 cells and showed intermediate signals when tested for reactivity with Daudi-luc cells. Because antibody 2B6 bound strongly to CD32b-expressing IIA1.6 and Daudi cells, this antibody differs from the antibodies in the two previous groups.

Example 13

Antibody-Dependent Cell-Mediated Cytotoxicity

Daudi cells ($5\times10^6$ cells) were harvested, washed (twice in PBS, 1500 rpm, 5 min) and collected in 1 ml RPMI++ (RPMI 1640 culture medium supplemented with 10% cosmic calf serum (HyClone, Logan, Utah, USA)), to which 100 μCi $^{51}$Cr (Chromium-51; Amersham Biosciences Europe GmbH, Roosendaal, The Netherlands) was added. The mixture was incubated in a shaking water bath for 1 hr at 37° C. After washing of the cells (twice in PBS, 1500 rpm, 5 min), the cells were resuspended in RPMI++ and counted by trypan blue exclusion. Cells were brought to a concentration of $1\times10^5$ cells/ml.

Preparation of Effector Cells

Peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France. After resuspension of cells in RPMI++, cells were counted by trypan blue exclusion and brought to a concentration of $1\times10^7$ cells/ml.

ADCC Set UP

50 μl of $^{51}$Cr-labeled targets cells were transferred to microtiter wells, and 50 μl of serially diluted antibody was added, diluted in RPMI++. Cells were incubated (RT, 15 min), and 50 μl effector cells were added, resulting in an effector to target ratio of 100:1. To determine the maximum level of lysis, 100 μl 5% Triton-X100 was added instead of effector cells; to determine the spontaneous level of lysis, 100 μl RPMI++ was added; to determine the level of antibody independent lysis, 50 μl effector cells and 50 μl RPMI++ was added). Subsequently, cells were incubated for 4 hr at 37° C., 5% $CO_2$. After spinning down the cells (1200 rpm, 3 min), 75 μl of supernatant was transferred to micronic tubes. The released $^{51}$Cr was counted in a gamma counter and the percentage of antibody mediated lysis was calculated as follows:

((cpm sample−cpm antibody independent lysis)/(cpm maximal lysis−cpm spontaneous lysis))×100% wherein cpm is counts per minute.

Figure 3:
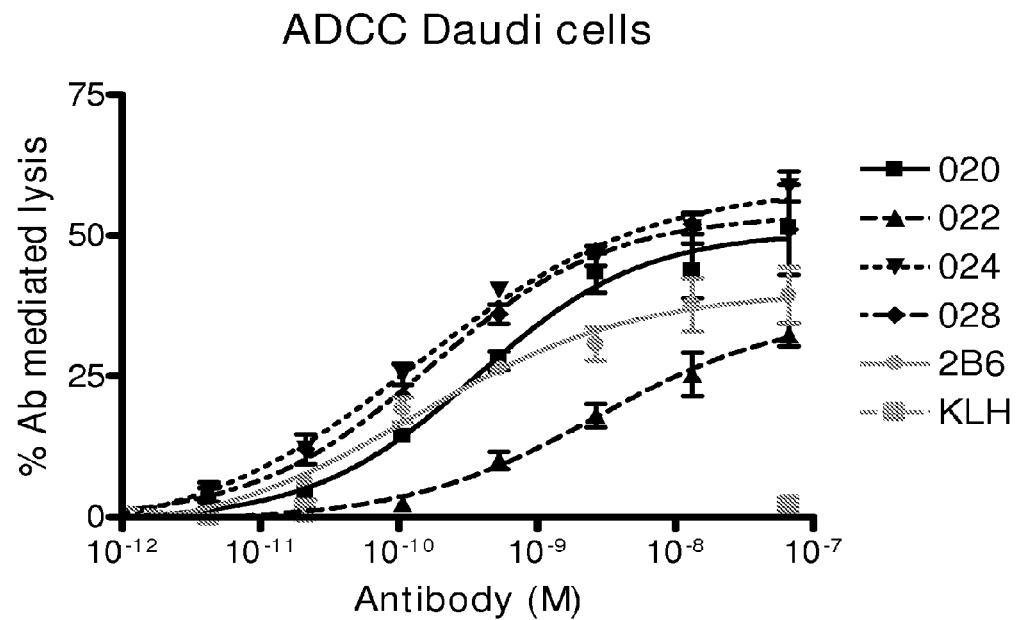
FIG. 3 shows the ability of anti-CD32b-antibodies to induce lysis of Daudi cells by ADCC as compared to HuMab-KLH

FIG. 3 shows that all tested anti-CD32b HuMabs induced lysis of Daudi cells by ADCC, albeit with different efficiencies (Table 3). All HuMabs, but 022 and 2B6, were able to induce the similar maximum level of antibody mediated lysis.

TABLE 2

$EC_{50}$ values of binding of anti CD32b-HuMabs to IIA1.6-CD32a cells, IIA1.6-CD32b cells, and Daudi-luc cells.

| HuMab | $EC_{50}$ (nM) IIA1.6-CD32b | $EC_{50}$ (nM) CD32a | $EC_{50}$ (nM) Daudi-luc |
|---|---|---|---|
| 016 | 0.71 | 0.25 | <0.01 |
| 020 | 0.44 | N.A. | 0.21 |
| 022 | 1.51 | N.A. | 0.49 |
| 024 | 1.13 | N.A. | 0.30 |
| 026 | 0.64 | N.A. | 0.34 |
| 028 | 0.83 | N.A. | 0.34 |
| 038 | 1.08 | 3.48 | <0.01 |
| 2B6 | 1.49 | N.A. | 0.10 |
| KLH | N.A. | N.A. | N.A. |

Values are the mean of at least 3 experiments, N.A. not applicable, no binding observed

TABLE 3

$EC_{50}$ values of CD32b-specific antibodies obtained in ADCC using Daudi cells

| HuMab | $EC_{50}$ (nM) Daudi |
|---|---|
| 020 | 0.36 |
| 022 | 2.74 |
| 024 | 0.14 |
| 028 | 0.17 |
| 2B6 | 0.13 |
| KLH | N.A. |

$EC_{50}$ values are the mean of 3 independent samples
N.A. not applicable, no ADCC observed Example 14

Competition Studies Using Sandwich-ELISA

ELISA wells were coated overnight at 4° C. with anti-CD32b HuMabs serially diluted in PBS. The ELISA wells were washed with PBS, blocked for one hour at room temperature with 2% (v/v) chicken serum (Gibco, Paisley, Scotland) in PBS and washed again with PBS. Subsequently, the immobilized antibodies were incubated with biotinylated CD32bECDHis serially diluted in PBSTC. After washing with PBS/Tween, bound biotinylated CD32bECDHis was incubated with Streptavidin-poly-HRP (Sanquin, Amsterdam, The Netherlands) for 1 hr at RT an the reaction was developed as described supra. The conditions that resulted in sub-optimal binding of each antibody were determined and used for following experiments to determine which antibodies compete for binding.

To this end, ELISA wells coated with anti-CD32b HuMabs were incubated in the presence of an excess of CD32b-specific antibody and the predetermined concentration of biotinylated CD32bECDHis in fluid phase. The reaction was developed as described. Residual binding was expressed as percentage relative to binding observed in the absence of competitor antibody.

As shown in Table 4, all antibodies, when added as competitor antibody were able to compete for binding with their immobilized counterparts, except for antibody 016. It was not possible to determine which antibodies compete for binding with antibody 016, because biotinylated CD32bECDHis was not recognized by antibody 016. This also explains why antibody 016, when added as competitor antibody, did not compete for binding with any of the tested antibodies. Apparently, antibody 016 binds a unique epitipe, since binding of the other antibodies was not abrogated upon biotinylation of CD32bECDHis.

2B6 when added as competitor antibody competed with antibody 038. However, the reverse reaction did not reveal competition by antibody 038. This can be explained by the lower affinity of antibody 038 or the chosen reaction conditions. The other antibodies were unable to compete for binding with antibody 2B6. Values higher than 100% can be explained by avidity effects and the formation of antibody-CD32bECDHis complexes containing two non-competing antibodies. Antibodies 020, 022, 024, 026, 028, 034, 053 and 063 compete for binding to CD32bECDHis.

Example 15

BIAcore Analysis

Antibody binding to CD32a and CD32b was analyzed by surface plasmon resonance in a BIAcore 3000 (GE Healthcare). CD32aECDHis and CD32bECDHis derived from HEK293 cells were used for the analysis. HuMab antibodies were immobilized on the CM-5 sensor chip according to the procedure recommended by the manufacturer. Briefly, after surface activation by EDC and NHS HuMab antibody was injected over the activated CM-5 surface in 10 mM sodium-acetate, pH ranging from 4.0 to 5.5 at 5 µl/min. followed by 1 M Ethanolamine for deactivation. Concentration series of CD32bECDHis in HBS-EP buffer were injected over the immobilized antibodies at a flow rate of 30 µl/min for 180 sec. Regeneration of the HuMab surface was performed by injection of 10 mM Glycine-HCl pH 2.0 or 10 mM sodium acetate pH 3.0. Reference curves were obtained by injection of CD32bECDHis over an isotype human antibody (HuMab KLH). Kinetic analysis is performed using double reference subtraction and model 1:1 (langmuir) binding analysis. Specificity was studied by injecting CD32aECDHis at a concentration of 100 mM over immobilized HuMab and isotype control antibodies under the same conditions as for the CD32b measurements. There was no detectable binding of CD32aECDHis to the HuMab antibodies (data not shown).

Table 5 shows that all HuMabs bound CD32bECDHis with (sub) nanomolar affinities in the range of 0.7-2.4 nM. For 2B6, the identical affinity (0.3 nM) as described previously (Rankin et al., 2006) was measured.

TABLE 5

Kinetic constants ($k_a$, $k_d$ and $K_D$) of anti-CD32b antibodies for reactivity with CD32bECDHis

| | $k_a$ (1/M × s) × 10$^5$ | $k_d$ (1/s) × 10$^{-4}$ | $K_D$ (nM) |
|---|---|---|---|
| 020 | 15.4 ± 3.7 | 36.3 ± 2.8 | 2.4 ± 0.4 |
| 022 | 14.8 ± 1.8 | 10.3 ± 0.9 | 0.7 ± 0.1 |
| 024 | 14.4 ± 0.8 | 12.6 ± 0.2 | 0.9 ± 0.1 |
| 028 | 15.8 ± 0.2 | 19.9 ± 1.3 | 1.3 ± 0.1 |
| 016 | 26.6 ± 1.3 | 28.0 ± 0.1 | 1.1 ± 0.1 |
| 026 | 14.0 ± 2.0 | 17.9 ± 1.7 | 1.3 ± 0.2 |
| 038 | 15.4 ± 1.0 | 15.6 ± 0.1 | 1.0 ± 0.1 |

TABLE 4

Competition of anti-CD32b antibodies for binding to biotinylated CD32bECDHis.

| Immobilized antibody | Competitor antibody | | | | | | | | | | |
|---|---|---|---|---|---|---|---|---|---|---|---|
| | 016 | 038 | 2B6 | 034 | 022 | 024 | 020 | 028 | 026 | 053 | 063 |
| 016 | N.A. | N.A. | N.A. | N.A. | N.A. | N.A. | N.A. | N.A. | N.A. | N.A. | N.A. |
| 038 | 105 | 17 | 5 | 354 | 350 | 351 | 310 | 317 | 308 | 333 | 283 |
| 2B6 | 105 | 113 | 20 | 185 | 179 | 174 | 163 | 165 | 168 | 185 | 181 |
| 034 | 98 | 98 | 90 | 23 | 63 | 56 | 83 | 75 | 83 | 90 | 89 |
| 022 | 102 | 115 | 96 | 7 | 14 | 13 | 35 | 27 | 42 | 64 | 63 |
| 024 | 101 | 103 | 98 | 6 | 17 | 15 | 43 | 34 | 56 | 69 | 68 |
| 020 | 105 | 120 | 126 | 1 | 6 | 4 | 20 | 13 | 28 | 42 | 42 |
| 028 | 109 | 121 | 125 | 2 | 6 | 7 | 24 | 15 | 32 | 51 | 45 |
| 026 | 104 | 127 | 146 | 0 | 1 | 1 | 4 | 3 | 4 | 29 | 27 |
| 053 | 98 | 168 | 195 | 4 | 8 | 6 | 19 | 13 | 26 | 40 | 43 |
| 063 | 103 | 102 | 98 | 8 | 29 | 23 | 59 | 49 | 70 | 79 | 0 |

Values represent percentage residual binding relative to binding observed in the absence of competitor antibody.
N.A. Not applicable, antibody 016 did not bind biotinylated CD32bECDHis TABLE 5-continued Kinetic constants ($k_a$, $k_d$ and $K_D$) of anti-CD32b antibodies for reactivity with CD32bECDHis

| | $k_a$ (1/M × s) × $10^5$ | $k_d$ (1/s) × $10^{-4}$ | $K_D$ (nM) |
|---|---|---|---|
| 2B6 | 26.1 ± 2.4 | 8.7 ± 1.1 | 0.3 ± 0.1 |
| 2B6* | 26.1 ± 12.4 | 6.9 ± 0.9 | 0.3 ± 0.1 |

Values are the mean of 3 independent concentration series (±SD); 2B6 (n = 6)
*Reported kinetic constants according to Rankin et al., Blood. 2006; 108(7): 2384-91

Example 16

Blocking of Fc-Mediated Binding of IgG to CD32b and CD32a by Competition of Fab-Mediated Binding of Anti-CD32b HuMabs Determined by Time-Resolved Fluorescent Resonance Energy Transfer (TR-FRET)

To study the interaction of anti-CD32b HuMabs with CD32b and CD32a in more detail TR-FRET technology was applied. To this end, CD32bECDHis and CD32aECDHis were labeled with a fluorescent donor molecule directed against the histidine tag (Anti-6×His Europium3+, PerkinElmer, Boston Mass.). HuMab-KLH (a human monoclonal antibody against KLH (keyhole limpet haemocyanin) symbolized normal IgG and was labeled with a fluorescent acceptor molecule (AlexaFluor-647, Invitrogen). Binding of the AlexaFluor-647 labeled antibody to the Europium3+ labeled CD32 resulted in 6×His antibody—CD32-HuMab—KLH protein complexes, which emit light at 665 nm upon excitation at 340 nm. This fluorescent light was measured using a time-resolved fluorescence microplate reader (EnVision 2101 Multilabel reader).

Competition of AlexaFluor 647-conjugated HuMab-KLH by unlabeled anti-CD32b HuMab for binding to Europium3+-conjugated CD32 can be detected by a decrease in TR-FRET fluorescence. In the unbound state, the distance between the donor and acceptor fluophores is too large for energy transfer to occur. A serial dilution of unlabeled anti-CD32b HuMab was used to obtain a dose-dependent competition curve. The $IC_{50}$ value was calculated from the competition curves to compare affinities of tested HuMab's (see FIG. 4 for an example).

Briefly, all dilutions were made in 0.5× Lance detection buffer (PerkinElmer, Boston Mass.) supplemented with 0.2% BSA (obtained via dilution of 7.5% BSA Stabilizer solution, cat: CR84-100, PerkinElmer) and 0.03% (v/v) Tween-20 (Riedel de Haen, Seelze, Germany). CD32bECDHis and CD32aECDHis were diluted to 0.5 µg/ml. To obtain equal top-fluorescence levels for both receptors, 48.8 µg/ml a-KLH-AlexaFluor 647 was added to CD32bECDHis (~22× molar excess of AlexaFluor 647 labelled a-KLH) and 23.6 µg/ml a-KLH-AlexaFluor 647 was added to CD32aECDHis (~9× molar excess of AlexaFluor 647 labeled a-KLH). Anti-6×His Europium3+ (PerkinElmer, Boston Mass.) was diluted to 0.15 µg/ml. A 4-fold serial dilution of the tested HuMab antibody was made in a 96 wells non-binding plate (cat. 650261, Greiner Bio-one, Frickenhausen, Germany), ranging from 10 µg/ml-0.04 ng/ml. Subsequently, 25 µl of either CD32bECDHis or CD32aECDHis, 25 µl HuMab-KLH-AlexaFluor 647, 25 µl anti-6×His Europium3+ and 25 µl test mAb were transferred to a 96-well opti-white plate. After overnight incubation at 4° C. in the dark, fluorescence was measured using an EnVision 2101 Multilabel reader (PerkinElmer, Boston, Mass.) applying the following settings; Lance/Delfia dual mirror, emission filter 615-665 nm, excitation filter 320 nm, delay time 60 µs, window 100 µs, 100 flashes, 2000 µs per cycle and bidirectional row-by-row reading. Binding curves were analyzed using non-linear regression (sigmoidal dose-response with variable slope) using GraphPad Prism V4.03 software (GraphPad Software, San Diego, Calif., USA).

Table 6 shows Fab-mediated ligand inhibition by all tested antibodies ($IC_{50}$ values ranging from 0.24-0.57 nM; antibodies 053 and 063, data not shown). HuMab-KLH was only capable of displacing its labeled counterpart by Fc-mediated binding, resulting in a significantly higher $IC_{50}$ ($IC_{50}$ of 417 nM for CD32bECDHis and 134 nM for CD32aECDHis). HuMabs 016, 034 and 038 also displaced HuMab-KLH-AlexaFluor 674 from CD32aECDHis by Fab-mediated binding, as indicated by the relatively low $IC_{50}$ values. Antibodies 2B6, 016 and 038 were able to completely inhibit HuMab-KLH-AlexaFluor 674 binding to CD32bECDHis by Fab-mediated binding. In contrast, HuMabs 020, 022, 024, 026, 028, 053, and 063 induce approximately 70% of maximal Fab-mediated inhibition at antibody concentrations in the range of 0.1-1 µg/ml (FIG. 4). At antibody concentrations higher than 1 µg/ml, HuMab-KLH-AlexaFluor 674 binding to CD32bECDHis is further inhibited from 70 to 100% by an additive Fc-mediated inhibition. This additive inhibitory effect is further illustrated by the Fc-mediated inhibition of HuMab-KLH-AlexaFluor 674 binding that is observed for unlabeled HuMab-KLH at antibody concentrations of 1 µg/ml and higher.

TABLE 6

$IC_{50}$ values of binding of anti-CD32b-HuMabs to CD32bECDHis and CD32aECDHis determined with a TR-FRET based binding competition assay

| HuMab | CD32b $IC_{50}$ (nM) | CD32b SD (nM) | CD32a $IC_{50}$ (nM) | CD32a SD (nM) |
|---|---|---|---|---|
| 016 | 0.24 | 0.19 | 2.0 | 1.8 |
| 020 | 0.35 | 0.27 | N.A. | N.A. |
| 022 | 0.44 | 0.33 | N.A. | N.A. |
| 024 | 0.45 | 0.27 | N.A. | N.A. |
| 026 | 0.3 | 0.17 | N.A. | N.A. |
| 028 | 0.35 | 0.27 | N.A. | N.A. |
| 034* | 0.45* | 0.027* | 1.6* | 0.2* |
| 038 | 0.37 | 0.22 | 13.9 | 4.87 |
| 2B6 | 0.57 | 0.24 | N.A. | N.A. |
| KLH | 417 | 160 | 134 | 50.4 |

Values are the mean of at least 3 experiments, (*except 034 N = 2).
N.A. not applicable,
Fc-mediated competition similar to HuMab-KLH observed.

Example 17

Luciferase Transfection of Daudi Cells with pGL3-Vector $10 \times 10^6$ CD32b+ Daudi cells were taken up in 350 µl RPMI (supplemented with 10% dFCS (Gibco BRL), penicillin, streptomycin and Na-pyruvate) and transferred to an electroporation cuvet (Biorad, Hemel Hempstead, Herts, UK). Then, 40 µg pGL3 luciferase from Promega (Leiden, The Netherlands) and 4 µg pPur vector (BD Biosciences, Alphen a/d Rijn, The Netherlands), which confers puromycin resistance, were added. After resting cells on ice for 10 minutes, cells were electroporated (250 V, 950 µF; Gene Pulser II, Biorad Laboratories GmbH, Munchen, Germany). Cells were again rested on ice, and taken up in 20 ml RPMI (supplemented with 10% FCS). Then, cells were plated out in 96-well tissue culture plates (100 μl per well). After 48 hours, puromycin (final concentration: 2 μg/ml; Sigma-Aldrich Chemie BV, Zwijndrecht, The Netherlands) was added. Puromycin-resistant clones were further grown in 24-well tissue culture plates. Daudi-luc clone 2E32E10 was used for in vivo experiments (see example 18).

Example 18

Xenograft Tumor Model in SCID Mice

To determine the efficacy of anti-CD32b HuMabs to inhibit tumor growth or tumor proliferation in vivo, seven to eleven week-old female SCID-mice, strain C.B-17/IcrCrl-scid/scid, were purchased from Charles River Laboratories Nederland (Maastricht, the Netherlands) and kept under sterile conditions in filter-top cages with food and water provided ad libitum. All experiments were approved by the Utrecht University animal ethics committee. Anti-CD32b HuMabs (20 μg; clones 020, 022, 024, and 028) were injected intraperitoneally at day 0. HuMab-KLH (20 μg) was included as negative control. A chimeric antibody against CD20, Rituxan (20 μg; Genentech, San Francisco, Calif., USA) and antibody 2B6 were included as positive control antobies. On the same day as antibody treatment, $2.5 \times 10E^6$ Daudi-luc cells (see example 17, clone 2E32E10) in PBS were inoculated intravenously in the tail vain. Mice were examined at least twice per week for clinical signs of illness. Tumor size was determined by in vivo imaging at weekly intervals, starting on day 14. For this, mice were anesthetized using KXA and D-Luciferin (Biothema, Haninge, Sweden) was administered (125 mg/kg, intraperitoneally). Luciferin imaging was started 10 min. later with a 5 min. exposure time on a Biospace φ imager (Biospace, Paris, France), from which whole body emission values were calculated. Additionally, plasma levels of anti-CD32b HuMabs were checked at day 7, by means of ELISA.

Alternatively, $2.5 \times 10E^6$ Daudi-luc cells (see example 11, clone 1E3) in PBS were inoculated at day 0 followed by antibody administration at day 6, essentially as described supra.

Figure 5A:
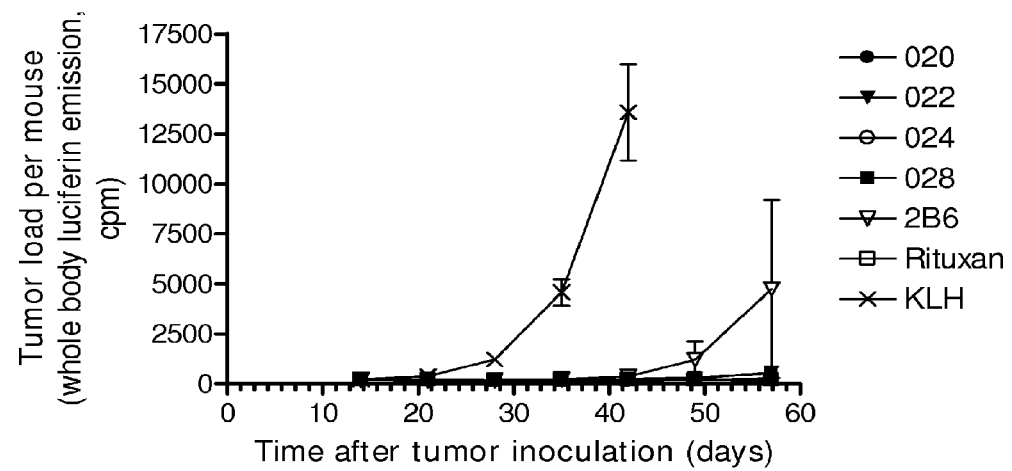
FIGS. 5A and 5B show anti-tumor efficacy of anti-CD32b antibodies in vivo in a xenograft tumor model in SCID mice. Antibodies were administered at day 0 (FIG. 5A) or 6 days after tumor challenge (FIG. 5B); shown are the mean counts per minute (cpm) values per treatment group ±SEM.

As can been seen in FIG. 5A, tumor growth of Daudi cells was inhibited by positive control Rituxan and by HuMabs 020, 022, 024 an 028 to a similar extent. The inhibition was compared to treatment with negative control HuMab-KLH. Tumor growth of Daudi cells was delayed but not completely inhibited by reference mAb 2B6.

Figure 5B:
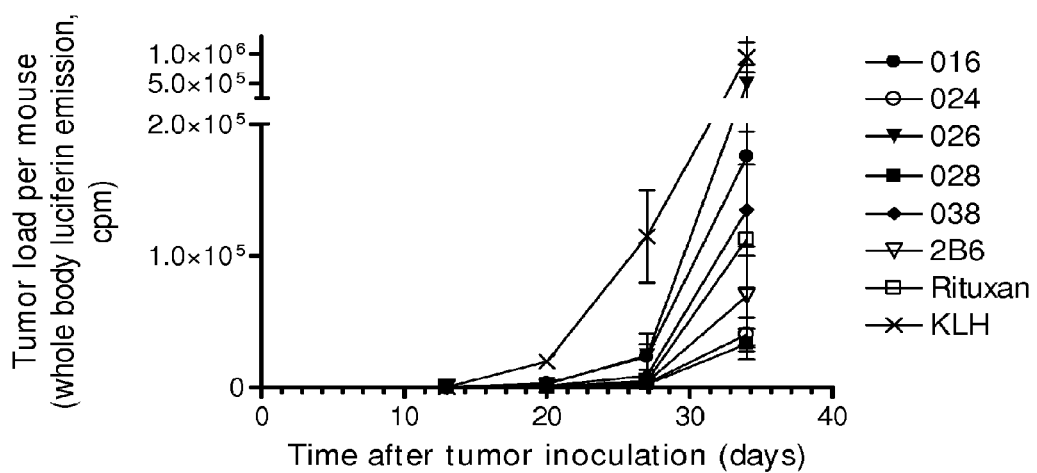

FIG. 5B shows that tumor growth in mice treated 6 days after challange was not completely inhibited. However, tumor outgrowth was significantly delayed by antibodies 024, 028 and 2B6 (p<0.01) and 016, 038 and Rituxan (p<0.05) compared to treatment with negative control HuMab-KLH.

Example 19

Xenograft Tumor Model in SCID Mice

The efficacy of anti-CD32b HuMabs to inhibit tumor growth or tumor proliferation in vivo was determined as described supra. Daudi-luc cells (2.5×10E6) (clone 1E3, see example 17) were inoculated at day 0. Anti-CD32b HuMabs (20 μg; clones 024, 028 [both purified from hybridoma material] and clones 034 and 053 [both purified from transiently transfected HEK-293F cells]) were injected at day 6 (experiment shown in FIG. 6A). Injection of HuMabs was confirmed by measuring human IgG levels in serum at day 15. Alternatively, 2.5×10E6 Daudi-luc cells in PBS were inoculated at day 0 followed by antibody administration at day 6 (shown in FIG. 6B) or day 14 (shown in FIG. 6C). All HuMab clones used in this experiment were purified from transiently transfected HEK-293F cells. Injection of HuMabs was confirmed by measuring human IgG levels in serum at day 24 and day 38 after tumor challenge.

Figure 6A:
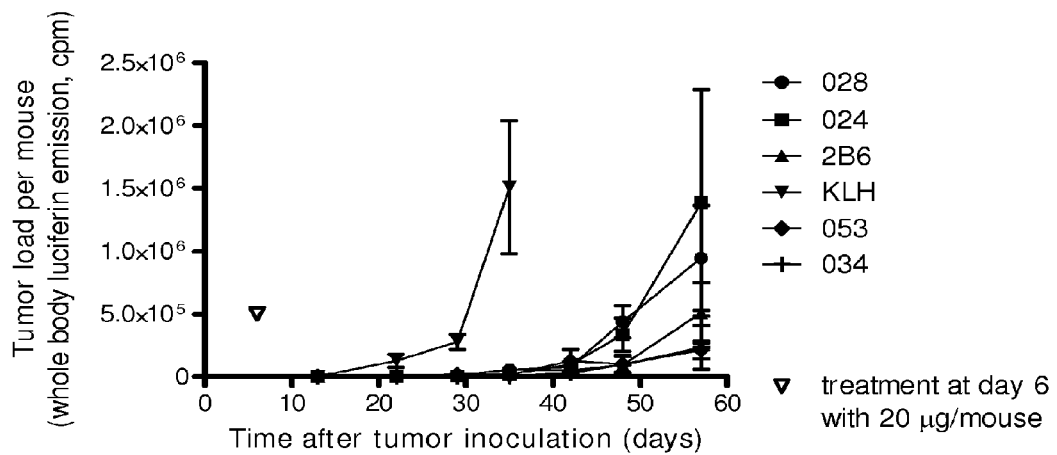
FIGS. 6A-6C show anti-tumor efficacy of anti-CD32b antibodies in vivo in a xenograft tumor model in SCID mice. Antibodies were administered at day 6 (FIGS. 6A and 6B) or 14 days after tumor challenge (FIG. 6C); Data shown are mean tumor loads per group ±SEM.

As can be seen in FIG. 6A, tumor outgrowth was inhibited to a similar extent by administration of HuMab 024, 028, 034, 053 or 2B6 at day six. Tumor outgrowth was significantly delayed by all antibodies tested compared to treatment with the isotype control antibody HuMab-KLH (p<0.05 at day 13, 22, 29 and 33 for HuMabs 024, 034 and 053; p<0.05 at day 13, 22 and 33 for HuMab 028; calculated by one-way ANOVA on log-transformed data, followed by Tukey's multiple comparison test.).

Figure 6B:
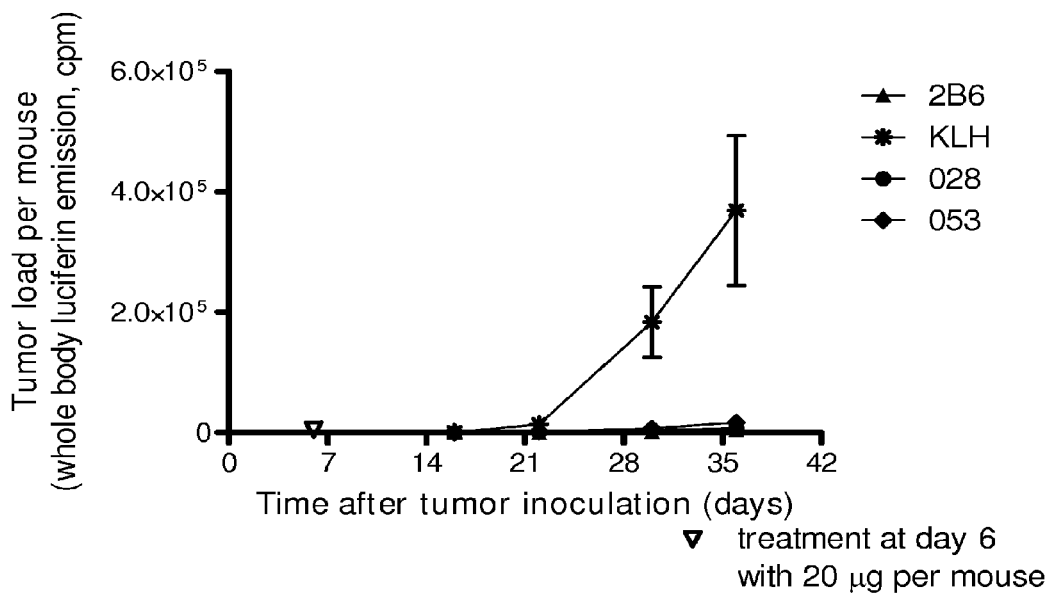

FIG. 6B depicts an experiment in which tumor growth of Daudi cells was inhibited almost completely by treatment at day six with HuMab 028, 053 or 2B6. The inhibition was significant compared to treatment with the isotype control antibody HuMab-KLH (p<0.05; calculated by one-way ANOVA on log-transformed data, followed by Tukey's multiple comparison test).

Figure 6C:
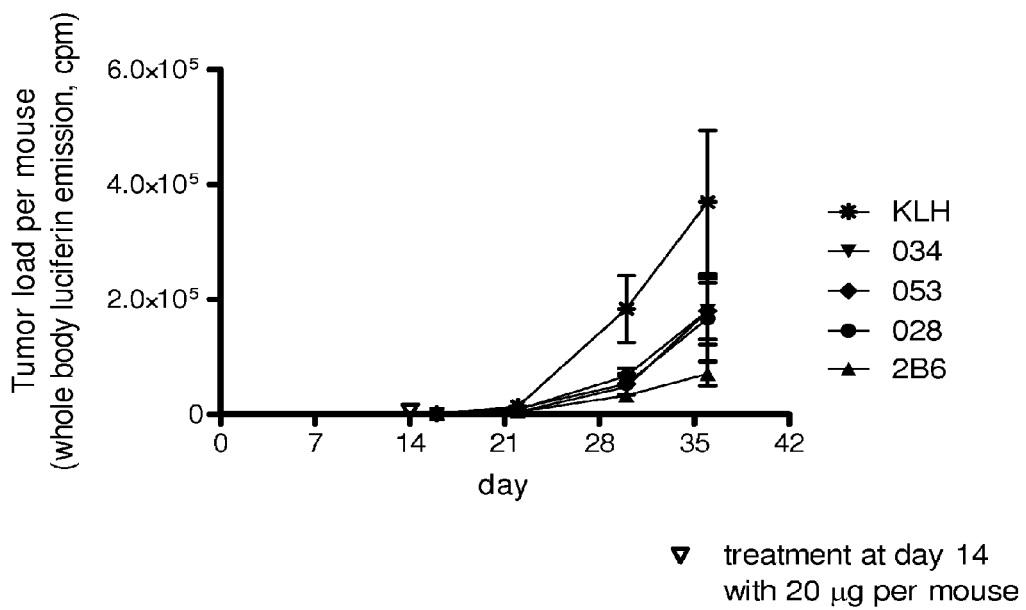

FIG. 6C shows that treatment at day 14 with HuMabs 028, 034 and 053 only slightly inhibited tumor outgrowth as compared to treatment with the isotype control antibody HuMab-KLH (day 6). The difference between the anti-CD32b-treated groups was not significant.

Example 20

ADCC

Figure 7:
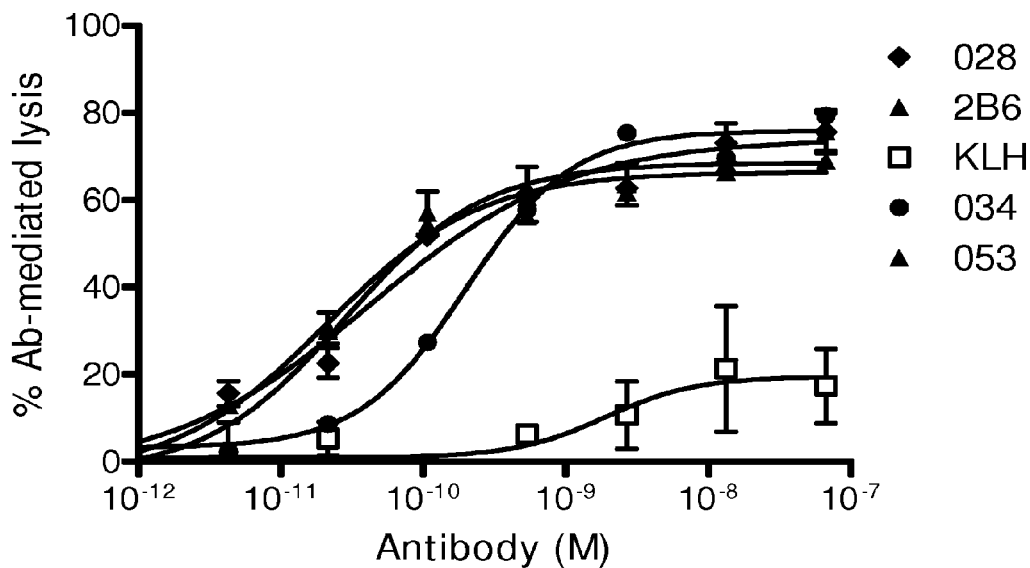
FIG. 7 shows the ability of anti-CD32b-antibodies to induce lysis of Daudi cells by ADCC as compared to HuMab-KLH. Data shown are means of triplicates±SEM.

Preparation of target cells (Daudi cells) and effector cells and set up of the ADCC assay were described supra. Antibody 028 was purified from hybridoma material, whereas antibodies 034, 053 and 2B6 were purified from transiently transfected HEK-293F cells. FIG. 7 depicts a representative experiment and shows that all tested anti-CD32b HuMabs induced lysis of Daudi cells by ADCC with efficiencies comparable with that of 2B6 (Table 7). All HuMabs were able to induce a similar maximum level of antibody-mediated lysis.

TABLE 7

EC$_{50}$ values of CD32b-specific antibodies obtained in ADCC using Daudi cells

| HuMab | EC$_{50}$ (nM) Daudi |
|---|---|
| 028 | 0.29 |
| 034 | 0.38 |
| 053 | 0.33 |
| 2B6 | 0.25 |
| KLH | N.A. |

EC$_{50}$ values are the mean of at least 4 experiments (using effector cells from a different donor each time)
N.A. not applicable, EC$_{50}$ could not be calculated due to low levels of ADCC.

Example 21

Binding of Anti-CD32b HuMabs to Membrane-Bound CD32b1 and CD32b2, Expressed on IIA1.6 Cells To analyze binding of anti-CD32b HuMabs to CD32b1 and CD32b2, IIA1.6 cells transfected with full length CD32b1 or CD32b2 (van den Herik-Oudijk et al., 1994) were prepared as described supra. The assay was performed as described supra. Flow cytometry was performed on a FACS Canto II (BD Biosciences). HuMab-KLH was used as isotype control antibody.

Figure 8A:
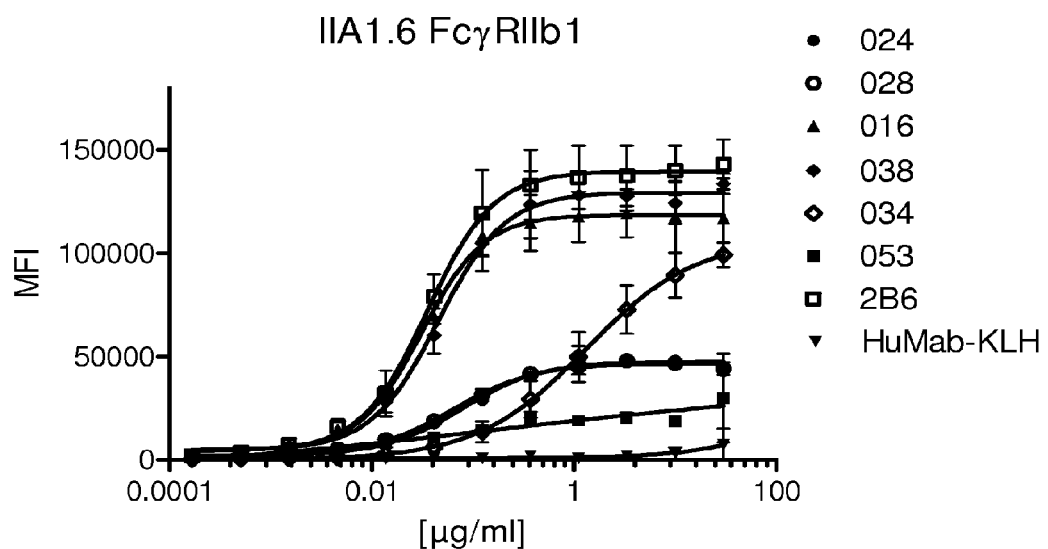
FIGS. 8A and 8B show binding of anti-CD32b-antibodies to membrane-bound CD32b1 (FIG. 8A) and CD32b2 (FIG. 8B) expressed on IIA1.6 cells. Data shown are mean MFI±stdev of three independent experiments.
Figure 8B:
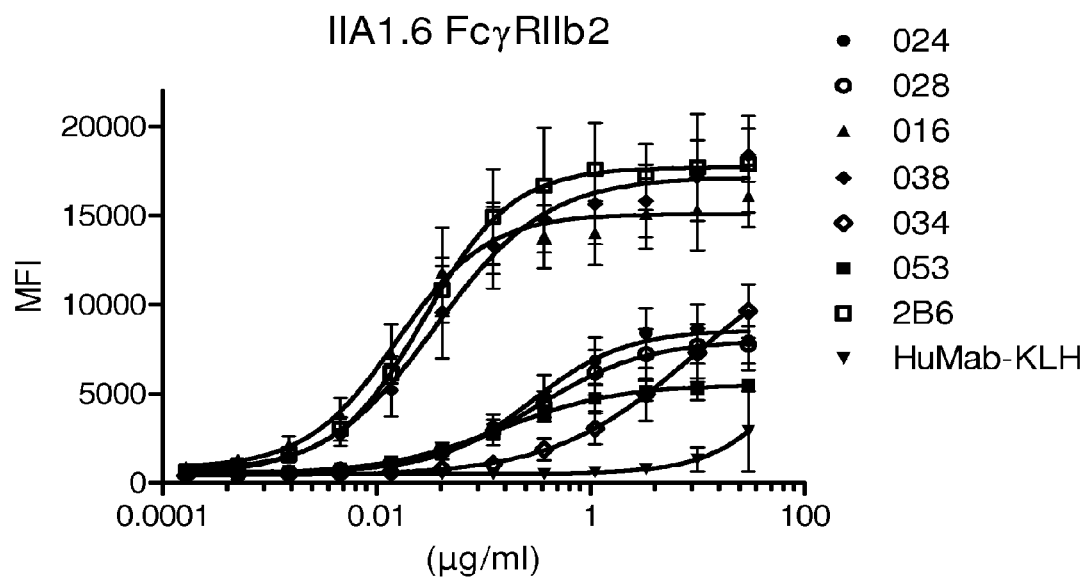

FIGS. 8A and B show that all tested HuMabs bound to both CD32b1- and CD32b2-expressing cells in a dose-dependent manner. As shown in Table 8, $EC_{50}$ values were different for binding to CD32b1- and CD32b2-expressing cells, and the ratio of the $EC_{50}$ values differed between individual antibodies. HuMab 024, 028, 034 and 053 showed values lower than 1, reflecting a preference for binding to CD32b1. In contrast, 2B6, 016 and 038 show $EC_{50}$ values for binding CD32b1-expressing cells comparable to or higher than those for binding CD32b2-expressing cells. HuMabs 024, 028, 034 and 053 show at least fourfold higher binding preference to CD32b1 compared with 2B6. These observations may indicate that in B cell malignancies the anti-CD32b HuMabs will bind preferentially to the B cells, whereas 2B6 antibodies will bind equally well to both B cells and myeloid cells.

TABLE 8

EC50 values of binding of anti-CD32b HuMabs to IIA1.6-CD32b1 and IIA1.6-CD32b2 cells.

| HuMab | $EC_{50}$ (nM) IIA1.6-CD32b1 | $EC_{50}$ (nM) IIA1.6-CD32b2 | Ratio $EC_{50}$ (CD32b1)/ $EC_{50}$(CD32b2) |
|---|---|---|---|
| 024 | 0.52 | 1.96 | 0.27 |
| 028 | 0.44 | 2.18 | 0.20 |
| 016 | 0.21 | 0.11 | 1.89 |
| 038 | 0.32 | 0.27 | 1.18 |
| 034 | 10.42 | 68.97 | 0.15 |
| 053 | 0.20 | 1.06 | 0.19 |
| 2B6 | 0.24 | 0.19 | 1.27 |
| KLH | N.A. | N.A. | N.A. |

Data shown are the mean $EC_{50}$ values of three independent experiments.
N.A. $EC_{50}$ value could not be calculated due to low levels of binding.

Example 22

Binding of Anti-CD32b HuMabs to Mantle Cell Lymphoma Cells

Mantle cell lymphoma cell line JeKo-1 (DSMZ, ACC 553) was cultured in RPMI-1640 culture medium supplemented with 20% FBS (PerBio Science), 100 IU/ml penicillin and 100 mg/ml streptomycin (both from Gibco BRL).

Staining with anti-CD32b HuMabs (all purified from transiently transfected HEK-293F cells) and detection and analysis of binding were performed as described supra. Flow cytometry was performed on a FACS Canto II (BD Biosciences). HuMab-KLH was used as isotype control antibody.

Figure 9:
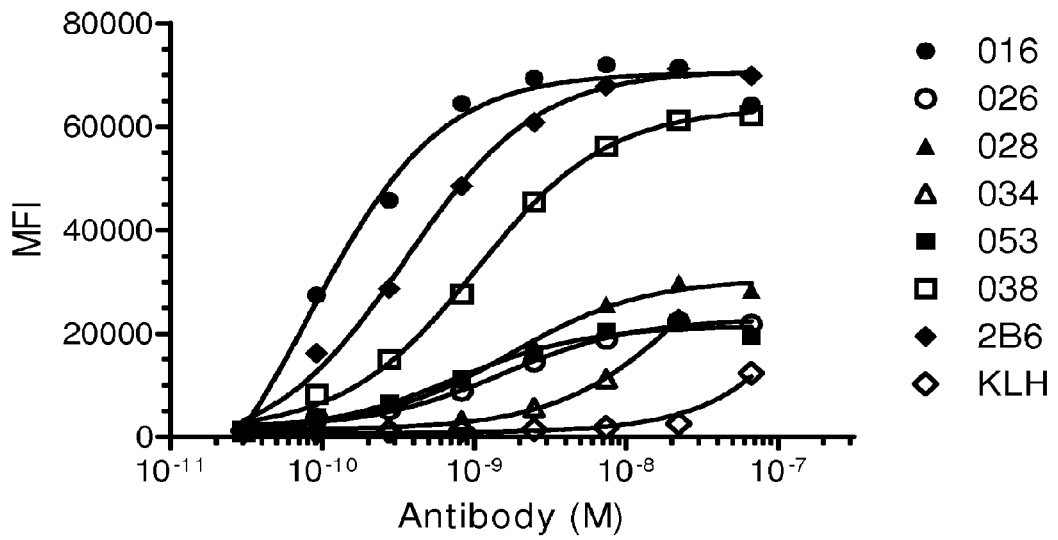
FIG. 9 shows binding of anti-CD32b-antibodies to Mantle cell lymphoma cells.

FIG. 9 depicts a representative experiment of two experiments performed and shows that all tested anti-CD32b HuMabs bind to mantle cell lymphoma cell line JeKo-1. As shown in Table 9 the lowest EC50 value was observed for HuMab 016. EC50 values for HuMab 2B6, 038, 053, 026 and 028 were somewhat higher. HuMab 034 showed the highest EC50 value.

TABLE 9

| HuMab | $EC_{50}$ (nM) |
|---|---|
| 016 | 0.058 |
| 026 | 1.23 |
| 028 | 1.38 |

TABLE 9-continued

| HuMab | $EC_{50}$ (nM) |
|---|---|
| 034 | 22.3 |
| 038 | 0.72 |
| 053 | 0.72 |
| 2B6 | 0.34 |
| KLH | N.A |

$EC_{50}$ values are the means of 2 independent experiments.
N.A. not applicable, $EC_{50}$ value could not be calculated due to lack of binding Example 23

Binding of Anti-CD32b HuMabs to Human Peripheral Blood Leukocytes

Perhipheral blood from healthy volunteers (University Medical Center Utrecht) was diluted four times in FACS buffer (PBS+0.4% BSA+0.02% $NaN_3$) and incubated with either $Alexa^{488}$-conjugated HuMabs (final concentration 2 µg/ml) or serially diluted biotinylated HuMabs. Incubations were performed in presence of phycoerythrin (PE)-labeled anti-CD19, -CD3, -CD16, -CD14 and -CD56 antibodies (BD Biosciences, San Jose Calif.) to identify cell populations (resp. B cells, T cells, granulocytes, monocytes and NK cells) in a final volume of 100 µl. After 30 minutes at 4° C., samples were spun (300 g, 3 min), supernatant was removed and erythrocytes were lysed by incubation (10 min, 4° C.) with 200 µl lysis buffer (BD Biosciences) followed by two times washing in FACS buffer. Samples that had been incubated with biotinylated HuMabs were resuspended in fluorescein isothiocyanate (FITC)-conjugated streptavidin (DAKO, Glostrup, Denmark) in a final volume of 100 µl, incubated for 30 minutes and washed two times in FACS buffer. All samples were resuspended in 100 µl FACS buffer and analyzed using the FACS Canto II (BD Biosciences)

Figure 10A:
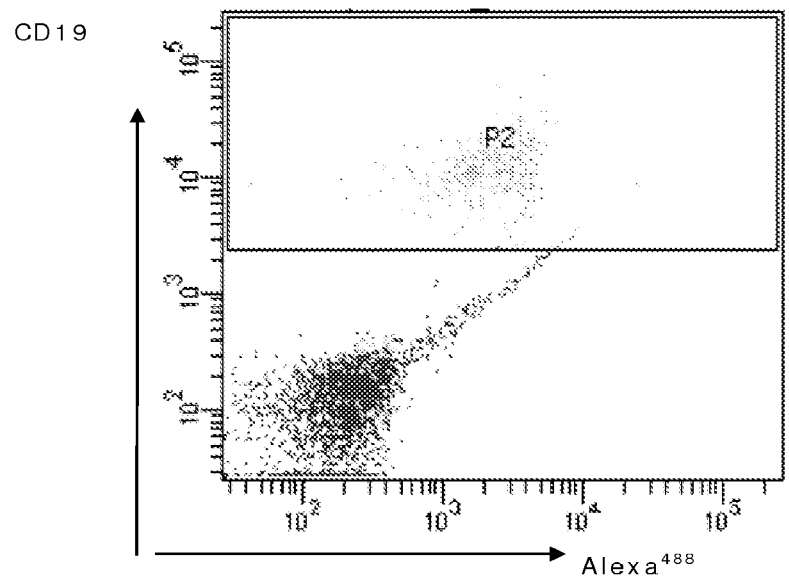
FIGS. 10A-10C show binding of anti-CD32b-antibodies to human peripheral blood leukocytes.
Figure 10A:
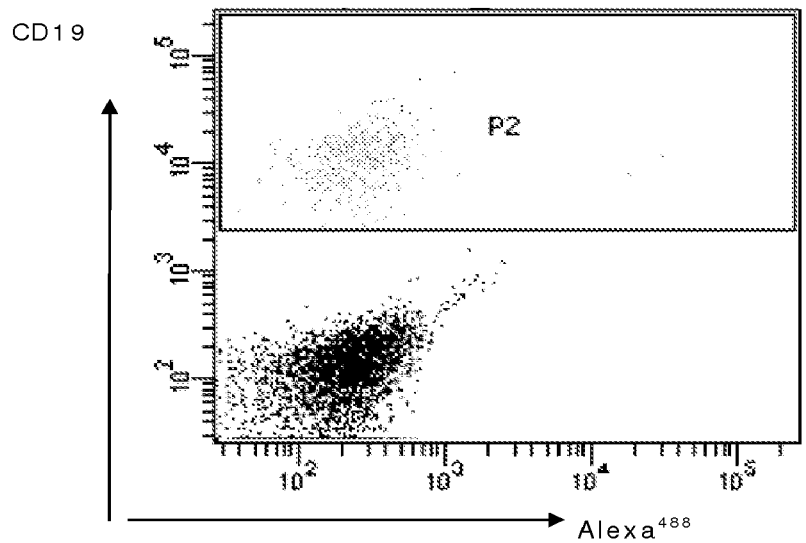
Figure 10B:
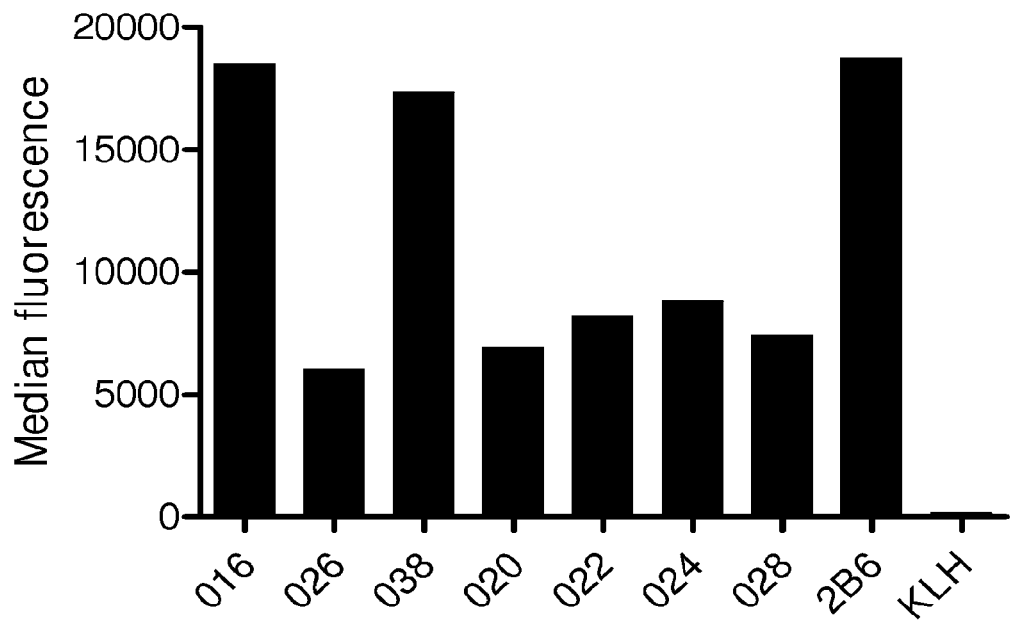
Figure 10B:
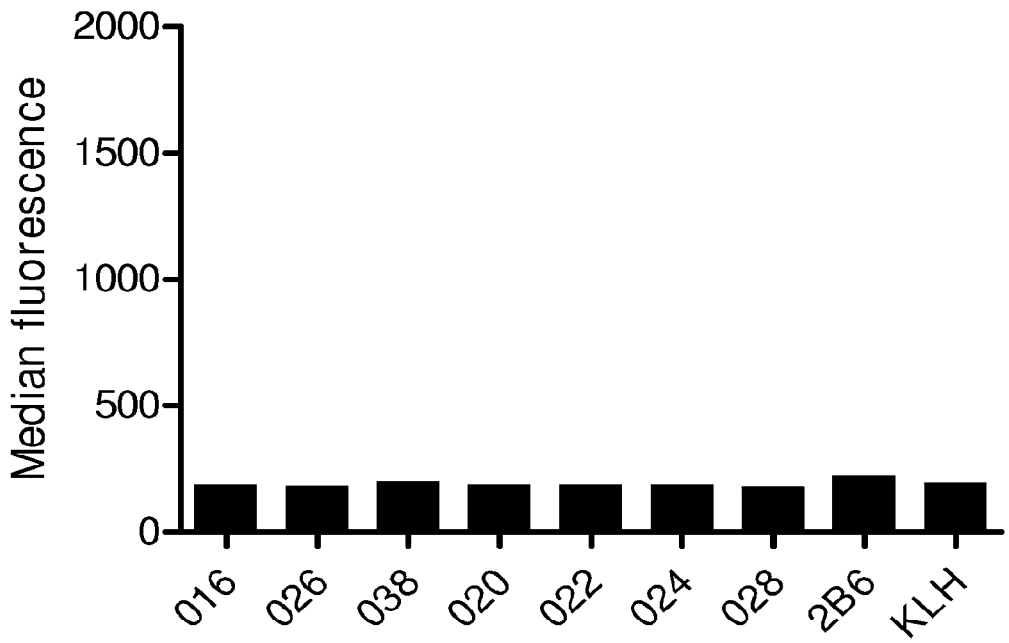
Figure 10B:
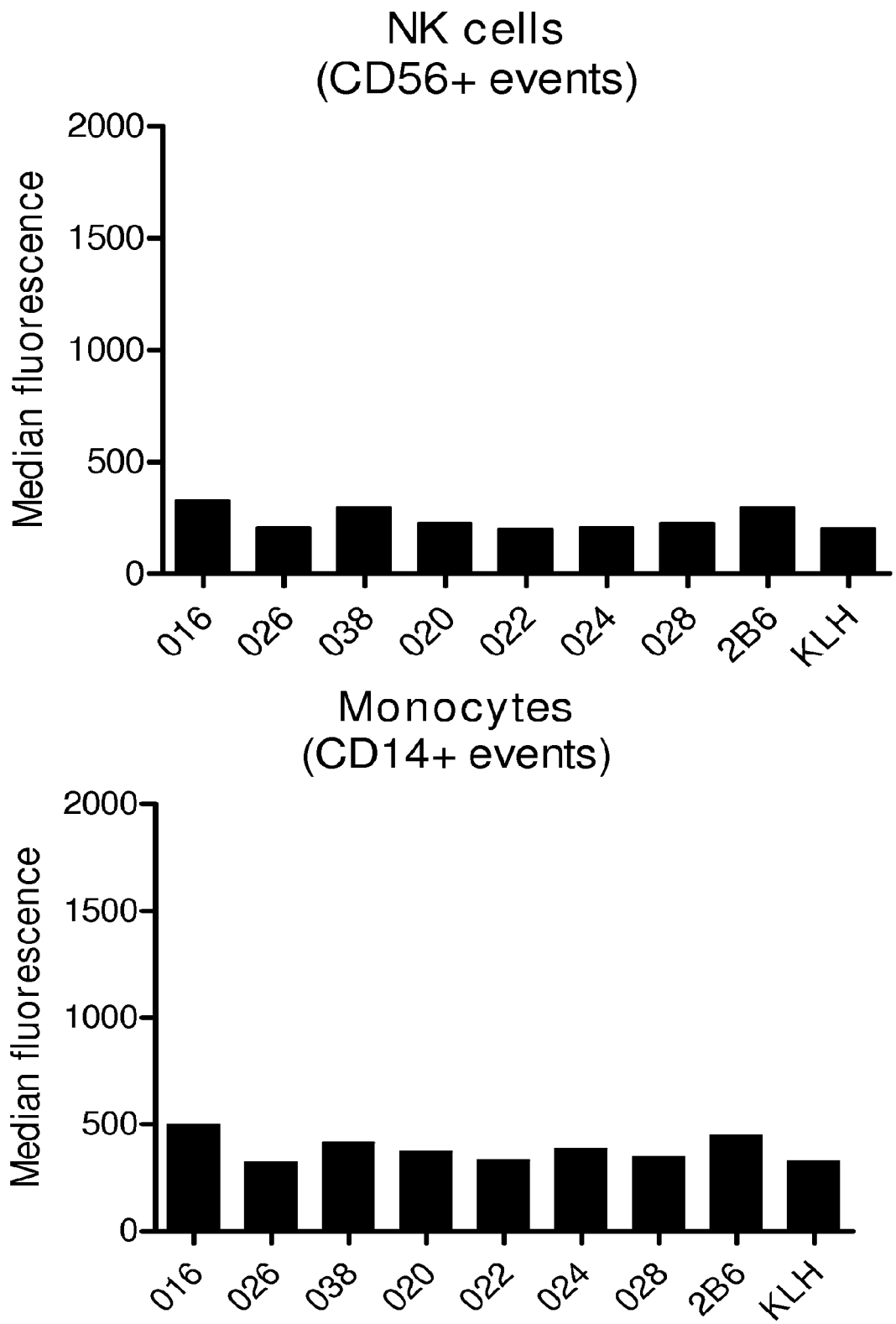
Figure 10B:
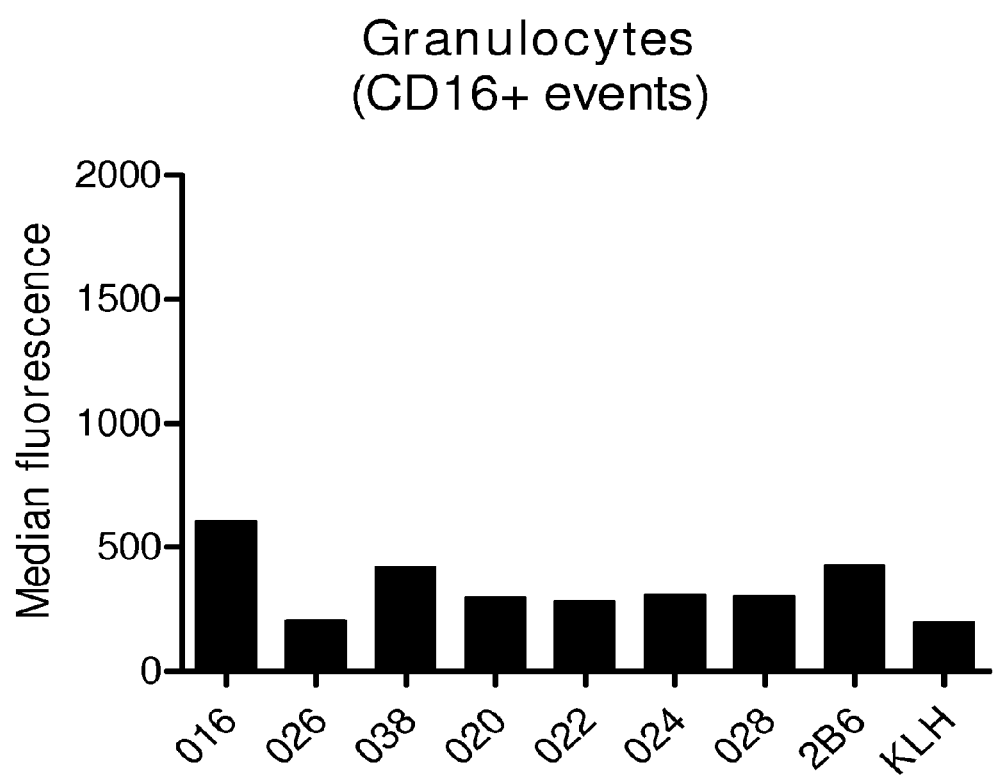
Figure 10C:
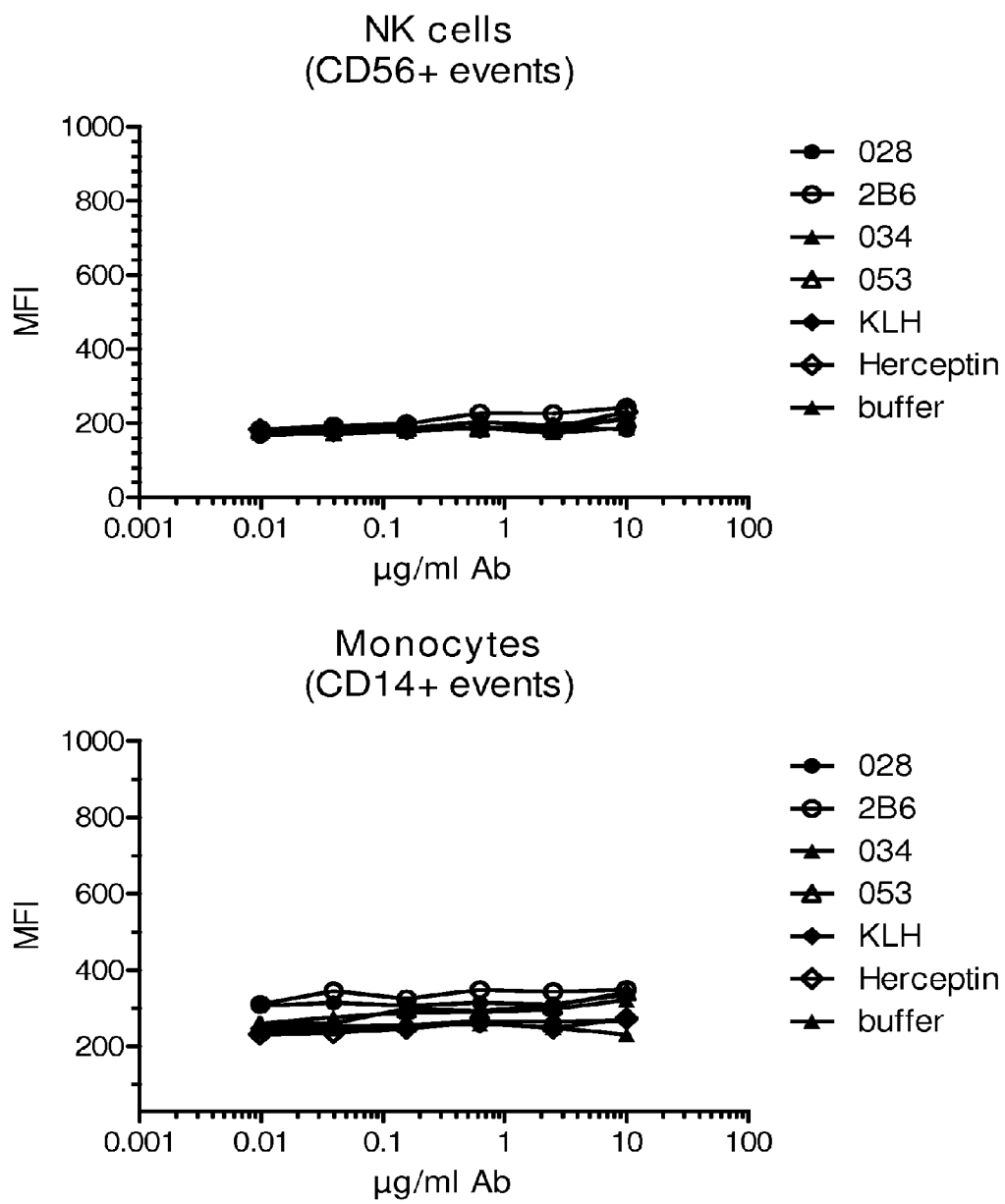
Figure 10C:
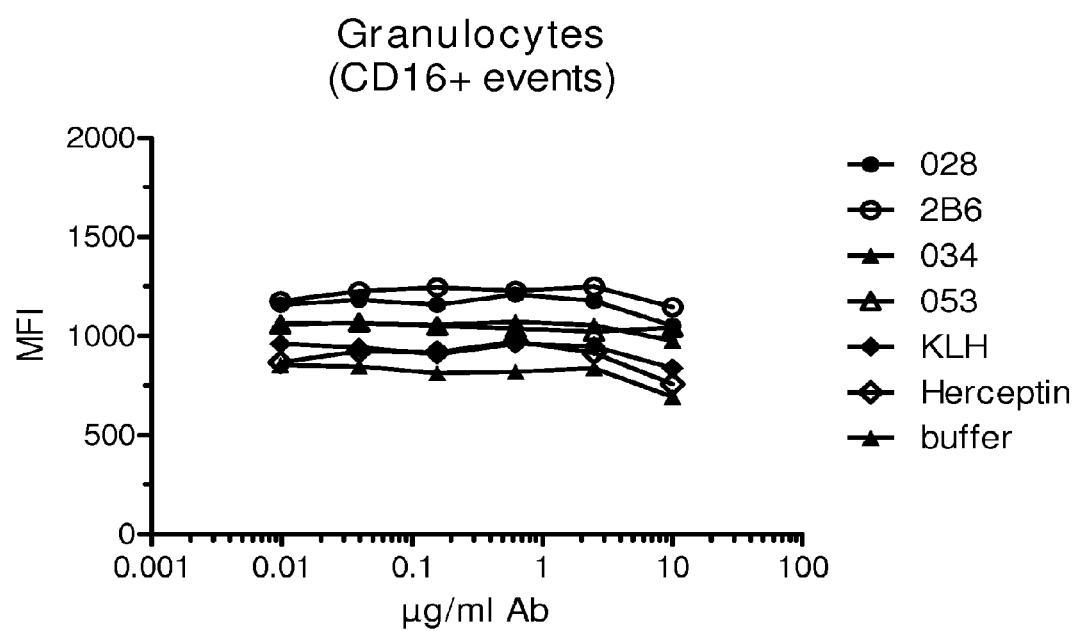

FIG. 10A is a representative FACS plot showing enhanced Alexa488-fluorescence in presence of 028 but not HuMab-KLH in the B cell (CD19+) population (within the lymphocyte gate). Binding of $Alexa^{488}$-conjugated CD32b HuMabs to the other cell populations was analyzed similarly and representative results for 1 of 8 donors are plotted in FIG. 10B. All anti-CD32b antibodies efficiently bound to B cells; the highest binding levels were observed for 016, 038 and 2B6. Binding to all other cell types was marginal, although the median fluorescence for 016, 038 and 2B6 exceeded background fluorescence levels on monocytes and granulocytes. Similar results were obtained when biotinylated anti-CD32b antibodies were used as shown in FIG. 10C. HuMabs 028, 034, 053 and 2B6 showed specific binding to B cells already at low antibody concentrations. Binding to all other cell types was marginal or absent In summary, CD32b HuMabs bind peripheral blood B cells with little or no binding to other peripheral blood leukocytes.

Example 24

Binding of Anti-CD32b HuMabs to CD32bECDHis in Western Blot

Recombinant CD32bECDHis (described supra) was loaded on SDS-PAGE and blotted on nitrocellulose (0.5 µg/lane). After blotting, the nitrocellulose membrane was incubated with 5% ELK powder (Campina, The Netherlands) in PBS (30 min, RT), followed by incubation with 0.5

μg/ml CD32b HuMabs (all purified from transiently transfected HEK cells) or HuMab-KLH as isotype control antibody (1 h, RT). The nitrocellulose membrane was washed four times in PBS (5 min, RT), incubated with F(ab')2 fragments of horseradishperoxidase (HRP)-conjugated goat-anti-human IgG Fc (Jackson Immunoresearch Europe) (1 h, RT) and washed four times (5 min, RT). Binding of the conjugated antibody was detected by incubating the blot with Supersignal Extended Duration Substrate (Pierce, Rockford Ill.; 5 min, RT) and visualized (using Ultima 16si Pro (Isogen Life Science, The Netherlands))'.

Figure 11A:
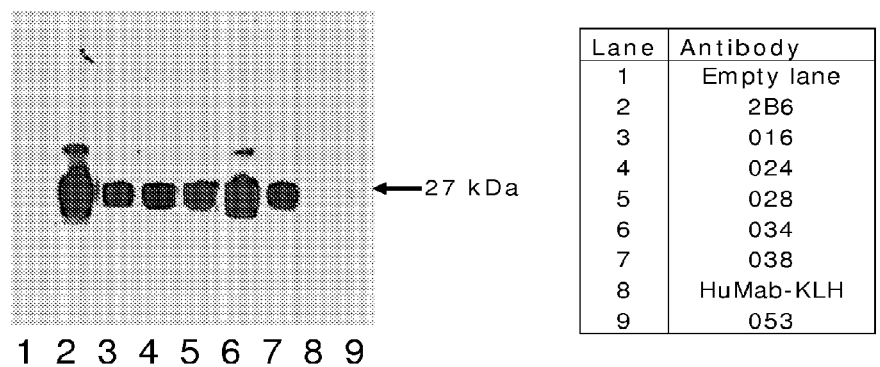
FIGS. 11A and 11B show binding of anti-CD32b-antibodies to CD32bECDHis in Western Blot. In (FIG. 11B) under reducing (lanes 1-6) and non-reducing conditions (9-12).

As shown in FIG. 11A, CD32bECDHis is efficiently recognized by 2B6, 016, 024, 028, 034 and 038, indicating that the epitope recognized by these antibodies is at least partly preserved after denaturation and reduction of the protein. In contrast, 053 did not show binding. The isotype control antibody HuMab KLH did not show binding.

Figure 11B:
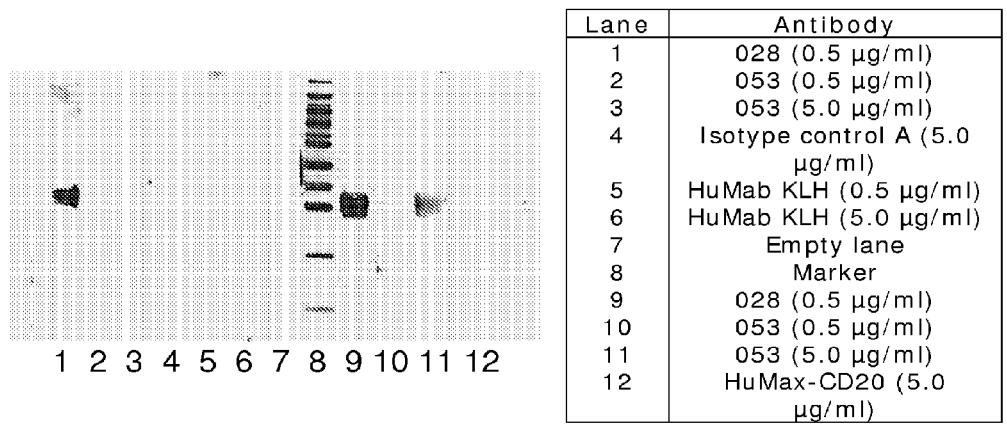

In a new set of Western Blot experiment (performed as described supra), binding of 028 and 053 to reduced and non-reduced CD32bECDHis was tested. HuMab-KLH and an additional antibody of irrelevant specificity (isotype ctrl A) were included as isotype control antibodies. As shown in FIG. 11B, 028 showed binding to reduced and non-reduced CD32bECDHis protein. In contrast, 053 did not bind to reduced CD32bECDHis at both low and high antibody concentrations, whereas some binding was visible to non-reduced CD32bECDHis at the highest antibody concentration. Isotype control antibodies did not show binding at any concentration tested. This suggests that the epitope recognized by 053 does not bind a linear epitope and may at least partly be dependent on disulfide bonds.

The invention claimed is:

1. A method for inhibiting growth and/or proliferation of a tumor cell expressing CD32b, comprising administration, to an individual in need thereof, of an anti-CD32b antibody which comprises:
   a) a VH region comprising CDR1, 2 and 3 sequences as set forth in SEQ ID NO:2, 3 and 4, and a VL region comprising CDR1, 2 and 3 sequences as set forth in SEQ ID NO: 6, 7 and 8,
   b) a VH region comprising CDR1, 2 and 3 sequences as set forth in SEQ ID NO:10, 11 and 12, and a VL region comprising CDR1, 2 and 3 sequences as set forth in SEQ ID NO:14, 15 and 16,
   c) a VH region comprising CDR1, 2 and 3 sequences as set forth in SEQ ID NO:18, 19 and 20, and a VL region comprising CDR1, 2 and 3 sequences as set forth in SEQ ID NO:22, 23 and 24,
   d) a VH region comprising CDR1, 2 and 3 sequences as set forth in SEQ ID NO:26, 27 and 28, and a VL region comprising CDR1, 2 and 3 sequences as set forth in SEQ ID NO:30, 31 and 32,
   e) a VH region comprising CDR1, 2 and 3 sequences as set forth in SEQ ID NO:34, 35 and 36, and a VL region comprising CDR1, 2 and 3 sequences as set forth in SEQ ID NO:38, 39 and 40,
   f) a VH region comprising CDR1, 2 and 3 sequences as set forth in SEQ ID NO:42, 43 and 44, and a VL region comprising CDR1, 2 and 3 sequences as set forth in SEQ ID NO:14, 15 and 16,
   g) a VH region comprising CDR1, 2 and 3 sequences as set forth in SEQ ID NO: 46, 47 and 48, and a VL region comprising CDR1, 2 and 3 sequences as set forth in SEQ ID NO: 50, 51 and 52,
   h) a VH region comprising CDR1, 2 and 3 sequences as set forth in SEQ ID NO: 54, 55 and 56, and a VL region comprising CDR1, 2 and 3 sequences as set forth in SEQ ID NO: 58, 59 and 60,
   i) a VH region comprising CDR1, 2 and 3 sequences as set forth in SEQ ID NO: 62, 63 and 64, and a VL region comprising CDR1, 2 and 3 sequences as set forth in SEQ ID NO: 66, 67 and 68, or
j) a VH region comprising CDR1, 2 and 3 sequences as set forth in SEQ ID NO: 70, 71 and 72, and a VL region comprising CDR1, 2 and 3 sequences as set forth in SEQ ID NO: 74, 75 and 76.

2. The method of claim 1, wherein the tumor cell is a B-cell neoplasm.

3. The method of claim 2, wherein the B-cell neoplasm is selected from the group consisting of: small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

4. The method of claim 1, wherein the anti-CD32b antibody is administered in combination with a therapeutic antibody.

5. The method of claim 4, wherein the therapeutic antibody is selected from the group consisting of an anti-CD20 therapeutic antibody and an anti-CD38 therapeutic antibody.

6. The method of claim 1, wherein the antibody comprises:
   a) a VH region comprising the sequence as set forth in SEQ ID NO:1 and a VL region comprising the sequence as set forth in SEQ ID NO: 5,
   b) a VH region comprising the sequence as set forth in SEQ ID NO:9 and a VL region comprising the sequence as set forth in SEQ ID NO:13,
   c) a VH region comprising the sequence as set forth in SEQ ID NO:17 and a VL region comprising the sequence as set forth in SEQ ID NO:21,
   d) a VH region comprising the sequence as set forth in SEQ ID NO:25 and a VL region comprising the sequence as set forth in SEQ ID NO:29,
   e) a VH region comprising the sequence as set forth in SEQ ID NO:33 and a VL region comprising the sequence as set forth in SEQ ID NO:37,
   f) a VH region comprising the sequence as set forth in SEQ ID NO:41 and a VL region comprising the sequence as set forth in SEQ ID NO:21,
   g) a VH region comprising the sequence as set forth in SEQ ID NO:45 and a VL region comprising the sequence as set forth in SEQ ID NO:49,
   h) a VH region comprising the sequence as set forth in SEQ ID NO:61 and a VL region comprising the sequence as set forth in SEQ ID NO:65, or
   i) a VH region comprising the sequence as set forth in SEQ ID NO:69 and a VL region comprising the sequence as set forth in SEQ ID NO:73.

7. The method of claim 1, wherein the antibody is a bispecific molecule comprising an anti-CD32b antibody and a second binding specificity.

8. The method of claim 1, wherein the tumor cell is involved in Acute myelogenous leukemia (AML); Chronic lymphocytic leukemia (CLL) or Chronic myelogenous leukemia (CML).

9. The method of claim 1, wherein the tumor cell is involved in peripheral T-Cell lymphomas or cutaneous T-Cell lymphoma.

10. The method of claim 1, the tumor cell is involved in melanoma.

11. The method of claim 1, wherein the anti-CD32b antibody is administered in combination with a therapeutic agent.

12. The method of claim 11, wherein the therapeutic agent is selected from the group consisting of a cytotoxic, chemotherapeutic or anti-angiogenic agent.

13. The method of claim 12, wherein the chemotherapeutic agent is selected from the group of an antimetabolite, an alkylating agent, an anti-mitotic agent, a growth factor inhibitor, and a tyrosine kinase inhibitor.

14. A method for stimulating the immune system, comprising administering, to an individual in need thereof, an anti-CD32b antibody comprising:
   a) a VH region comprising CDR1, 2 and 3 sequences as set forth in SEQ ID NO:2, 3 and 4, and a VL region comprising CDR1, 2 and 3 sequences as set forth in SEQ ID NO: 6, 7 and 8,
   b) a VH region comprising CDR1, 2 and 3 sequences as set forth in SEQ ID NO:10, 11 and 12, and a VL region comprising CDR1, 2 and 3 sequences as set forth in SEQ ID NO:14, 15 and 16,
   c) a VH region comprising CDR1, 2 and 3 sequences as set forth in SEQ ID NO:18, 19 and 20, and a VL region comprising CDR1, 2 and 3 sequences as set forth in SEQ ID NO:22, 23 and 24,
   d) a VH region comprising CDR1, 2 and 3 sequences as set forth in SEQ ID NO:26, 27 and 28, and a VL region comprising CDR1, 2 and 3 sequences as set forth in SEQ ID NO:30, 31 and 32,
   e) a VH region comprising CDR1, 2 and 3 sequences as set forth in SEQ ID NO:34, 35 and 36, and a VL region comprising CDR1, 2 and 3 sequences as set forth in SEQ ID NO:38, 39 and 40,
   f) a VH region comprising CDR1, 2 and 3 sequences as set forth in SEQ ID NO:42, 43 and 44, and a VL region comprising CDR1, 2 and 3 sequences as set forth in SEQ ID NO:14, 15 and 16,
   g) a VH region comprising CDR1, 2 and 3 sequences as set forth in SEQ ID NO: 46, 47 and 48, and a VL region comprising CDR1, 2 and 3 sequences as set forth in SEQ ID NO: 50, 51 and 52,
   h) a VH region comprising CDR1, 2 and 3 sequences as set forth in SEQ ID NO: 54, 55 and 56, and a VL region comprising CDR1, 2 and 3 sequences as set forth in SEQ ID NO: 58, 59 and 60,
   i) a VH region comprising CDR1, 2 and 3 sequences as set forth in SEQ ID NO: 62, 63 and 64, and a VL region comprising CDR1, 2 and 3 sequences as set forth in SEQ ID NO: 66, 67 and 68, or
   j) a VH region comprising CDR1, 2 and 3 sequences as set forth in SEQ ID NO: 70, 71 and 72, and a VL region comprising CDR1, 2 and 3 sequences as set forth in SEQ ID NO: 74, 75 and 76.

15. A method for stimulating the immune system, comprising administering, to an individual in need thereof, an anti-CD32b antibody comprising:
   a) a VH region comprising the sequence as set forth in SEQ ID NO:1 and a VL region comprising the sequence as set forth in SEQ ID NO: 5,
   b) a VH region comprising the sequence as set forth in SEQ ID NO:9 and a VL region comprising the sequence as set forth in SEQ ID NO:13, c) a VH region comprising the sequence as set forth in SEQ ID NO:17 and a VL region comprising the sequence as set forth in SEQ ID NO:21,
d) a VH region comprising the sequence as set forth in SEQ ID NO:25 and a VL region comprising the sequence as set forth in SEQ ID NO:29,
e) a VH region comprising the sequence as set forth in SEQ ID NO:33 and a VL region comprising the sequence as set forth in SEQ ID NO:37,
f) a VH region comprising the sequence as set forth in SEQ ID NO:41 and a VL region comprising the sequence as set forth in SEQ ID NO:21,
g) a VH region comprising the sequence as set forth in SEQ ID NO:45 and a VL region comprising the sequence as set forth in SEQ ID NO:49,
h) a VH region comprising the sequence as set forth in SEQ ID NO:61 and a VL region comprising the sequence as set forth in SEQ ID NO:65, or
i) a VH region comprising the sequence as set forth in SEQ ID NO:69 and a VL region comprising the sequence as set forth in SEQ ID NO:73.

16. A method for stimulating the immune system, comprising administering, to an individual in need thereof, a bispecific molecule comprising an anti-CD32b antibody and a second binding specificity, wherein the anti-CD32b antibody comprises:
a) a VH region comprising CDR1, 2 and 3 sequences as set forth in SEQ ID NO:2, 3 and 4, and a VL region comprising CDR1, 2 and 3 sequences as set forth in SEQ ID NO: 6, 7 and 8,
b) a VH region comprising CDR1, 2 and 3 sequences as set forth in SEQ ID NO:10, 11 and 12, and a VL region comprising CDR1, 2 and 3 sequences as set forth in SEQ ID NO:14, 15 and 16,
c) a VH region comprising CDR1, 2 and 3 sequences as set forth in SEQ ID NO:18, 19 and 20, and a VL region comprising CDR1, 2 and 3 sequences as set forth in SEQ ID NO:22, 23 and 24,
d) a VH region comprising CDR1, 2 and 3 sequences as set forth in SEQ ID NO:26, 27 and 28, and a VL region comprising CDR1, 2 and 3 sequences as set forth in SEQ ID NO:30, 31 and 32,
e) a VH region comprising CDR1, 2 and 3 sequences as set forth in SEQ ID NO:34, 35 and 36, and a VL region comprising CDR1, 2 and 3 sequences as set forth in SEQ ID NO:38, 39 and 40,
f) a VH region comprising CDR1, 2 and 3 sequences as set forth in SEQ ID NO:42, 43 and 44, and a VL region comprising CDR1, 2 and 3 sequences as set forth in SEQ ID NO:14, 15 and 16,
g) a VH region comprising CDR1, 2 and 3 sequences as set forth in SEQ ID NO: 46, 47 and 48, and a VL region comprising CDR1, 2 and 3 sequences as set forth in SEQ ID NO: 50, 51 and 52,
h) a VH region comprising CDR1, 2 and 3 sequences as set forth in SEQ ID NO: 54, 55 and 56, and a VL region comprising CDR1, 2 and 3 sequences as set forth in SEQ ID NO: 58, 59 and 60,
i) a VH region comprising CDR1, 2 and 3 sequences as set forth in SEQ ID NO: 62, 63 and 64, and a VL region comprising CDR1, 2 and 3 sequences as set forth in SEQ ID NO: 66, 67 and 68, or
j) a VH region comprising CDR1, 2 and 3 sequences as set forth in SEQ ID NO: 70, 71 and 72, and a VL region comprising CDR1, 2 and 3 sequences as set forth in SEQ ID NO: 74, 75 and 76.

* * * * *